US011154608B2

(12) United States Patent
Chang et al.

(10) Patent No.: US 11,154,608 B2
(45) Date of Patent: Oct. 26, 2021

(54) DENGUE VIRUS E-GLYCOPROTEIN POLYPEPTIDES CONTAINING MUTATIONS THAT ELIMINATE IMMUNODOMINANT CROSS-REACTIVE EPITOPES

(71) Applicant: The Government of the U.S.A. as rep. by the Secretary of the Dept. of Health and Human Services, Bethesda, MD (US)

(72) Inventors: Gwong-Jen J. Chang, Fort Collins, CO (US); Wayne D. Crill, Boulder, CO (US); Holly R. Hughes, Fort Collins, CO (US); Brent S. Davis, Fort Collins, CO (US)

(73) Assignee: The Government of the United States of America as represented by the Secretary of the Department of Health and Human Services, Atlanta, GA (US)

( * ) Notice: Subject to any disclaimer, the term of this patent is extended or adjusted under 35 U.S.C. 154(b) by 91 days.

(21) Appl. No.: 16/745,986

(22) Filed: Jan. 17, 2020

(65) Prior Publication Data

US 2020/0147201 A1    May 14, 2020

Related U.S. Application Data

(60) Continuation of application No. 16/107,119, filed on Aug. 21, 2018, now Pat. No. 10,568,956, which is a division of application No. 15/262,268, filed on Sep. 12, 2016, now Pat. No. 10,092,637, which is a division of application No. 14/352,812, filed as application No. PCT/US2012/060872 on Oct. 18, 2012, now abandoned.

(60) Provisional application No. 61/549,348, filed on Oct. 20, 2011.

(51) Int. Cl.
*A61K 39/12* (2006.01)
*C07K 14/005* (2006.01)
*C12N 7/00* (2006.01)
*A61K 39/00* (2006.01)

(52) U.S. Cl.
CPC .......... *A61K 39/12* (2013.01); *C07K 14/005* (2013.01); *C12N 7/00* (2013.01); *A61K 2039/5258* (2013.01); *A61K 2039/53* (2013.01); *A61K 2039/57* (2013.01); *A61K 2039/575* (2013.01); *A61K 2039/6031* (2013.01); *A61K 2039/6075* (2013.01); *A61K 2039/70* (2013.01); *C12N 2770/24122* (2013.01); *C12N 2770/24123* (2013.01); *C12N 2770/24134* (2013.01); *C12N 2770/24151* (2013.01); *C12N 2770/24171* (2013.01); *Y02A 50/30* (2018.01)

(58) Field of Classification Search
None
See application file for complete search history.

(56) References Cited

U.S. PATENT DOCUMENTS

| 5,853,724 A | 12/1998 | Garrity et al. |
| 7,662,394 B2 | 2/2010 | Chang |
| 2011/0177121 A1 | 7/2011 | Nara et al. |

FOREIGN PATENT DOCUMENTS

| WO | WO 95/06124 | 2/1995 |
| WO | WO 2006/025990 | 3/2006 |
| WO | WO 2011/028963 | 3/2011 |
| WO | WO 2013/009884 A1 | 1/2013 |

OTHER PUBLICATIONS

Chen et al., "A Heterologous DNA Prime-Venezuelan Equine Encephalitis Virus Replicon Particle Boost Dengue Vaccine Regimen Affords Complete Protection from Virus Challenge in Cynomolgus Macaques," *J. Virol.*, vol. 81:11634-11639, 2007.
Chiou et al., "Mutation Analysis of the Cross-Reactive Epitopes of Japanese Encephalitis Virus Envelope Glycoprotein," *J. Gen. Virol.*, vol. 93:1185-1192, 2012.
Crill et al., "A Detailed Mutagenesis Study of Flavivirus Cross-Reactive Epitopes using West Nile Virus-Like Particles," *J. Gen. Virol.*, vol. 88:1169-1174, 2007.
Crill et al., "Humoral Immune Responses of Dengue Fever Patients Using Epitope-Specific Serotype-2 Virus-Like Particle Antigens," *PLoS ONE*, vol. 4:e4991, 2009.
Ding et al., "Superior Neutralizing Antibody Response and Protection in Mine Vaccinated with Heterologous DNA Prime and Virus Like Particle Boost against HPAI H5N1 Virus," *PLoS ONE*, vol. 6:e16563, 2011.
Gromowski et al., "Characterization of Dengue Virus Complex-Specific Neutralizing Epitopes on Envelope Protein Domain III of Dengue 2 Virus," *J Virol* 82(17):8828-8837, 2008.
Guenaga et al., "Heterologous Epitope-Scaffold Prime: Boosting Immuno-Focuses B Cell Responses to the HIV-1 gp41 2F5 Neutralization Determinant," *PLoS ONE*, vol. 6:e16074, 2011.

(Continued)

*Primary Examiner* — Stacy B Chen
(74) *Attorney, Agent, or Firm* — Klarquist Sparkman, LLP

(57) ABSTRACT

Described herein are dengue virus E-glycoprotein polypeptides containing mutations that eliminate immunodominant cross-reactive epitopes associated with immune enhancement. The disclosed dengue virus E-glycoproteins optionally further include mutations that introduce a strong CD4 T cell epitope. The disclosed E-glycoprotein polypeptides, or nucleic acid molecules encoding the polypeptides, can be used, for example, in monovalent or tetravalent vaccines against dengue virus.

20 Claims, 6 Drawing Sheets
Specification includes a Sequence Listing.

(56) References Cited

OTHER PUBLICATIONS

Hughes, Holly Ruth, "Increasing Dengue Virus Vaccine Safety and Immunogenicity by Manipulating Antigenic Determinants of the Flavivirus Envelope Protein," Dissertation, Department of Microbiology, Immunology and Pathology, Colorado State University, Feb. 28, 2011; 217 pages. Copy of e-mail correspondence (1 page) appended to Dissertation.

Hughes et al., "Manipulation of Immunodominant Dengue Virus E Protein Epitopes Reduces Potential Antibody-Dependent Enhancement," *Virol. J.*, vol. 9:115-127, 2012.

Im et al., "Protective Efficacy of Serially Up-Ranked Subdominant CD8+T Cell Epitopes against Virus Challenges," *PLoS ONE*, vol. 7:e1002041, 2011.

Lai et al., "Antibodies to Envelope Glycoprotein of Dengue Virus during the Natural Course of Infection Are Predominantly Cross-Reactive and Recognize Epitopes Containing Highly Conserved Residues at the Fusion Loop of Domain II," *J. Virol.*, vol. 82:6631-6643, 2008.

Mebatsion et al., "Mokola Virus Glycoprotein and Chimeric Proteins Can Replace Rabies Virus Glycoprotein in the Rescue of Infectious Defective Rabies Virus Particles," *J. Virol.*, vol. 69:1444-1451, 1995.

Sukupolvi-Petty et al., "Type- and Subcomplex-Specific Neutralizing Antibodies against Domain III of Dengue Virus Type 2 Envelope Protein Recognize Adjacent Epitopes," *J. Virol.*, vol. 81:12816-12826, 2007.

Tobin et al., "Deceptive Imprinting and Immune Refocusing in Vaccine Design," *Vaccine*, vol. 26:6189-6199, 2008.

Trainor et al., "Mutation Analysis of the Fusion Domain Region of St. Louis Encephalitis Virus Envelope Protein," *Virology*, vol. 360:398-406, 2007.

Supplementary Partial European Search Report for European Application No. 12841016, dated Jun. 9, 2015; 2 pages.

Lee et al., "Changes in the Dengue Virus Major Envelope Protein on Passaging and Their Localization on the Three-Dimensional Structure of the Protein," *Virol.*, vol. 232:281-290, 1997.

Lin et al., "The Helical Domains of the Stem Regions of Dengue Virus Envelope Protein are Involved in both Virus Assembly and Entry," *J. Virol.*, vol. 85:5159-5171, 2011.

Naïve 3 DPC pVD1-CRR 5 DPC pVD1-WT 5 DPC pVD1-WT 5 DPC

FIG. 4B

Uninfected pVD1-WT pVD1-CRR

Uninfected pVD1-WT pVD1-CRR

```
                        SEQUENCE LISTING

<160> NUMBER OF SEQ ID NOS: 19

<210> SEQ ID NO 1
<211> LENGTH: 495
<212> TYPE: PRT
<213> ORGANISM: Artificial Sequence
<220> FEATURE:
<223> OTHER INFORMATION: Synthetic polypeptide

<400> SEQUENCE: 1

Met Arg Cys Val Gly Ile Gly Ser Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ala Asn Phe Val Cys Arg Arg Thr Phe
                85                  90                  95

Val Asp Arg Gly Trp Gly Asn Gly Cys Arg Asp Phe Gly Lys Gly Ser
            100                 105                 110

Leu Ile Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
    130                 135                 140

Thr Gly Asp Gln His Gln Val Gly Asn Glu Ser Thr Glu His Gly Thr
145                 150                 155                 160

Thr Ala Thr Ile Thr Pro Gln Ala Pro Thr Thr Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Lys Glu Lys Ser Trp Leu Val
        195                 200                 205

His Lys Gln Trp Phe Leu Asp Leu Pro Leu Pro Trp Thr Ser Gly Ala
    210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
    290                 295                 300

Ser Phe Lys Leu Glu Asp Lys Val Ala Glu Thr Gln His Gly Thr Val
305                 310                 315                 320

Leu Val Gln Ile Lys Tyr Glu Gly Thr Asp Ala Pro Cys Lys Ile Pro
```

```
                          325                 330                 335
Phe Ser Thr Gln Asp Glu Lys Gly Val Thr Gln Asn Gly Arg Leu Ile
            340                 345                 350
Thr Ala Asn Pro Ile Val Thr Asp Lys Glu Lys Gln Val Asn Ile Glu
                355                 360                 365
Ala Glu Pro Pro Phe Gly Glu Ser Tyr Ile Val Ile Gly Ala Gly Glu
            370                 375                 380
Lys Ala Leu Lys Leu Ser Trp Phe Lys Lys Gly Ser Thr Leu Gly Lys
385                 390                 395                 400
Ala Phe Ser Thr Thr Leu Lys Gly Ala Gln Arg Leu Ala Ala Leu Gly
                405                 410                 415
Asp Thr Ala Trp Asp Phe Gly Ser Ile Gly Gly Val Phe Asn Ser Ile
            420                 425                 430
Gly Lys Ala Val His Gln Val Phe Gly Gly Ala Phe Arg Thr Leu Phe
                435                 440                 445
Gly Gly Met Ser Trp Ile Thr Gln Gly Leu Met Gly Ala Leu Leu Leu
            450                 455                 460
Trp Met Gly Ile Asn Ala Arg Asp Arg Ser Ile Ala Leu Thr Phe Leu
465                 470                 475                 480
Ala Val Gly Gly Val Leu Leu Phe Leu Ala Thr Asn Val His Ala
                485                 490                 495

<210> SEQ ID NO 2
<211> LENGTH: 495
<212> TYPE: PRT
<213> ORGANISM: Artificial Sequence
<220> FEATURE:
<223> OTHER INFORMATION: Synthetic polypeptide

<400> SEQUENCE: 2

Met Arg Cys Ile Gly Met Ser Asn Arg Asp Phe Val Glu Gly Val Ser
1               5                   10                  15
Gly Gly Ser Trp Val Asp Ile Val Leu Glu His Gly Ser Cys Val Thr
            20                  25                  30
Thr Met Ala Lys Asn Lys Pro Thr Leu Asp Phe Glu Leu Ile Lys Thr
        35                  40                  45
Glu Ala Lys Gln Pro Ala Thr Leu Arg Lys Tyr Cys Ile Glu Ala Lys
    50                  55                  60
Leu Thr Asn Thr Thr Thr Glu Ser Arg Cys Pro Thr Gln Gly Glu Pro
65                  70                  75                  80
Ser Leu Asn Glu Glu Gln Asp Lys Arg Phe Val Cys Lys His Ser Met
                85                  90                  95
Val Asp Arg Gly Trp Gly Asn Gly Cys Arg Asp Phe Gly Lys Gly Gly
            100                 105                 110
Ile Val Thr Cys Ala Met Phe Arg Cys Lys Lys Asn Met Glu Gly Lys
        115                 120                 125
Val Val Gln Pro Glu Asn Leu Glu Tyr Thr Ile Val Ile Thr Pro His
    130                 135                 140
Ser Gly Glu Glu His Ala Val Gly Asn Asp Thr Gly Lys His Gly Lys
145                 150                 155                 160
Glu Ile Lys Ile Thr Pro Gln Ser Ser Ile Thr Glu Ala Glu Leu Thr
                165                 170                 175
Gly Tyr Gly Thr Val Thr Met Glu Cys Ser Pro Arg Thr Gly Leu Asp
            180                 185                 190
Phe Asn Glu Met Val Leu Leu Gln Met Glu Asn Lys Ala Trp Leu Val
```

```
            195                 200                 205
His Arg Gln Trp Phe Leu Asp Leu Pro Leu Pro Trp Leu Pro Gly Ala
210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
290                 295                 300

Lys Phe Lys Val Val Glu Arg Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Arg Val Asn Ile Glu
        355                 360                 365

Ala Glu Pro Pro Phe Gly Asp Ser Tyr Ile Ile Gly Val Glu Pro
370                 375                 380

Gly Gln Leu Lys Leu Asn Trp Phe Lys Lys Gly Ser Thr Leu Gly Lys
385                 390                 395                 400

Ala Phe Ser Thr Thr Leu Lys Gly Ala Gln Arg Leu Ala Ala Leu Gly
                405                 410                 415

Asp Thr Ala Trp Asp Phe Gly Ser Ile Gly Gly Val Phe Asn Ser Ile
            420                 425                 430

Gly Lys Ala Val His Gln Val Phe Gly Gly Ala Phe Arg Thr Leu Phe
        435                 440                 445

Gly Gly Met Ser Trp Ile Thr Gln Gly Leu Met Gly Ala Leu Leu Leu
450                 455                 460

Trp Met Gly Ile Asn Ala Arg Asp Arg Ser Ile Ala Leu Thr Phe Leu
465                 470                 475                 480

Ala Val Gly Gly Val Leu Leu Phe Leu Ala Thr Asn Val His Ala
                485                 490                 495

<210> SEQ ID NO 3
<211> LENGTH: 493
<212> TYPE: PRT
<213> ORGANISM: Artificial Sequence
<220> FEATURE:
<223> OTHER INFORMATION: Synthetic polypeptide

<400> SEQUENCE: 3

Met Arg Cys Val Gly Val Gly Asn Arg Asp Phe Val Glu Gly Leu Ser
1               5                   10                  15

Gly Ala Thr Trp Val Asp Val Val Leu Glu His Gly Gly Cys Val Thr
            20                  25                  30

Thr Met Ala Lys Asn Lys Pro Thr Leu Asp Ile Glu Leu Gln Lys Thr
        35                  40                  45

Glu Ala Thr Gln Leu Ala Thr Leu Arg Lys Leu Cys Ile Glu Gly Lys
    50                  55                  60

Ile Thr Asn Ile Thr Thr Asp Ser Arg Cys Pro Thr Gln Gly Glu Ala
```

-continued

```
               65                  70                  75                  80
          Ile Leu Pro Glu Glu Gln Asp Gln Asn Tyr Val Cys Lys His Thr Tyr
                           85                  90                  95
          Val Asp Arg Gly Trp Gly Asn Gly Cys Asp Asp Phe Gly Lys Gly Ser
                          100                 105                 110
          Leu Val Thr Cys Ala Lys Phe Gln Cys Leu Glu Ser Ile Glu Gly Lys
                          115                 120                 125
          Val Val Gln His Glu Asn Leu Lys Tyr Thr Val Ile Ile Thr Val His
                          130                 135                 140
          Thr Gly Asp Gln His Gln Val Gly Asn Asp Thr Gln Gly Val Thr Val
          145                 150                 155                 160
          Glu Ile Thr Pro Gln Ala Ser Thr Val Glu Ala Ile Leu Pro Glu Tyr
                          165                 170                 175
          Gly Thr Leu Gly Leu Glu Cys Ser Pro Arg Thr Gly Leu Asp Phe Asn
                          180                 185                 190
          Glu Met Ile Leu Leu Thr Met Lys Asn Lys Ala Trp Met Val His Arg
                          195                 200                 205
          Gln Trp Phe Phe Asp Leu Pro Leu Pro Trp Thr Ser Gly Ala Thr Thr
                          210                 215                 220
          Glu Thr Pro Thr Trp Asn Arg Lys Glu Leu Leu Val Thr Phe Lys Asn
          225                 230                 235                 240
          Ala His Ala Lys Lys Gln Glu Val Val Val Leu Gly Ser Gln Glu Gly
                          245                 250                 255
          Ala Met His Thr Ala Leu Thr Gly Ala Thr Glu Ile Gln Asn Ser Gly
                          260                 265                 270
          Gly Thr Ser Ile Phe Ala Gly His Leu Lys Cys Arg Leu Lys Met Asp
                          275                 280                 285
          Lys Leu Glu Leu Lys Gly Met Ser Tyr Ala Met Cys Leu Asn Thr Phe
                          290                 295                 300
          Val Leu Lys Asp Lys Val Ser Glu Thr Gln His Gly Thr Ile Leu Ile
          305                 310                 315                 320
          Lys Val Glu Tyr Lys Gly Glu Asp Ala Pro Cys Lys Ile Pro Phe Ser
                          325                 330                 335
          Thr Glu Asp Gly Gln Gly Lys Ala His Asn Gly Arg Leu Ile Thr Ala
                          340                 345                 350
          Asn Pro Val Val Thr Lys Lys Glu Glu Asp Val Asn Ile Glu Ala Glu
                          355                 360                 365
          Pro Pro Phe Gly Glu Ser Asn Ile Val Ile Gly Ile Gly Asp Lys Ala
                          370                 375                 380
          Leu Lys Ile Asn Trp Tyr Lys Lys Gly Ser Thr Leu Gly Lys Ala Phe
          385                 390                 395                 400
          Ser Thr Thr Leu Lys Gly Ala Gln Arg Leu Ala Ala Leu Gly Asp Thr
                          405                 410                 415
          Ala Trp Asp Phe Gly Ser Ile Gly Gly Val Phe Asn Ser Ile Gly Lys
                          420                 425                 430
          Ala Val His Gln Val Phe Gly Gly Ala Phe Arg Thr Leu Phe Gly Gly
                          435                 440                 445
          Met Ser Trp Ile Thr Gln Gly Leu Met Gly Ala Leu Leu Leu Trp Met
                          450                 455                 460
          Gly Ile Asn Ala Arg Asp Arg Ser Ile Ala Leu Thr Phe Leu Ala Val
          465                 470                 475                 480
          Gly Gly Val Leu Leu Phe Leu Ala Thr Asn Val His Ala
                          485                 490
```

<210> SEQ ID NO 4
<211> LENGTH: 495
<212> TYPE: PRT
<213> ORGANISM: Artificial Sequence
<220> FEATURE:
<223> OTHER INFORMATION: Synthetic polypeptide

<400> SEQUENCE: 4

```
Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20                  25                  30

Thr Met Ala Gln Gly Lys Pro Thr Leu Asp Phe Glu Leu Ile Lys Thr
        35                  40                  45

Thr Ala Lys Glu Val Ala Leu Leu Arg Thr Tyr Cys Ile Glu Ala Ser
    50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Tyr Ile Cys Arg Arg Asp Val
                85                  90                  95

Val Asp Arg Gly Trp Gly Asn Gly Cys Glu Asp Phe Gly Lys Gly Gly
            100                 105                 110

Val Val Thr Cys Ala Lys Phe Ser Cys Ser Gly Lys Ile Thr Gly Asn
        115                 120                 125

Leu Val Gln Ile Glu Asn Leu Glu Tyr Thr Val Val Thr Val His
    130                 135                 140

Asn Gly Asp Thr His Ala Val Gly Asn Asp Thr Ser Asn His Gly Val
145                 150                 155                 160

Thr Ala Thr Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
            180                 185                 190

Phe Asn Glu Met Ile Leu Met Lys Met Lys Lys Thr Trp Leu Val
        195                 200                 205

His Lys Gln Trp Phe Leu Asp Leu Pro Leu Pro Trp Thr Ala Gly Ala
    210                 215                 220

Asp Thr Ser Glu Val His Trp Asn His Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Thr Gly Ala Thr Glu Val Asp Ser
            260                 265                 270

Gly Asp Gly Asn His Met Phe Ala Gly His Leu Lys Cys Lys Val Arg
        275                 280                 285

Met Glu Lys Leu Arg Ile Lys Gly Met Ser Tyr Thr Met Cys Ser Gly
    290                 295                 300

Lys Phe Ser Ile Asp Asp Gln Met Ala Glu Thr Gln His Gly Thr Thr
305                 310                 315                 320

Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Ile Ile
            340                 345                 350

Ser Ser Thr Pro Phe Ala Glu Asn Thr Asn Ser Val Thr Asn Ile Glu
        355                 360                 365
```

-continued

Leu Glu Pro Pro Phe Gly Asp Ser Tyr Ile Val Ile Gly Val Gly Asp
    370                 375                 380

Ser Ala Leu Thr Gln His Trp Phe Arg Lys Gly Ser Thr Leu Gly Lys
385                 390                 395                 400

Ala Phe Ser Thr Thr Leu Lys Gly Ala Gln Arg Leu Ala Ala Leu Gly
                405                 410                 415

Asp Thr Ala Trp Asp Phe Gly Ser Ile Gly Gly Val Phe Asn Ser Ile
            420                 425                 430

Gly Lys Ala Val His Gln Val Phe Gly Gly Ala Phe Arg Thr Leu Phe
        435                 440                 445

Gly Gly Met Ser Trp Ile Thr Gln Gly Leu Met Gly Ala Leu Leu Leu
    450                 455                 460

Trp Met Gly Ile Asn Ala Arg Asp Arg Ser Ile Ala Leu Thr Phe Leu
465                 470                 475                 480

Ala Val Gly Gly Val Leu Leu Phe Leu Ala Thr Asn Val His Ala
                485                 490                 495

<210> SEQ ID NO 5
<211> LENGTH: 685
<212> TYPE: PRT
<213> ORGANISM: Artificial Sequence
<220> FEATURE:
<223> OTHER INFORMATION: Synthetic polypeptide

<400> SEQUENCE: 5

Met Gly Lys Arg Ser Ala Gly Ser Ile Met Trp Leu Ala Ser Leu Ala
1               5                   10                  15

Val Val Ile Ala Gly Thr Ser Ala Phe His Leu Thr Thr Arg Gly Gly
                20                  25                  30

Glu Pro His Met Ile Val Ser Lys Gln Glu Arg Gly Lys Ser Leu Leu
            35                  40                  45

Phe Lys Thr Ser Ala Gly Val Asn Met Cys Thr Leu Ile Ala Met Asp
    50                  55                  60

Leu Gly Glu Leu Cys Glu Asp Thr Met Thr Tyr Lys Cys Pro Arg Ile
65                  70                  75                  80

Thr Glu Ala Glu Pro Asp Asp Val Asp Cys Trp Cys Asn Ala Thr Asp
                85                  90                  95

Thr Trp Val Thr Tyr Gly Thr Cys Ser Gln Thr Gly Glu His Arg Arg
            100                 105                 110

Asp Lys Arg Ser Val Ala Leu Ala Pro His Val Gly Leu Gly Leu Glu
    115                 120                 125

Thr Arg Thr Glu Thr Trp Met Ser Ser Glu Gly Ala Trp Lys Gln Ile
130                 135                 140

Gln Arg Val Glu Thr Trp Ala Leu Arg His Pro Gly Phe Thr Val Ile
145                 150                 155                 160

Ala Leu Phe Leu Ala His Ala Ile Gly Thr Ser Ile Thr Gln Lys Gly
                165                 170                 175

Ile Ile Phe Ile Leu Leu Met Leu Val Thr Pro Ser Met Ala Met Arg
            180                 185                 190

Cys Val Gly Ile Gly Ser Arg Asp Phe Val Glu Gly Leu Ser Gly Ala
    195                 200                 205

Thr Trp Val Asp Val Val Leu Glu His Gly Ser Cys Val Thr Thr Met
210                 215                 220

Ala Lys Asp Lys Pro Thr Leu Asp Ile Glu Leu Leu Lys Thr Glu Val
225                 230                 235                 240

```
Thr Asn Pro Ala Val Leu Arg Lys Leu Cys Ile Glu Ala Lys Ile Ser
                245                 250                 255

Asn Thr Thr Thr Asp Ser Arg Cys Pro Thr Gln Gly Glu Ala Thr Leu
            260                 265                 270

Val Glu Glu Gln Asp Ala Asn Phe Val Cys Arg Arg Thr Phe Val Asp
        275                 280                 285

Arg Gly Trp Gly Asn Gly Cys Arg Asp Phe Gly Lys Gly Ser Leu Ile
    290                 295                 300

Thr Cys Ala Lys Phe Lys Cys Val Thr Lys Leu Glu Gly Lys Ile Val
305                 310                 315                 320

Gln Tyr Glu Asn Leu Lys Tyr Ser Val Ile Val Thr Val His Thr Gly
                325                 330                 335

Asp Gln His Gln Val Gly Asn Glu Ser Thr Glu His Gly Thr Thr Ala
            340                 345                 350

Thr Ile Thr Pro Gln Ala Pro Thr Thr Glu Ile Gln Leu Thr Asp Tyr
        355                 360                 365

Gly Ala Leu Thr Leu Asp Cys Ser Pro Arg Thr Gly Leu Asp Phe Asn
    370                 375                 380

Glu Met Val Leu Leu Thr Met Lys Glu Lys Ser Trp Leu Val His Lys
385                 390                 395                 400

Gln Trp Phe Leu Asp Leu Pro Leu Pro Trp Thr Ser Gly Ala Ser Thr
                405                 410                 415

Ser Gln Glu Thr Trp Asn Arg Gln Asp Leu Leu Val Thr Phe Lys Thr
            420                 425                 430

Ala His Ala Lys Lys Gln Glu Val Val Leu Gly Ser Gln Glu Gly
        435                 440                 445

Ala Met His Thr Ala Leu Thr Gly Ala Thr Glu Ile Gln Thr Ser Gly
    450                 455                 460

Thr Thr Thr Ile Phe Ala Gly His Leu Lys Cys Arg Leu Lys Met Asp
465                 470                 475                 480

Lys Leu Thr Leu Lys Gly Met Ser Tyr Val Met Cys Thr Gly Ser Phe
                485                 490                 495

Lys Leu Glu Asp Lys Val Ala Glu Thr Gln His Gly Thr Val Leu Val
            500                 505                 510

Gln Ile Lys Tyr Glu Gly Thr Asp Ala Pro Cys Lys Ile Pro Phe Ser
        515                 520                 525

Thr Gln Asp Glu Lys Gly Val Thr Gln Asn Gly Arg Leu Ile Thr Ala
    530                 535                 540

Asn Pro Ile Val Thr Asp Lys Glu Lys Gln Val Asn Ile Glu Ala Glu
545                 550                 555                 560

Pro Pro Phe Gly Glu Ser Tyr Ile Val Ile Gly Ala Gly Glu Lys Ala
                565                 570                 575

Leu Lys Leu Ser Trp Phe Lys Lys Gly Ser Thr Leu Gly Lys Ala Phe
            580                 585                 590

Ser Thr Thr Leu Lys Gly Ala Gln Arg Leu Ala Ala Leu Gly Asp Thr
        595                 600                 605

Ala Trp Asp Phe Gly Ser Ile Gly Gly Val Phe Asn Ser Ile Gly Lys
    610                 615                 620

Ala Val His Gln Val Phe Gly Gly Ala Phe Arg Thr Leu Phe Gly Gly
625                 630                 635                 640

Met Ser Trp Ile Thr Gln Gly Leu Met Gly Ala Leu Leu Leu Trp Met
                645                 650                 655
```

```
Gly Ile Asn Ala Arg Asp Arg Ser Ile Ala Leu Thr Phe Leu Ala Val
            660                 665                 670

Gly Gly Val Leu Leu Phe Leu Ala Thr Asn Val His Ala
        675                 680                 685

<210> SEQ ID NO 6
<211> LENGTH: 685
<212> TYPE: PRT
<213> ORGANISM: Artificial Sequence
<220> FEATURE:
<223> OTHER INFORMATION: Synthetic polypeptide

<400> SEQUENCE: 6

Met Gly Lys Arg Ser Ala Gly Ser Ile Met Trp Leu Ala Ser Leu Ala
1               5                   10                  15

Val Val Ile Ala Cys Ala Gly Ala Phe His Leu Thr Thr Arg Asn Gly
            20                  25                  30

Glu Pro His Met Ile Val Ser Arg Gln Glu Lys Gly Lys Ser Leu Leu
        35                  40                  45

Phe Lys Thr Glu Asp Gly Val Asn Met Cys Thr Leu Met Ala Met Asp
    50                  55                  60

Leu Gly Glu Leu Cys Glu Asp Thr Ile Thr Tyr Lys Cys Pro Leu Leu
65                  70                  75                  80

Arg Gln Asn Glu Pro Glu Asp Ile Asp Cys Trp Cys Asn Ser Thr Ser
                85                  90                  95

Thr Trp Val Thr Tyr Gly Thr Cys Thr Thr Met Gly Glu His Arg Arg
            100                 105                 110

Glu Lys Arg Ser Val Ala Leu Val Pro His Val Gly Met Gly Leu Glu
        115                 120                 125

Thr Arg Thr Glu Thr Trp Met Ser Ser Glu Gly Ala Trp Lys His Val
    130                 135                 140

Gln Arg Ile Glu Thr Trp Ile Leu Arg His Pro Gly Phe Thr Met Met
145                 150                 155                 160

Ala Ala Ile Leu Ala Tyr Thr Ile Gly Thr Thr His Phe Gln Arg Ala
                165                 170                 175

Leu Ile Phe Ile Leu Leu Thr Ala Val Thr Pro Ser Met Thr Met Arg
            180                 185                 190

Cys Ile Gly Met Ser Asn Arg Asp Phe Val Glu Gly Val Ser Gly Gly
        195                 200                 205

Ser Trp Val Asp Ile Val Leu Glu His Gly Ser Cys Val Thr Thr Met
    210                 215                 220

Ala Lys Asn Lys Pro Thr Leu Asp Phe Glu Leu Ile Lys Thr Glu Ala
225                 230                 235                 240

Lys Gln Pro Ala Thr Leu Arg Lys Tyr Cys Ile Glu Ala Lys Leu Thr
                245                 250                 255

Asn Thr Thr Thr Glu Ser Arg Cys Pro Thr Gln Gly Glu Pro Ser Leu
            260                 265                 270

Asn Glu Glu Gln Asp Lys Arg Phe Val Cys Lys His Ser Met Val Asp
        275                 280                 285

Arg Gly Trp Gly Asn Gly Cys Arg Asp Phe Gly Lys Gly Ile Val
    290                 295                 300

Thr Cys Ala Met Phe Arg Cys Lys Lys Asn Met Glu Gly Lys Val Val
305                 310                 315                 320

Gln Pro Glu Asn Leu Glu Tyr Thr Ile Val Ile Thr Pro His Ser Gly
                325                 330                 335
```

```
Glu Glu His Ala Val Gly Asn Asp Thr Gly Lys His Gly Lys Glu Ile
                340                 345                 350

Lys Ile Thr Pro Gln Ser Ser Ile Thr Glu Ala Glu Leu Thr Gly Tyr
            355                 360                 365

Gly Thr Val Thr Met Glu Cys Ser Pro Arg Thr Gly Leu Asp Phe Asn
        370                 375                 380

Glu Met Val Leu Leu Gln Met Glu Asn Lys Ala Trp Leu Val His Arg
385                 390                 395                 400

Gln Trp Phe Leu Asp Leu Pro Leu Pro Trp Leu Pro Gly Ala Asp Thr
                405                 410                 415

Gln Gly Ser Asn Trp Ile Gln Lys Glu Thr Leu Val Thr Phe Lys Asn
            420                 425                 430

Pro His Ala Lys Lys Gln Asp Val Val Leu Gly Ser Gln Glu Gly
        435                 440                 445

Ala Met His Thr Ala Leu Thr Gly Ala Thr Glu Ile Gln Met Ser Ser
    450                 455                 460

Gly Asn Leu Leu Phe Thr Gly His Leu Lys Cys Arg Leu Arg Met Asp
465                 470                 475                 480

Lys Leu Gln Leu Lys Gly Met Ser Tyr Ser Met Cys Thr Gly Lys Phe
                485                 490                 495

Lys Val Val Glu Arg Ile Ala Glu Thr Gln His Gly Thr Ile Val Ile
            500                 505                 510

Arg Val Gln Tyr Glu Gly Asp Gly Ser Pro Cys Lys Ile Pro Phe Glu
        515                 520                 525

Ile Met Asp Leu Glu Lys Arg His Val Leu Gly Arg Leu Ile Thr Val
    530                 535                 540

Asn Pro Ile Val Thr Glu Lys Asp Ser Arg Val Asn Ile Glu Ala Glu
545                 550                 555                 560

Pro Pro Phe Gly Asp Ser Tyr Ile Ile Ile Gly Val Glu Pro Gly Gln
                565                 570                 575

Leu Lys Leu Asn Trp Phe Lys Lys Gly Ser Thr Leu Gly Lys Ala Phe
            580                 585                 590

Ser Thr Thr Leu Lys Gly Ala Gln Arg Leu Ala Ala Leu Gly Asp Thr
        595                 600                 605

Ala Trp Asp Phe Gly Ser Ile Gly Gly Val Phe Asn Ser Ile Gly Lys
    610                 615                 620

Ala Val His Gln Val Phe Gly Gly Ala Phe Arg Thr Leu Phe Gly Gly
625                 630                 635                 640

Met Ser Trp Ile Thr Gln Gly Leu Met Gly Ala Leu Leu Leu Trp Met
                645                 650                 655

Gly Ile Asn Ala Arg Asp Arg Ser Ile Ala Leu Thr Phe Leu Ala Val
            660                 665                 670

Gly Gly Val Leu Leu Phe Leu Ala Thr Asn Val His Ala
        675                 680                 685

<210> SEQ ID NO 7
<211> LENGTH: 683
<212> TYPE: PRT
<213> ORGANISM: Artificial Sequence
<220> FEATURE:
<223> OTHER INFORMATION: Synthetic polypeptide

<400> SEQUENCE: 7

Met Gly Lys Arg Ser Ala Gly Ser Ile Met Trp Leu Ala Ser Leu Ala
1               5                   10                  15
```

```
Val Val Ile Ala Gly Thr Ser Ala Phe His Leu Thr Ser Arg Asp Gly
             20                  25                  30

Glu Pro Arg Met Ile Val Gly Lys Asn Glu Arg Gly Lys Ser Leu Leu
         35                  40                  45

Phe Lys Thr Ala Ser Gly Ile Asn Met Cys Thr Leu Ile Ala Met Asp
 50                  55                  60

Leu Gly Glu Met Cys Asp Asp Thr Val Thr Tyr Lys Cys Pro Leu Ile
 65                  70                  75                  80

Ala Glu Val Glu Pro Glu Asp Ile Asp Cys Trp Cys Asn Leu Thr Ser
                 85                  90                  95

Thr Trp Val Thr Tyr Gly Thr Cys Asn Gln Ala Gly Glu His Arg Arg
                100                 105                 110

Asp Lys Arg Ser Val Ala Leu Ala Pro His Val Gly Met Gly Leu Asp
            115                 120                 125

Thr Arg Thr Gln Thr Trp Met Ser Ala Glu Gly Ala Trp Arg Gln Val
        130                 135                 140

Glu Lys Val Glu Thr Trp Ala Leu Arg His Pro Gly Phe Thr Ile Leu
145                 150                 155                 160

Ala Leu Phe Leu Ala His Tyr Ile Gly Thr Ser Leu Thr Gln Lys Val
                165                 170                 175

Val Ile Phe Ile Leu Leu Met Leu Val Thr Pro Ser Met Ala Met Arg
                180                 185                 190

Cys Val Gly Val Gly Asn Arg Asp Phe Val Glu Gly Leu Ser Gly Ala
            195                 200                 205

Thr Trp Val Asp Val Val Leu Glu His Gly Gly Cys Val Thr Thr Met
        210                 215                 220

Ala Lys Asn Lys Pro Thr Leu Asp Ile Glu Leu Gln Lys Thr Glu Ala
225                 230                 235                 240

Thr Gln Leu Ala Thr Leu Arg Lys Leu Cys Ile Glu Gly Lys Ile Thr
                245                 250                 255

Asn Ile Thr Thr Asp Ser Arg Cys Pro Thr Gln Gly Glu Ala Ile Leu
                260                 265                 270

Pro Glu Glu Gln Asp Gln Asn Tyr Val Cys Lys His Thr Tyr Val Asp
        275                 280                 285

Arg Gly Trp Gly Asn Gly Cys Asp Asp Phe Gly Lys Gly Ser Leu Val
    290                 295                 300

Thr Cys Ala Lys Phe Gln Cys Leu Glu Ser Ile Glu Gly Lys Val Val
305                 310                 315                 320

Gln His Glu Asn Leu Lys Tyr Thr Val Ile Ile Thr Val His Thr Gly
                325                 330                 335

Asp Gln His Gln Val Gly Asn Asp Thr Gln Gly Val Thr Val Glu Ile
            340                 345                 350

Thr Pro Gln Ala Ser Thr Val Glu Ala Ile Leu Pro Glu Tyr Gly Thr
        355                 360                 365

Leu Gly Leu Glu Cys Ser Pro Arg Thr Gly Leu Asp Phe Asn Glu Met
    370                 375                 380

Ile Leu Leu Thr Met Lys Asn Lys Ala Trp Met Val His Arg Gln Trp
385                 390                 395                 400

Phe Phe Asp Leu Pro Leu Pro Trp Thr Ser Gly Ala Thr Thr Glu Thr
                405                 410                 415

Pro Thr Trp Asn Arg Lys Glu Leu Leu Val Thr Phe Lys Asn Ala His
        420                 425                 430

Ala Lys Lys Gln Glu Val Val Val Leu Gly Ser Gln Glu Gly Ala Met
```

```
            435                 440                 445
    His Thr Ala Leu Thr Gly Ala Thr Glu Ile Gln Asn Ser Gly Gly Thr
        450                 455                 460
    Ser Ile Phe Ala Gly His Leu Lys Cys Arg Leu Lys Met Asp Lys Leu
    465                 470                 475                 480
    Glu Leu Lys Gly Met Ser Tyr Ala Met Cys Leu Asn Thr Phe Val Leu
                    485                 490                 495
    Lys Asp Lys Val Ser Glu Thr Gln His Gly Thr Ile Leu Ile Lys Val
                500                 505                 510
    Glu Tyr Lys Gly Glu Asp Ala Pro Cys Lys Ile Pro Phe Ser Thr Glu
                515                 520                 525
    Asp Gly Gln Gly Lys Ala His Asn Gly Arg Leu Ile Thr Ala Asn Pro
                530                 535                 540
    Val Val Thr Lys Lys Glu Glu Asp Val Asn Ile Glu Ala Glu Pro Pro
    545                 550                 555                 560
    Phe Gly Glu Ser Asn Ile Val Ile Gly Ile Gly Asp Lys Ala Leu Lys
                    565                 570                 575
    Ile Asn Trp Tyr Lys Lys Gly Ser Thr Leu Gly Lys Ala Phe Ser Thr
                    580                 585                 590
    Thr Leu Lys Gly Ala Gln Arg Leu Ala Ala Leu Gly Asp Thr Ala Trp
                    595                 600                 605
    Asp Phe Gly Ser Ile Gly Gly Val Phe Asn Ser Ile Gly Lys Ala Val
                610                 615                 620
    His Gln Val Phe Gly Gly Ala Phe Arg Thr Leu Phe Gly Gly Met Ser
    625                 630                 635                 640
    Trp Ile Thr Gln Gly Leu Met Gly Ala Leu Leu Leu Trp Met Gly Ile
                        645                 650                 655
    Asn Ala Arg Asp Arg Ser Ile Ala Leu Thr Phe Leu Ala Val Gly Gly
                    660                 665                 670
    Val Leu Leu Phe Leu Ala Thr Asn Val His Ala
                    675                 680

<210> SEQ ID NO 8
<211> LENGTH: 685
<212> TYPE: PRT
<213> ORGANISM: Artificial Sequence
<220> FEATURE:
<223> OTHER INFORMATION: Synthetic polypeptide

<400> SEQUENCE: 8

Met Gly Lys Arg Ser Ala Gly Ser Ile Met Trp Leu Ala Ser Leu Ala
    1               5                   10                  15
    Val Val Ile Ala Gly Thr Ser Ala Phe Ser Leu Ser Thr Arg Asp Gly
                    20                  25                  30
    Glu Pro Leu Met Ile Val Ala Lys His Glu Arg Gly Arg Pro Leu Leu
                35                  40                  45
    Phe Lys Thr Thr Glu Gly Ile Asn Lys Cys Thr Leu Ile Ala Met Asp
            50                  55                  60
    Leu Gly Glu Met Cys Glu Asp Thr Val Thr Tyr Lys Cys Pro Leu Leu
    65                  70                  75                  80
    Val Asn Thr Glu Pro Glu Asp Ile Asp Cys Trp Cys Asn Leu Thr Ser
                    85                  90                  95
    Ala Trp Val Met Tyr Gly Thr Cys Thr Gln Ser Gly Glu Arg Arg Arg
                    100                 105                 110
    Glu Lys Arg Ser Val Ala Leu Thr Pro His Ser Gly Met Gly Leu Glu
```

```
                        115                 120                 125
Thr Arg Ala Glu Thr Trp Met Ser Ser Glu Gly Ala Trp Lys His Ala
        130                 135                 140

Gln Arg Val Glu Ser Trp Ile Leu Arg Asn Pro Gly Phe Ala Leu Leu
145                 150                 155                 160

Ala Gly Phe Met Ala Tyr Met Ile Gly Thr Gly Ile Gln Arg Thr
                    165                 170                 175

Val Phe Phe Ile Leu Met Met Leu Val Ala Pro Ser Tyr Gly Met Arg
                180                 185                 190

Cys Val Gly Val Gly Asn Arg Asp Phe Val Glu Gly Val Ser Gly Gly
                195                 200                 205

Ala Trp Val Asp Leu Val Leu Glu His Gly Gly Cys Val Thr Thr Met
210                 215                 220

Ala Gln Gly Lys Pro Thr Leu Asp Phe Glu Leu Ile Lys Thr Thr Ala
225                 230                 235                 240

Lys Glu Val Ala Leu Leu Arg Thr Tyr Cys Ile Glu Ala Ser Ile Ser
                245                 250                 255

Asn Ile Thr Thr Ala Thr Arg Cys Pro Thr Gln Gly Glu Pro Tyr Leu
                260                 265                 270

Lys Glu Glu Gln Asp Gln Gln Tyr Ile Cys Arg Arg Asp Val Val Asp
                275                 280                 285

Arg Gly Trp Gly Asn Gly Cys Glu Asp Phe Gly Lys Gly Gly Val Val
290                 295                 300

Thr Cys Ala Lys Phe Ser Cys Ser Gly Lys Ile Thr Gly Asn Leu Val
305                 310                 315                 320

Gln Ile Glu Asn Leu Glu Tyr Thr Val Val Thr Val His Asn Gly
                325                 330                 335

Asp Thr His Ala Val Gly Asn Asp Thr Ser Asn His Gly Val Thr Ala
                340                 345                 350

Thr Ile Thr Pro Arg Ser Pro Ser Val Glu Val Lys Leu Pro Asp Tyr
                355                 360                 365

Gly Glu Leu Thr Leu Asp Cys Glu Pro Arg Ser Gly Ile Asp Phe Asn
                370                 375                 380

Glu Met Ile Leu Met Lys Met Lys Lys Thr Trp Leu Val His Lys
385                 390                 395                 400

Gln Trp Phe Leu Asp Leu Pro Leu Pro Trp Thr Ala Gly Ala Asp Thr
                405                 410                 415

Ser Glu Val His Trp Asn His Lys Glu Arg Met Val Thr Phe Lys Val
                420                 425                 430

Pro His Ala Lys Arg Gln Asp Val Thr Val Leu Gly Ser Gln Glu Gly
                435                 440                 445

Ala Met His Ser Ala Leu Thr Gly Ala Thr Glu Val Asp Ser Gly Asp
                450                 455                 460

Gly Asn His Met Phe Ala Gly His Leu Lys Cys Lys Val Arg Met Glu
465                 470                 475                 480

Lys Leu Arg Ile Lys Gly Met Ser Tyr Thr Met Cys Ser Gly Lys Phe
                485                 490                 495

Ser Ile Asp Asp Gln Met Ala Glu Thr Gln His Gly Thr Thr Val Val
                500                 505                 510

Lys Val Lys Tyr Glu Gly Ala Gly Ala Pro Cys Lys Val Pro Ile Glu
                515                 520                 525

Ile Arg Asp Val Asn Lys Glu Lys Val Val Gly Arg Ile Ile Ser Ser
530                 535                 540
```

Thr Pro Phe Ala Glu Asn Thr Asn Ser Val Thr Asn Ile Glu Leu Glu
545                 550                 555                 560

Pro Pro Phe Gly Asp Ser Tyr Ile Val Ile Gly Val Gly Asp Ser Ala
            565                 570                 575

Leu Thr Gln His Trp Phe Arg Lys Gly Ser Thr Leu Gly Lys Ala Phe
                580                 585                 590

Ser Thr Thr Leu Lys Gly Ala Gln Arg Leu Ala Ala Leu Gly Asp Thr
            595                 600                 605

Ala Trp Asp Phe Gly Ser Ile Gly Gly Val Phe Asn Ser Ile Gly Lys
610                 615                 620

Ala Val His Gln Val Phe Gly Ala Phe Arg Thr Leu Phe Gly Gly
625                 630                 635                 640

Met Ser Trp Ile Thr Gln Gly Leu Met Gly Ala Leu Leu Leu Trp Met
                645                 650                 655

Gly Ile Asn Ala Arg Asp Arg Ser Ile Ala Leu Thr Phe Leu Ala Val
            660                 665                 670

Gly Gly Val Leu Leu Phe Leu Ala Thr Asn Val His Ala
            675                 680                 685

<210> SEQ ID NO 9
<211> LENGTH: 5180
<212> TYPE: DNA
<213> ORGANISM: Artificial Sequence
<220> FEATURE:
<223> OTHER INFORMATION: Synthetic construct

<400> SEQUENCE: 9
gactcttcgc gatgtacggg ccagatatac gcgttgacat tgattattga ctagttatta      60
atagtaatca attacggggt cattagttca tagcccatat atggagttcc gcgttacata     120
acttacggta aatggcccgc ctggctgacc gcccaacgac ccccgcccat tgacgtcaat     180
aatgacgtat gttcccatag taacgccaat agggactttc cattgacgtc aatgggtgga     240
gtatttacgg taaactgccc acttggcagt acatcaagtg tatcatatgc caagtacgcc     300
ccctattgac gtcaatgacg gtaaatggcc cgcctggcat tatgcccagt acatgacctt     360
atgggacttt cctacttggc agtacatcta cgtattagtc atcgctatta ccatggtgat     420
gcggttttgg cagtacatca atgggcgtgg atagcggttt gactcacggg gatttccaag     480
tctccacccc attgacgtca atgggagttt gttttggcac caaaatcaac gggactttcc     540
aaaatgtcgt aacaactccg ccccattgac gcaaatgggc ggtaggcgtg tacggtggga     600
ggtctatata agcagagctc tctggctaac tagagaaccc actgcttact ggcttatcga     660
aattaatacg actcactata gggagaccca agctggctag cgtttaaact taagcttggt     720
accgccgccg ccatgggcaa gaggtccgcc ggctcaatca tgtggctcgc gagcttggca     780
gttgtcatag ctggtacaag cgcttttcca ctgaccaccc gaggggggaga gccgcacatg     840 atagtcagca agcaggaaag aggaaagtca cttttgttta agacctcagc aggtgtcaac     900
atgtgcaccc ttatagcgat ggatttggga gagttatgtg aggacacaat gacttacaaa    960
tgccctcgaa tcactgaggc ggaaccagat gacgttgatt gttggtgcaa tgccacagac    1020
acatgggtga cctatggaac atgttcccaa actggcgagc accgacgaga caaacgttcc    1080
gtcgcactgg ccccacacgt gggacttggt ttggaaacaa gaaccgaaac gtggatgtcc    1140
tctgaaggcg cttggaaaca gatacaaaga gtggagactt gggcccctga gacacccaga    1200
ttcacggtga tagcccttttt tctagcacat gccataggaa catccatcac ccagaaaggg    1260

```
attattttca ttttgttaat gctggtaaca ccatccatgg ccatgcgatg cgtgggaata    1320
ggcagcaggg acttcgtgga aggactgtca ggagcaactt gggtagatgt ggtactggaa    1380
catggaagtt gcgtcaccac catggcaaaa gacaaaccaa cattggacat tgaactcttg    1440
aagacggaag tcacaaaccc tgccgtcctg cgcaaactgt gcattgaagc taaaatatca    1500
aacaccacca ccgactcaag atgtccaaca caaggagaag ccacactggt ggaagaacaa    1560
gacgcgaact ttgtgtgtcg acgaacgttt gtggacagag gctggggcaa tggctgtcgg    1620
gatttcggaa aaggaagcct aataacgtgt gctaagttca agtgtgtgac aaaactggaa    1680
ggaaagatag ttcaatatga aaacttgaaa tattcagtaa tagtcaccgt ccacactgga    1740
gaccagcacc aggtgggaaa tgaaagcaca gaacatggga caactgcaac tataacacct    1800
caagctccta cgacggaaat acagctgacc gactacggag ctcttacatt ggattgttca    1860
cctagaacag gactagactt taatgaaatg gtgttgttga caatgaaaga aaaatcatgg    1920
ctagttcaca acaatggtt tctagaccta ccactgcctt ggacctcggg agcttcaaca    1980
tcacaagaga cttggaacag acaagatttg ctggtgacat tcaagacagc tcatgcaaag    2040
aagcaggaag tagtcgtact aggatcacaa gaaggagcaa tgcacactgc gttgaccgga    2100
gcgacagaaa tccaaacgtc tggaacgaca acaattttg caggacactt gaaatgtaga    2160
ctaaagatgg acaaactgac tctaaaaggg atgtcatatg tgatgtgcac aggctcattc    2220
aagctagagg acaaggtggc tgagacccag catggaaccg ttctagtgca gattaaatac    2280
gaaggaacag atgcaccatg caagatccct ttttcgaccc aagatgaaaa aggagtaacc    2340
cagaatggga gattgataac agctaacccc atagtcactg acaaagaaaa acaggtcaac    2400
attgaggcag aaccgccttt tggtgagagt tacatcgtga taggagcagg tgaaaaagct    2460
ttgaaactaa gctggttcaa gaaggaagc acgctgggca aggccttttc aacaactttg    2520
aagggagcgt aagtatcaag gttacaagac aggtttaagg agaccaatag aaactgggct    2580
tttcgtgtcc ttcaactgca gtgtccttca acgaaacaga gaagactctt gcgtttctga    2640
taggcaccta ttggtcttac tgacatccac tttgccttc tctccacagt caaagactgg    2700
cagcgttggg cgacacagcc tgggactttg gctctattgg aggggtcttc aactccatag    2760
gaaaagccgt tcaccaagtg tttggtggtg ccttcagaac actctttggg ggaatgtctt    2820
ggatcacaca agggctaatg ggtgccctac tgctctggat gggcataaac gcacgagacc    2880
gatcaattgc tttgaccttc ttagccgtag ggggtgtgct cctgttctta gcgaccaatg    2940
tgcatgctta attagtttga gcggccgctc gagtctagag ggcccgttta aacccgctga    3000
tcagcctcga ctgtgccttc tagttgccag ccatctgttg tttgcccctc cccgtgcct    3060 tccttgaccc tggaaggtgc cactcccact gtcctttcct aataaaatga ggaaattgca    3120
tcgcattgtc tgagtaggtg tcattctatt ctggggggtg gggtggggca ggacagcaag    3180
ggggaggatt gggaagacaa tagcaggcat gctgggatg cggtgggctc tatggcttct    3240
actgggcggt tttatggaca gcaagcgaac cggaattgcc agctggggcg ccctctggta    3300
aggttgggaa gccctgcaaa gtaaactgga tggctttctc gccgccaagg atctgatggc    3360
gcaggggatc aagctctgat caagagacag gatgaggatc gtttcgcatg attgaacaag    3420
atggattgca cgcaggttct ccggccgctt gggtggagag gctattcggc tatgactggg    3480
cacaacagac aatcggctgc tctgatgccg ccgtgttccg gctgtcagcg caggggcgcc    3540
cggttctttt tgtcaagacc gacctgtccg gtgccctgaa tgaactgcaa gacgaggcag    3600
```

| | |
|---|---|
| cgcggctatc gtggctggcc acgacgggcg ttccttgcgc agctgtgctc gacgttgtca | 3660 |
| ctgaagcggg aagggactgg ctgctattgg gcgaagtgcc ggggcaggat ctcctgtcat | 3720 |
| ctcaccttgc tcctgccgag aaagtatcca tcatggctga tgcaatgcgg cggctgcata | 3780 |
| cgcttgatcc ggctacctgc ccattcgacc accaagcgaa acatcgcatc gagcgagcac | 3840 |
| gtactcggat ggaagccggt cttgtcgatc aggatgatct ggacgaagag catcaggggc | 3900 |
| tcgcgccagc cgaactgttc gccaggctca aggcgagcat gcccgacggc gaggatctcg | 3960 |
| tcgtgaccca tggcgatgcc tgcttgccga atatcatggt ggaaaatggc cgcttttctg | 4020 |
| gattcatcga ctgtggccgg ctgggtgtgg cggaccgcta tcaggacata gcgttggcta | 4080 |
| cccgtgatat tgctgaagag cttggcggcg aatgggctga ccgcttcctc gtgctttacg | 4140 |
| gtatcgccgc tcccgattcg cagcgcatcg ccttctatcg ccttcttgac gagttcttct | 4200 |
| gaattattaa cgcttacaat ttcctgatgc ggtattttct ccttacgcat ctgtgcggta | 4260 |
| tttcacaccg catacaggtg gcacttttcg gggaaatgtg cgcggaaccc ctatttgttt | 4320 |
| attttttctaa atacattcaa atatgtatcc gctcatgaga caataaccct gataaatgct | 4380 |
| tcaataatag cacgtgctaa aacttcattt ttaatttaaa aggatctagg tgaagatcct | 4440 |
| ttttgataat ctcatgacca aaatccctta acgtgagttt tcgttccact gagcgtcaga | 4500 |
| ccccgtagaa aagatcaaag gatcttcttg agatcctttt tttctgcgcg taatctgctg | 4560 |
| cttgcaaaca aaaaaaccac cgctaccagc ggtggtttgt ttgccggatc aagagctacc | 4620 |
| aactcttttt ccgaaggtaa ctggcttcag cagagcgcag ataccaaata ctgtccttct | 4680 |
| agtgtagccg tagttaggcc accacttcaa gaactctgta gcaccgccta catacctcgc | 4740 |
| tctgctaatc ctgttaccag tggctgctgc cagtggcgat aagtcgtgtc ttaccgggtt | 4800 |
| ggactcaaga cgatagttac cggataaggc gcagcggtcg ggctgaacgg ggggttcgtg | 4860 |
| cacacagccc agcttggagc gaacgaccta caccgaactg agatacctac agcgtgagct | 4920 |
| atgagaaagc gccacgcttc ccgaagggag aaaggcggac aggtatccgg taagcggcag | 4980 |
| ggtcggaaca ggagagcgca cgagggagct tccaggggga aacgcctggt atctttatag | 5040 |
| tcctgtcggg tttcgccacc tctgacttga gcgtcgattt ttgtgatgct cgtcaggggg | 5100 |
| gcggagccta tggaaaaacg ccagcaacgc ggccttttta cggttcctgg cttttgctg | 5160 |
| gccttttgct cacatgttct | 5180 |

<210> SEQ ID NO 10
<211> LENGTH: 5180
<212> TYPE: DNA
<213> ORGANISM: Artificial Sequence
<220> FEATURE:
<223> OTHER INFORMATION: Synthetic construct

<400> SEQUENCE: 10

| | |
|---|---|
| gactcttcgc gatgtacggg ccagatatac gcgttgacat tgattattga ctagttatta | 60 |
| atagtaatca attacggggt cattagttca tagcccatat atggagttcc gcgttacata | 120 |
| acttacggta aatggcccgc ctggctgacc gcccaacgac ccccgcccat tgacgtcaat | 180 |
| aatgacgtat gttcccatag taacgccaat agggactttc cattgacgtc aatgggtgga | 240 |
| gtatttacgg taaactgccc acttggcagt acatcaagtg tatcatatgc caagtacgcc | 300 |
| ccctattgac gtcaatgacg gtaaatggcc cgcctggcat tatgcccagt acatgacctt | 360 |
| atgggacttt cctacttggc agtacatcta cgtattagtc atcgctatta ccatggtgat | 420 |
| gcggttttgg cagtacatca atgggcgtgg atagcggttt gactcacggg gatttccaag | 480 |

```
tctccacccc attgacgtca atgggagttt gttttggcac caaaatcaac gggactttcc      540
aaaatgtcgt aacaactccg ccccattgac gcaaatgggc ggtaggcgtg tacggtggga      600
ggtctatata agcagagctc tctggctaac tagagaaccc actgcttact ggcttatcga      660
aattaatacg actcactata gggagaccca agctggctag cgtttaaact taagcttggt      720
accgccgccg ccatgggcaa gaggtccgcc ggctcaatca tgtggctcgc gagcttggca      780
gttgtcatag cttgtgcagg cgccttccat ttaaccacac gtaacggaga accacacatg      840
atcgtcagca gacaagagaa agggaaaagt cttctgttta aaacagagga tggcgtgaac      900
atgtgtaccc tcatggccat ggaccttggt gaattgtgtg aagacacaat cacgtacaag      960
tgtccccttc tcaggcagaa tgagccagaa gacatagact gttggtgcaa ctctacgtcc     1020
acgtgggtaa cttatgggac gtgtaccacc atgggagaac atagaagaga aaaagatca     1080 gtggcactcg ttccacatgt gggaatggga ctggagacac gaactgaaac atggatgtca     1140
tcagaagggg cctggaaaca tgtccagaga attgaaactt ggatcttgag acatccaggc     1200
ttcaccatga tggcagcaat cctggcatac accataggaa cgacacattt ccaaagagcc     1260
ctgatttttc tcttactgac agctgtcact cccttcaatga caatgcgttg cataggaatg     1320
tcaaatagag actttgtgga agggggttca ggaggaagct gggttgacat agtcttagaa     1380
catgggagct gtgtgacgac gatggcaaaa aacaaaccaa cattggattt tgaactgata     1440
aaaacagaag ccaaacagcc tgccacccta aggaagtact gtatagaggc aaagctaacc     1500
aacacaacaa cagaatctcg ctgcccaaca caagggaac ccagcctaaa tgaagagcag     1560
gacaaaaggt tcgtctgcaa acactccatg gtagacagag gatgggaaa tggatgtcgc     1620 gactttggaa agggaggcat tgtgacctgt gctatgttca gatgcaaaaa gaacatggaa     1680
ggaaaagttg tgcaaccaga aaacttggaa tacaccattg tgataacacc tcactcaggg     1740
gaagagcatg cagtcggaaa tgacacagga aaacatggca aggaaatcaa aataacacca     1800
cagagttcca tcacagaagc agaattgaca ggttatggca ctgtcacaat ggagtgctct     1860
ccaagaacgg gcctcgactt caatgagatg gtgttgttgc agatgaaaaa taagcttggg     1920
ctggtgcaca ggcaatggtt cctagacctg ccgttaccat ggttgcccgg agcggacaca     1980
caagggtcaa attggataca gaaagagaca ttggtcactt tcaaaaatcc ccatgcgaag     2040
aaacaggatg ttgttgtttt aggatcccaa gaaggggcca tgcacacagc acttacaggg     2100
gccacagaaa tccaaatgtc atcaggaaac ttactcttca caggacatct caagtgcagg     2160
ctgagaatga caagctaca gctcaaagga atgtcatact ctatgtgcac aggaaagttt     2220
aaagttgtgg agcgaatagc agaaacacaa catggaacaa tagttatcag agtgcaatat     2280
gaaggggacg gctctccatg caagatccct tttgagataa tggatttgga aaaaagacat     2340
gtcttaggtc gcctgattac agtcaaccca attgtgacag aaaaagatag ccgggtcaac     2400
atagaagcag aacctccatt cggagacagc tacatcatca taggagtaga gccgggacaa     2460
ctgaagctca actggtttaa gaaggaagc acgctgggca aggcctttc aacaactttg     2520 aagggagcgt aagtatcaag gttacaagac aggtttaagg agaccaatag aaactgggct     2580
tttcgtgtcc ttcaactgca gtgtccttca acgaaacaga gaagactctt gcgtttctga     2640
taggcaccta ttggtcttac tgacatccac tttgcctttc tctccacagt caaagactgg     2700
cagcgttggg cgacacagcc tgggactttg gctctattgg aggggtcttc aactcccatag     2760 gaaaagccgt tcaccaagtg tttggtggtg ccttcagaac actctttggg ggaatgtctt     2820
```

-continued

```
ggatcacaca agggctaatg ggtgccctac tgctctggat gggcataaac gcacgagacc    2880
gatcaattgc tttgaccttc ttagccgtag ggggtgtgct cctgttctta gcgaccaatg    2940
tgcatgctta attagtttga gcggccgctc gagtctagag ggcccgttta aacccgctga    3000
tcagcctcga ctgtgccttc tagttgccag ccatctgttg tttgcccctc ccccgtgcct    3060
tccttgaccc tggaaggtgc cactcccact gtcctttcct aataaaatga ggaaattgca    3120
tcgcattgtc tgagtaggtg tcattctatt ctggggggtg gggtggggca ggacagcaag    3180
ggggaggatt gggaagacaa tagcaggcat gctggggatg cggtgggctc tatggcttct    3240
actgggcggt tttatggaca gcaagcgaac cggaattgcc agctggggcg ccctctggta    3300
aggttgggaa gccctgcaaa gtaaactgga tggctttctc gccgccaagg atctgatggc    3360
gcaggggatc aagctctgat caagagacag gatgaggatc gtttcgcatg attgaacaag    3420
atggattgca cgcaggttct ccggccgctt gggtggagag gctattcggc tatgactggg    3480
cacaacagac aatcggctgc tctgatgccg ccgtgttccg gctgtcagcg caggggcgcc    3540
cggttctttt tgtcaagacc gacctgtccg gtgccctgaa tgaactgcaa gacgaggcag    3600
cgcggctatc gtggctggcc acgacgggcg ttccttgcgc agctgtgctc gacgttgtca    3660
ctgaagcggg aagggactgg ctgctattgg gcgaagtgcc ggggcaggat cctgtgtcat    3720
ctcaccttgc tcctgccgag aaagtatcca tcatggctga tgcaatgcgg cggctgcata    3780
cgcttgatcc ggctacctgc ccattcgacc accaagcgaa acatcgcatc gagcgagcac    3840
gtactcggat ggaagccggt cttgtcgatc aggatgatct ggacgaagag catcaggggc    3900
tcgcgccagc cgaactgttc gccaggctca aggcgagcat gcccgacggc gaggatctcg    3960
tcgtgaccca tggcgatgcc tgcttgccga atatcatggt ggaaaatggc cgcttttctg    4020
gattcatcga ctgtggccgg ctgggtgtgg cggaccgcta tcaggacata gcgttggcta    4080
cccgtgatat tgctgaagag cttggcggcg aatgggctga ccgcttcctc gtgctttacg    4140
gtatcgccgc tcccgattcg cagcgcatcg ccttctatcg ccttcttgac gagttcttct    4200
gaattattaa cgcttacaat tcctgatgcg gtatttttct ccttacgcat ctgtgcggta    4260
tttcacaccg catacaggtg gcacttttcg ggaaatgtg cgcggaaccc ctatttgttt    4320
atttttctaa atacattcaa atatgtatcc gctcatgaga caataaccct gataaatgct    4380
tcaataatag cacgtgctaa aacttcattt ttaatttaaa aggatctagg tgaagatcct    4440
ttttgataat ctcatgacca aaatccctta acgtgagttt tcgttccact gagcgtcaga    4500
ccccgtagaa aagatcaaag gatcttcttg agatcctttt tttctgcgcg taatctgctg    4560
cttgcaaaca aaaaaaccac cgctaccagc ggtggtttgt ttgccggatc aagagctacc    4620
aactcttttt ccgaaggtaa ctggcttcag cagagcgcag ataccaaata ctgtccttct    4680
agtgtagccg tagttaggcc accacttcaa gaactctgta gcaccgccta catacctcgc    4740
tctgctaatc ctgttaccag tggctgctgc cagtggcgat aagtcgtgtc ttaccgggtt    4800
ggactcaaga cgatagttac cggataaggc gcagcggtcg ggctgaacgg ggggttcgtg    4860
cacacagccc agcttggagc gaacgaccta caccgaactg agatacctac agcgtgagct    4920
atgagaaagc gccacgcttc ccgaagggag aaaggcggac aggtatccgg taagcggcag    4980
ggtcggaaca ggagagcgca cgagggagct tccaggggga aacgcctggt atctttatag    5040
tcctgtcggg tttcgccacc tctgacttga gcgtcgattt ttgtgatgct cgtcaggggg    5100
gcggagccta tggaaaaacg ccagcaacgc ggcctttta cggttcctgg cttttgctg     5160
gccttttgct cacatgttct                                                 5180
```

<210> SEQ ID NO 11
<211> LENGTH: 3986
<212> TYPE: DNA
<213> ORGANISM: Artificial Sequence
<220> FEATURE:
<223> OTHER INFORMATION: Synthetic construct

<400> SEQUENCE: 11

```
gactcttcgc gatgtacggg ccagatatac gcgttgacat tgattattga ctagttatta     60
atagtaatca attacggggt cattagttca tagcccatat atggagttcc gcgttacata    120
acttacggta aatggcccgc ctggctgacc gcccaacgac cccgcccccat tgacgtcaat   180
aatgacgtat gttcccatag taacgccaat agggactttc cattgacgtc aatgggtgga    240
gtatttacgg taaactgccc acttggcagt acatcaagtg tatcatatgc caagtacgcc    300
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttggt    720
accgccgccg ccatgggcaa gaggtccgcc ggctcaatca tgtggctcgc gagcttggca    780
gttgtcatag ctggtacaag cgcttttcac ttgacttcac gagatggaga gccgcgcatg    840
atcgtgggga agaatgaaag agggaaatcc ctacttttta agacagcttc tggaatcaac    900
atgtgcacac tcatagccat ggacttggga gagatgtgtg atgacacggt cacttacaaa    960
tgcccccctca ttgccgaagt ggaacctgaa gacattgact gttggtgcaa ccttacatcg   1020
acatgggtga cttatggaac gtgcaatcaa gctggggagc atagacgcga caagagatca    1080
gtggcgttag ctccccatgt cggcatggga ctggacacac gcacccaaac ctggatgtcg    1140
gctgaaggag cttggagaca agtcgagaag gtagagacat gggcccttag cacccaggg    1200
ttcaccatac tagctctatt tcttgcccat tacataggca cttccctgac ccagaaagtg   1260
gttatttttta tactactaat gctggtcact ccatccatgg caatgagatg cgtgggagta   1320
ggaaacagag attttgtgga aggtctgtcg ggagctacgt gggttgatgt ggtgctcgag    1380
cacggtgggt gtgtgaccac catggctaag aacaagccta cgctggacat agagcttcag    1440
aagaccgagg ccacccaact ggcgacccta aggaagttat gcattgaggg aaaaattacc    1500
aacataacaa ctgactcaag gtgtcctacc caggggaag cgatttttacc tgaggagcag   1560
gaccagaact acgtatgcaa gcatacatac gtggatagag ctggggaaa cggttgtgac    1620
gactttggaa aggaagctt ggtgacatgc gcgaaattcc aatgtttaga atcaatagag   1680
ggaaaagtgg tgcaacatga aacctcaaa tacactgtca tcattacagt gcacacagga    1740
gaccaacacc aggtgggaaa tgacacgcag ggagtcacgg ttgagataac acccaggca    1800
tcaaccgttg aagctatctt gcctgaatat ggaaccttg gctagaatg ctcaccacgg     1860
acaggtttgg atttcaatga aatgatctta ttgacaatga aaacaaagc atggatggta    1920
catagacaat ggttctttga cctacccccta ccatggacat caggagctac aacagaaaca    1980
ccaacttgga acaggaaaga gcttcttgtg acattcaaaa atgcacatgc aaaaaagcaa    2040
```

| | |
|---|---|
| gaagtagttg tccttggatc gcaagaggga gcaatgcaca cagcgctgac aggagctaca | 2100 |
| gagatccaaa actcaggagg tacaagcatt tttgcggggc acttgaaatg tagacttaag | 2160 |
| atggacaaat tagaactcaa ggggatgagc tatgcaatgt gcttgaatac ttttgtgttg | 2220 |
| aaggacaagg tctctgaaac gcagcatggg acaatactca ttaaggttga gtacaaaggg | 2280 |
| gaagatgcac cttgcaagat tcctttctcc acagaggatg acaagggaa agctcacaat | 2340 |
| ggtagactga tcacagccaa cccagtggtg accaagaagg aggaggatgt caacattgag | 2400 |
| gctgaacctc cttttgggga agtaacata gtgattggaa ttggagacaa agccttgaaa | 2460 |
| attaactggt acaagaaggg aagcacgctg ggcaaggcct tttcaacaac tttgaaggga | 2520 |
| gcgtaagtat caaggttaca agacaggttt aaggagacca atagaaactg gcttttcgt | 2580 |
| gtccttcaac tgcagtgtcc ttcaacgaaa cagagaagac tcttgcgttt ctgataggca | 2640 |
| cctattggtc ttactgacat ccactttgcc tttctctcca cagtcaaaga ctggcagcgt | 2700 |
| tgggcgacac agcctgggac tttggctcta ttggagggt cttcaactcc ataggaaaag | 2760 |
| ccgttcacca agtgtttggt ggtgccttca gaacactctt tgggggaatg tcttggatca | 2820 |
| cacaagggct aatgggtgcc ctactgctct ggatgggcat aaacgcacga gaccgatcaa | 2880 |
| ttgctttgac cttcttagcc gtaggggtg tgctcctgtt cttagcgacc aatgtgcatg | 2940 |
| cttaattagt ttgagcggcc gctcgagtct agagggcccg tttaaacccg ctgatcagcc | 3000 |
| tcgactgtgc cttctagttg ccagccatct gttgtttgcc cctcccccgt gccttccttg | 3060 |
| accctggaag gtgccactcc cactgtcctt tcctaataaa atgaggaaat tgcatcgcat | 3120 |
| tgtctgagta ggtgtcattc tattctgggg ggtggggtgg ggcaggacag caaggggag | 3180 |
| gattgggaag acaatagcag gcatgctggg gatgcggtgg gctctatggc ttctactggg | 3240 |
| cggttttatg gacagcaagc gaaccggaat tgccagctgg ggcgccctct ggtaaggttg | 3300 |
| ggaagccctg caaagtaaac tggatggctt tctcgccgcc aaggatctga tggcgcaggg | 3360 |
| gatcaagctc tgatcaagag acaggatgag gatcgtttcg catgattgaa caagatggat | 3420 |
| tgcacgcagg ttctccggcc gcttgggtgg agaggctatt cggctatgac tgggcacaac | 3480 |
| agacaatcgg ctgctctgat gccgccgtgt tccggctgtc agcgcagggg cgcccggttc | 3540 |
| tttttgtcaa gaccgacctg tccggtgccc tgaatgaact gcaagacgag gcagcgcggc | 3600 |
| tatcgtggct ggccacgacg ggcgttcctt gcgcagctgt gctcgacgtt gtcactgaag | 3660 |
| cgggaaggga ctggctgcta ttgggcgaag tgccggggca ggatctcctg tcatctcacc | 3720 |
| ttgctcctgc cgagaaagta tccatcatgg ctgatgcaat gcggcggctg catacgcttg | 3780 |
| atccggctac ctgcccattc gaccaccaag cgaaacatcg catcgagcga gcacgtactc | 3840 |
| ggatggaagc cggtcttgtc gatcaggatg atctggacga agagcatcag gggctcgcgc | 3900 |
| cagccgaact gttcgccagg ctcaaggcga gcatgcccga cggcgaggat ctcgtcgtga | 3960 |
| cccatggcga tgcctgcttg ccgaat | 3986 |

<210> SEQ ID NO 12
<211> LENGTH: 5210
<212> TYPE: DNA
<213> ORGANISM: Artificial Sequence
<220> FEATURE:
<223> OTHER INFORMATION: Synthetic construct

<400> SEQUENCE: 12

| | |
|---|---|
| gactcttcgc gatgtacggg ccagatatac gcgttgacat tgattattga ctagttatta | 60 |
| atagtaatca attacggggt cattagttca tagcccatat atggagttcc gcgttacata | 120 |

```
acttacggta aatggcccgc ctggctgacc gcccaacgac ccccgcccat tgacgtcaat    180
aatgacgtat gttcccatag taacgccaat agggactttc cattgacgtc aatgggtgga    240
gtatttacgg taaactgccc acttggcagt acatcaagtg tatcatatgc caagtacgcc    300
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttggt    720
accgccgccg ccatgggcaa gaggtccgcc ggctcaatca tgtggctcgc gagcttggca    780
gttgtcatag ctggtacaag cgcttttttcc ttgtcaacga gagatggcga accccttatg    840
atagtggcga aacacgaaag ggggagacct ctcttgttta agacaacaga gggaatcaac    900
aagtgcactc ttattgccat ggacctgggt gaaatgtgcg aggacaccgt cacgtataaa    960 tgcccttttac tggtcaatac cgaacccgaa gacattgatt gctggtgcaa tctcacgtct    1020
gcctgggtca tgtatgggac atgcacccaa agtggggaac ggagacgaga gaagcgctca    1080
gtagctctaa caccacattc aggaatggga ttggaaacaa gggctgaaac atggatgtca    1140
tcggaaggag cttggaaaca cgctcagagg gtagagagtt ggatactcag aaacccagga    1200
ttcgcgctct tggcaggatt tatggcctat atgattgggc aaacaggaat ccagcgaaca    1260 gtcttctttta ttttaatgat gctggtcgcc ccatcctacg gaatgcgatg cgtaggagtg    1320
gggaacagag acttcgtgga aggagtctca ggtgagcat gggtcgatct ggtgctagaa    1380 catgaggat gtgtcacaac tatggcccag ggaaaaccaa ccttggattt tgaactgatc    1440
aagacaacag ccaaggaagt ggctctatta agaacctatt gcattgaagc ctctatatca    1500
aacataacca cggcaacaag atgtccaacg caaggagagc cttacctcaa agaggaacaa    1560
gatcaacagt acatctgccg gagagacgtg gtagacagag ggtggggcaa tggctgtgaa    1620
gactttggga aaggaggagt tgtgacatgt gcgaagtttt catgctcggg gaagataaca    1680
ggcaacttag tccaaattga gaaccttgaa tacacagtgg ttgtaacagt ccacaatgga    1740
gacacccatg cagtaggaaa tgacacatcc aaccacggag tgacagccac gataaccccc    1800
aggtcaccat cggtagaagt taaattgccg gactatggag aattgacact cgattgtgaa    1860
cccaggtccg gaattgactt taatgagatg attctgatga aaatgaaaaa gaaaacgtgg    1920
cttgtgcaca gcaatggttt tttggatcta cctctaccat ggcagcagg agcagacacg    1980 tcagaagttc attggaatca caaagagaga atggtgacgt tcaaggtccc tcatgctaag    2040 agacaggat tgacagtgct aggatctcag gaaggagcca tgcattcagc cctcaccgga    2100
gccacagaag tggattccgg tgatggaaac cacatgtttg ccggacattt gaagtgcaaa    2160
gttcgcatgg agaaattgag gatcaaggga atgtcgtaca cgatgtgctc aggaaagttc    2220
tcaattgatg accagatggc agaaacacag catgggacaa cagtggtaaa agtcaagtat    2280
gagggtgctg gagctccatg taaagttccc atagagataa gagatgtgaa caaggaaaaa    2340
gtggttgggc gtatcatctc atctacccct tttgctgaga ataccaacag tgtgaccaat    2400
atagaattgg aaccccctttt tggggatagc tacatagtga taggtgtggg agacagtgca    2460
```

```
ctaacacagc attggttcag gaaagggagt acgctgggca aggccttttc aacaactttg    2520
aagggagcgt aagtatcaag gttacaagac aggtttaagg agaccaatag aaactgggct    2580
tttcgtgtcc ttcaactgca gtgtccttca acgaaacaga gaagactctt gcgtttctga    2640
taggcaccta ttggtcttac tgacatccac tttgcctttc tctccacagt caaagactgg    2700
cagcgttggg cgacacagcc tgggactttg gctctattgg aggggtcttc aactccatag    2760
gaaaagccgt tcaccaagtg tttggtggtg ccttcagaac actctttggg ggaatgtctt    2820
ggatcacaca agggctaatg ggtgccctac tgctctggat gggcataaac gcacgagacc    2880
gatcaattgc tttgaccttc ttagccgtag ggggtgtgct cctgttctta gcgaccaatg    2940
tgcatgctta attagtttga gcggccgctc gagcatgcat ctagagggcc ctattctata    3000
gtgtcaccta aatgctagag ctcgctgatc agcctcgact gtgccttcta gttgccagcc    3060
atctgttgtt tgcccctccc ccgtgccttc cttgaccctg gaaggtgcca ctcccactgt    3120
cctttcctaa taaaatgagg aaattgcatc gcattgtctg agtaggtgtc attctattct    3180
ggggggtggg ggtggggcag gacagcaagg ggaggattgg aagacaat agcaggcatg    3240 ctggggatgc ggtgggctct atggcttcta ctgggcggtt ttatggacag caagcgaacc    3300
ggaattgcca gctggggcgc cctctggtaa ggttgggaag ccctgcaaag taaactggat    3360
ggctttctcg ccgccaagga tctgatggcg caggggatca agctctgatc aagagacagg    3420
atgaggatcg tttcgcatga ttgaacaaga tggattgcac gcaggttctc cggccgcttg    3480
ggtggagagg ctattcggct atgactgggc acaacagaca atcggctgct ctgatgccgc    3540
cgtgttccgg ctgtcagcgc aggggcgccc ggttcttttt gtcaagaccg acctgtccgg    3600
tgccctgaat gaactgcaag acgaggcagc gcggctatcg tggctggcca cgacgggcgt    3660
tccttgcgca gctgtgctcg acgttgtcac tgaagcggga agggactggc tgctattggg    3720
cgaagtgccg gggcaggatc tcctgtcatc tcaccttgct cctgccgaga agtatccat    3780 catggctgat gcaatgcggc ggctgcatac gcttgatccg gctacctgcc cattcgacca    3840
ccaagcgaaa catcgcatcg agcgagcacg tactcggatg aagccggtc ttgtcgatca    3900 ggatgatctg gacgaagagc atcagggct cgcgccagcc gaactgttcg ccaggctcaa    3960
ggcgagcatg cccgacggcg aggatctcgt cgtgacccat ggcgatgcct gcttgccgaa    4020
tatcatggtg gaaaatggcc gcttttctgg attcatcgac tgtggccggc tgggtgtggc    4080
ggaccgctat caggacatag cgttggctac ccgtgatatt gctgaagagc ttggcggcga    4140
atgggctgac cgcttcctcg tgctttacgg tatcgccgct cccgattcgc agcgcatcgc    4200
cttctatcgc cttcttgacg agttcttctg aattattaac gcttacaatt tcctgatgcg    4260
gtattttctc cttacgcatc tgtgcggtat ttcacaccgc atacaggtgg cacttttcgg    4320
ggaaatgtgc gcggaacccc tatttgttta ttttcctaaa tacattcaaa tatgtatccg    4380
ctcatgagac aataaccctg ataaatgctt caataatagc acgtgctaaa acttcatttt    4440
taatttaaaa ggatctaggt gaagatcctt tttgataatc tcatgaccaa atcccttaa    4500 cgtgagtttt cgttccactg agcgtcagac cccgtagaaa agatcaaagg atcttcttga    4560
gatccttttt ttctgcgcgt aatctgctgc ttgcaaacaa aaaaaccacc gctaccagcg    4620
gtggtttgtt tgccggatca agagctacca actcttttc cgaaggtaac tggcttcagc    4680
agagcgcaga taccaaatac tgtccttcta gtgtagccgt agttaggcca ccacttcaag    4740
aactctgtag caccgcctac atacctcgct ctgctaatcc tgttaccagt ggctgctgcc    4800
agtggcgata gtcgtgtct taccgggttg gactcaagac gatagttacc ggataaggcg    4860
```

```
cagcggtcgg gctgaacggg gggttcgtgc acacagccca gcttggagcg aacgacctac    4920
accgaactga gatacctaca gcgtgagcta tgagaaagcg ccacgcttcc cgaagggaga    4980
aaggcggaca ggtatccggt aagcggcagg gtcggaacag gagagcgcac gagggagctt    5040 ccaggggaa acgcctggta tctttatagt cctgtcgggt ttcgccacct ctgacttgag     5100
cgtcgatttt tgtgatgctc gtcaggggg cggagcctat ggaaaaacgc cagcaacgcg     5160
gcctttttac ggttcctggg cttttgctgg ccttttgctc acatgttctt               5210
```

<210> SEQ ID NO 13
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 13

```
ttcctttccg aagagacgac agccattgcc ccagcc                               36
```

<210> SEQ ID NO 14
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 14

```
ttcctttcc gaaatcccca cagccattgc cccag                                 35
```

<210> SEQ ID NO 15
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 15

```
cttccttttc cgaaatcccg acagccattg ccccagcc                             38
```

<210> SEQ ID NO 16
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 16

```
agccacttcg tcctctagct tgaatgagcc tgtgc                                35
```

<210> SEQ ID NO 17
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 17

```
tcagccacct ttttctctag cttgaatgag cctgtgc                              37
```

<210> SEQ ID NO 18
<211> LENGTH: 42
<212> TYPE: DNA
<213> ORGANISM: Artificial Sequence
<220> FEATURE:

```
<223> OTHER INFORMATION: Synthetic polynucleotide

<400> SEQUENCE: 18
gggtctcagc caccttgtcc tctagcttga atgagcctgt gc                    42

<210> SEQ ID NO 19
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 19
gcctcaatgt tgacctgttt ttctttgtca gtgactatgg g                     41
```

DENGUE VIRUS E-GLYCOPROTEIN POLYPEPTIDES CONTAINING MUTATIONS THAT ELIMINATE IMMUNODOMINANT CROSS-REACTIVE EPITOPES

CROSS REFERENCE TO RELATED APPLICATIONS

This is a continuation of U.S. application Ser. No. 16/107,119, filed Aug. 21, 2018, which is a divisional of U.S. application Ser. No. 15/262,268, filed Sep. 12, 2016, issued as U.S. Pat. No. 10,092,637 on Oct. 9, 2018, which is a divisional of U.S. application Ser. No. 14/352,812, filed Apr. 18, 2014, now abandoned, which is the U.S. National Stage of International Application No. PCT/US2012/060872, filed Oct. 18, 2012, published in English under PCT Article 21(2), which claims the benefit of U.S. Provisional Application No. 61/549,348, filed Oct. 20, 2011. The above-referenced applications are herein incorporated by reference in their entirety.

FIELD

This disclosure concerns immunogenic dengue virus compositions in which immunodominant cross-reactive epitopes have been removed, and their use for redirecting an immune response for safe and efficacious dengue vaccination.

BACKGROUND

Dengue viruses (DENV) are the most prevalent arthropod-borne viral pathogens infecting humans. These mosquito-transmitted viruses, members of the Flaviviridae, are endemic to most tropical and sub-tropical countries with nearly half of the world's population living at risk of DENV infection and resulting in over a million estimated infections annually (Mackenzie et al., *Nat Med* 10:S98-109, 2004; Gubler, *Arch Med Res* 33:330-342, 2002). Infection with DENV can cause a broad range of symptoms, ranging from subclinical, to the self-limiting flu-like illness dengue fever (DF), to the more severe and life-threatening dengue hemorrhagic fever and shock syndrome (DHF/DSS) characterized by increased vascular permeability producing plasma leakage, severe thrombocytopenia and hypotension leading to circulatory collapse (Gubler, *Novartis Found Symp* 277: 3-16; discussion 16-22, 71-13, 251-253, 2006). DENV prevalence, infection rates, and disease severity have increased exponentially since the middle of the last century (Guzman et al., *Nat Rev Microbiol* 8:S7-S16, 2010). Despite decades of interest, need, and effort there remains no available dengue vaccine and vaccine candidates continue to run into roadblocks and safety concerns both in pre-clinical development and in clinical trials (Guy et al., *Hum Vaccin* 6(9), Epub Sep. 16, 2010; Miller, *Curr Opin Mol Ther* 12:31-38, 2010; Thomas, *J Infect Dis* 203:299-303, 2011; Murphy and Whitehead, *Annu Rev Immunol* 29:587-619, 2011).

Dengue vaccine development is plagued by a number of biological and immunological challenges that also affect vaccinology for other multi-strain pathogens. These include the necessity for a tetravalent vaccine inducing balanced immunity, the lack of an animal model for DENV disease, and concerns regarding vaccine-induced severe DENV pathology (Murphy and Whitehead, *Annu Rev Immunol* 29:587-619, 2011; Morens and Fauci, *JAMA* 299:214-216, 2008). DENV immune responses are both protective and pathogenic and it is this duality that directly impedes vaccine development (Rothman, *J Clin Invest* 113:946-951, 2004). There are four closely related yet phylogenetically distinct DENV serotypes (DENV-1, -2, -3, and -4) and infection with any one serotype appears to induce life-long serotype-specific immunity, yet cross-protection between serotypes is limited and transient (Sabin, *Am J Trop Med Hyg* 1:30-50, 1952; Kuno, *Adv Virus Res* 61:3-65, 2033). Thus, in endemic regions individuals are susceptible to up to four different DENV infections.

Although there are a number of risk factors associated with DHF such as virus and host genetics, by far the strongest risk factor for severe dengue pathology is secondary infection with a previously unencountered (heterologous) serotype (Murphy and Whitehead, *Annu Rev Immunol* 29:587-619, 2011). This association explains the exponential increase of DHF/DSS in recent decades as co-circulation and simultaneous transmission of the four DENV serotypes increases both temporally and geographically (Mackenzie et al., *Nat Med* 10:S98-109, 2004; Gubler, *Novartis Found Symp* 277:3-16; Guzman et al., *Nat Rev Microbiol* 8:S7-S16, 2010). In humans, increasing viral load correlates with DENV disease severity and a large body of evidence points to the importance of immune enhancement being a causal factor for the increased viral loads associated with DHF (Vaughn et al., *J Infect Dis* 181:2-9, 2000; Libraty et al., *J Infect Dis* 185:1213-1221, 2002).

SUMMARY

Disclosed herein are dengue virus E-glycoprotein polypeptides containing mutations that eliminate immunodominant cross-reactive epitopes associated with immune enhancement. In some cases, the dengue virus E-glycoproteins further include mutations that introduce a strong CD4 T cell epitope. The disclosed E-glycoprotein polypeptides, or nucleic acid molecules encoding the polypeptides, can be used, for example, in monovalent or tetravalent vaccines against dengue virus.

Provided herein are cross-reactivity reduced dengue virus E-glycoprotein polypeptides having amino acid substitutions at residues corresponding to positions 106, 107, 310 and 311, and either position 364 or position 389 of dengue serotype 1 (DENV-1) E-glycoprotein (SEQ ID NO: 1). The provided E-glycoprotein polypeptides optionally further include mutations corresponding to positions 468, 478, 482 and 487 of DENV-1 E-glycoprotein (SEQ ID NO: 1).

In some embodiments, the cross-reactivity reduced dengue virus E-glycoprotein polypeptide is selected from: (1) a dengue serotype 1 virus (DENV-1) E-glycoprotein polypeptide comprising an arginine at position 106, an aspartic acid at position 107, an aspartic acid at position 310, a lysine at position 311, a glutamine at position 364, an isoleucine at position 468, a threonine at position 478, a valine at position 482 and a leucine at position 487, numbered with reference to SEQ ID NO: 1; (2) a dengue serotype 2 virus (DENV-2) E-glycoprotein polypeptide comprising an arginine at position 106, an aspartic acid at position 107, an glutamic acid at position 310, an arginine at position 311, an arginine at position 364, an isoleucine at position 468, a threonine at position 478, a valine at position 482 and a leucine at position 487, numbered with reference to SEQ ID NO: 2; (3) a dengue serotype 3 virus (DENV-3) E-glycoprotein polypeptide comprising an aspartic acid at position 106, an aspartic acid at position 107, an aspartic acid at position 308, a lysine at position 309, an aspartic acid at position 362, an isoleucine at position 466, a threonine at position 476, a valine at position 480 and a leucine at position 485, numbered with reference to SEQ ID NO: 3; and (4) a dengue serotype 4 virus (DENV-4) E-glycoprotein polypeptide comprising a glutamic acid at position 106, an aspartic acid at position 107, an aspartic acid at position 310, a glutamine at position 311, a glutamine at position 389, an isoleucine at position 468, a threonine at position 478, a valine at position 482 and a leucine at position 487, numbered with reference to SEQ ID NO: 4.

Isolated virus-like particles (VLPs) comprising the disclosed polypeptides, recombinant nucleic acid molecules encoding the disclosed polypeptides and VLPs, vectors comprising the recombinant nucleic acid molecules and isolated cells comprising the vectors are further provided by the present disclosure.

Also provided are compositions comprising the cross-reactivity reduced E-glycoprotein polypeptides, VLPs, recombinant nucleic acid molecules and vectors disclosed herein.

Further provided are methods of eliciting an immune response in a subject against dengue virus by administering to the subject a therapeutically effective amount of the cross-reactivity reduced E-glycoprotein polypeptides, VLPs, recombinant nucleic acid molecules, vectors and compositions disclosed herein. In some examples, an E-glycoprotein polypeptide (or recombinant nucleic acid molecule encoding the polypeptide) from a single dengue virus serotype is administered as a monovalent vaccine. In other examples, an E-glycoprotein polypeptide (or recombinant nucleic acid molecule encoding the polypeptide) from each of the four dengue virus serotypes is administered as a tetravalent vaccine. The disclosed nucleic acid molecules encoding the cross-reactivity reduced dengue virus E-glycoproteins can be used, for example, in DNA prime-protein boost vaccine strategies.

The foregoing and other features, and advantages of the disclosure will become more apparent from the following detailed description, which proceeds with reference to the accompanying figures.

BRIEF DESCRIPTION OF THE DRAWINGS

(FIG. 1A) Locations of the pVD1-CRR substitutions (spheres) on a ribbon diagram of the mature E dimer as they appear looking straight down toward the virion surface. The three structural domains are labeled (EDI, EDII and EDIII). The fusion peptide is also labeled. The glycans in EDI (N67) and EDII (N153) are depicted as ball and stick representations. (FIG. 1B) Side-view of the E protein dimer. (FIG. 1C) Close-up of the $EDII_{FP}$ and EDIII regions of one monomer of the E dimer as it appears in panel (B). The side chains of two residues in the $EDII_{FP}$ and three residues in EDIII where CRR substitutions were introduced are depicted as ball and stick representations and labeled with the introduced substitutions. The two antigenic regions $EDII_{FP}$ and $EDIII_{CR}$ are noted with circles roughly representing the size of an IgG footprint binding to these regions.

(FIGS. 2A-2D) 12 week post vaccination immunogenicity of AG129 mice immunized (i.m.) with 100 μg of pVD1-WT or pVD1-CRR vaccines at 0, 4 and 8 weeks. Geometric means and 95% confidence intervals are depicted unless otherwise noted. All end-point titers were $\log_{10}$ transformed and statistical significance was determined using the Mann-Whitney test to account for non-normality of some transformed data. (FIG. 2B) and (FIG. 2C) both used a one-tailed test since there was an a priori expectation that pVD1-CRR immunized mice would exhibit reduced $EDII_{FP}$ recognizing IgG. (FIG. 2A) DENV-1 total IgG end-point titers 12 weeks post immunization. (FIG. 2B) Percent of total DENV-1 IgG recognizing immunodominant $EDII_{FP}$ epitopes, arithmetic means and 95% CI depicted. (FIG. 2C) Calculated DENV-1 $EDII_{FP}$ IgG end-point titers. (FIG. 2D) DENV-1 50% antigen focus-reduction micro neutralization titers ($FR\mu NT_{50}$). A t-test was utilized here as both data sets were normally distributed. (FIG. 2E) pVD1-WT and pVD1-CRR immunized AG129 mice were challenged with $1.1 \times 10^5$ FFU of DENV-1 (Mochizuki strain, i.p.) at 12 weeks. Kaplan-Meier survival curves are shown. Both pVD1-WT (n=18) and pVD1-CRR (n=18) vaccinated animals had the same survival (94%), which was highly significant in comparison to naïve mice (n=4, p=0.0003). (FIG. 2F) Four mice from each vaccine treatment (not included in the survival curves) were a priori scheduled to be euthanized 3 and 8 DPC. DENV-1 titers (FFU/mL) were $\log_{10}$ transformed and analyzed using 2-way ANOVA; error bars represent standard error of the mean (SEM). Vaccine treatment was highly significant (p<0.0001). Bonferroni post-tests indicated that viremia of each vaccinated group was significantly lower than for naïve mice (n=2) 3 DPC (p<0.001), only pVD1-CRR vaccinated mouse viremia was significantly lower than naïve mice (n=2) 8 DPC (p<0.01) and there was no difference between WT or CRR vaccinated mouse viremia 3 or 8 DPC.

FIGS. 3A-3F: DENV-1 CRR vaccine stimulates reduced levels of immunodominant cross-reactive $EDII_{FP}$ IgG and reduces enhanced DENV-2 mortality. (FIGS. 3A-C) 12 week post vaccination immunogenicity of AG129 mice immunized (i.m.) with 100 μg of pVD1-WT or pVD1-CRR vaccines. Geometric means and 95% confidence intervals are depicted. End-point titers were $\log_{10}$ transformed and statistical significance was determined using the two-tailed Mann-Whitney test. (FIG. 3B) and (FIG. 3C) both used a one-tailed test since there was an a priori expectation that pVD1-CRR immunized mice would exhibit reduced $EDII_{FP}$ recognizing IgG. (FIG. 3A) DENV-1 total IgG end-point titers 12 weeks post immunization. (FIG. 3B) Percent of total DENV-1 IgG recognizing immunodominant $EDII_{FP}$ epitopes, arithmetic means and 95% CI depicted. (FIG. 3C) Calculated DENV-1 $EDII_{FP}$ IgG end-point titers. (FIG. 3D) Survival of pVD1-WT and pVD1-CRR immunized AG129 mice following sublethal heterologous DENV-2 challenge. 12 weeks following vaccination, immunized mice (n=22) or age matched naïve controls (n=8) were challenged (i.p.) with $4.2 \times 10^5$ FFU of DENV-2 S221. Kaplan-Meier survival curves and p values are shown. All naïve mice survived virus challenge with minimal signs of morbidity, pVD1-WT vaccinated mice suffered 95% mortality from enhanced DENV-2 disease (p<0.0001, compared to naïve). pVD1-CRR immunized mice exhibited 68% survival which did not differ from naïve mouse survival (100%, p=0.0769) yet was significantly greater than pVD1-WT immunized mouse survival (4.5%, p<0.0001). The Bonferroni multiple comparison adjusted α=0.017. (FIG. 3E) pVD1-CRR vaccinated mice exhibited a rapid, large magnitude increase in DENV-2 neutralizing antibody titers following DENV-2 challenge. $FR\mu NT_{50}$ titers determined with DENV-2 16681 virus on Vero cells, $\log_{10}$ transformed and the transformed data analyzed by 2-way ANOVA (p<0.0001). Bonferroni posttest significance is depicted with asterisks, error bars represent SEM. 0, 3, 4, and 5 DPC n=4, 4, 5 and 9 for WT and 4, 4, 1, and 3 for CRR immunized mice, respectively. (FIG. 3F) Viremia of pVD1-WT vaccinated mice increased rapidly 3-5 days after DENV-2 S221 challenge, whereas pVD1-CRR vaccinated mice had 30-fold, 40-fold, and at least 1800-fold lower viremia 3, 4, and 5 DPC (all CRR mice<10 FFU/mL) than did WT immunized mice. Virus titers were $log_{10}$ transformed and the transformed data analyzed by 2-way ANOVA (p<0.0001). Bonferroni posttest significance is depicted with asterisks, error bars represent SEM. 3, 4 and 5 DPC n=4, 5, and 6 for WT and 4, 1, and 3 for CRR immunized mice, respectively.

FIGS. 4A-4C: Pathophysiology of enhanced DENV disease in vaccinated AG129 mice. (FIG. 4A) Enhanced DENV disease associated vascular leak pathology of pVD1-WT and -CRR vaccinated mice following sub-lethal heterologous DENV-2 infection. No pathology was visible in naïve or vaccinated mice 3 DPC, yet by 4 and 5 DPC mice succumbing to enhanced disease exhibited severe vascular leakage associated pathology. The same mouse is shown in the bottom two photos to highlight the severe intestinal hemorrhage observed in pVD1-WT but not in pVD1-CRR vaccinated mice (arrows). (FIG. 4B) Histology of uninfected, pVD1-WT, and pVD1-CRR vaccinated mouse livers 3 DPC. The top row is hematoxylin and eosin stained liver sections and the bottom row is immunohistochemistry for DENV-2 NS1 protein of the same individual animals. NS1+mononuclear inflammatory cells and sinusoidal endothelial cells stain positive in their cytoplasm and are visible (arrows) in liver tissue from vaccinated mice but not uninfected mice. Multiple sections from multiple animals were examined and single representatives are shown. All photos were taken at 400× magnification. (FIG. 4C) In vitro DENV-2 enhancement by pVD1-WT and pVD1-CRR vaccinated serum 12 weeks following vaccinations and one day prior to DENV-2 challenge. Consistent with the in vivo results, pVD1-WT vaccinated serum significantly enhanced DENV-2 infection whereas pVD1-CRR vaccinated serum did not (p=0.0012). The data are representative of two independent experiments of 4 pools of 6-7 individual serum specimens for each vaccine treatment and were analyzed with 2-way ANOVA and Bonferroni post test significance at individual dilutions is depicted with asterisks.

FIGS. 5A-5F: DENV-1 CRR vaccination sculpts immunity to redirect secondary immunity to heterologous dengue infection. AG129 mice were immunized (i.m.) with 100 µg of pVD1-WT or pVD1-CRR vaccines and challenged at 12 weeks with heterologous DENV-2 S221 (4.2×10$^5$ FFU, i.p.). Arithmetic means and SEM are depicted in A, B, D, and E and analyzed with two-way ANOVA. Bonferroni post test significance is depicted with asterisks. (FIG. 5A) DENV-1 total IgG end-point titers of pVD1-WT and -CRR immunized mice 3, 4, and 5 DPC with DENV-2. Three, 4, and 5 DPC n=4, 3, and 8 and 4, 1, and 3 for WT and CRR vaccines, respectively. (FIG. 5B) DENV-2 total IgG end-point titers of pVD1-WT and -CRR vaccinated mice. (FIG. 5C) Percent DENV-1 epitope-specific responses pre- and post-challenge for IgG recognizing immunodominant cross-reactive EDII$_{FP}$ epitopes. pVD1-WT immunized mice had larger populations of EDII$_{FP}$ post DENV-2 challenge than did pVD1-CRR immunized mice (ave=35.5% and 7.65% respectively, p=0.0004). pVD1-WT immunized mice also exhibited an increase in EDII$_{FP}$ IgG from pre- to post-DENV-2 challenge (ave=17.7% and 35.5% respectively, p=0.0057. Geometric means and 95% CI are depicted. Statistical significance was determined with a one-tailed Mann-Whitney U. The Bonferroni α=0.025. (FIG. 5D, 5E) DENV-2 epitope specific IgG responses post DENV-2 challenge of pVD1-WT and pVD1-CRR immunized AG129 mice; 3, 4, and 5 DPC n=4, 5, and 9 and 4, 1, and 2 for WT and CRR immunized mice, respectively. (FIG. 5D) Percent DENV-2 IgG recognizing immunodominant cross-reactive EDII$_{FP}$ epitopes. (FIG. 5E) Percent DENV-2 IgG recognizing E protein epitopes outside of immunodominant EDII$_{FP}$ and EDIII$_{CR}$ antigenic regions (Non-EDII$_{FP}$EDIII$_{CR}$). (FIG. 5F) FRµNT$_{50}$ titers of pVD1-WT and -CRR immunized mouse sera 3 DPC with DENV-2 against DENV-1, DENV-2, DENV-3 and DENV-4. Bars represent GMT, statistical significance was determined with a one-tailed t-test. All titers were login transformed prior to analysis.

SEQUENCE LISTING

Figure 1A:
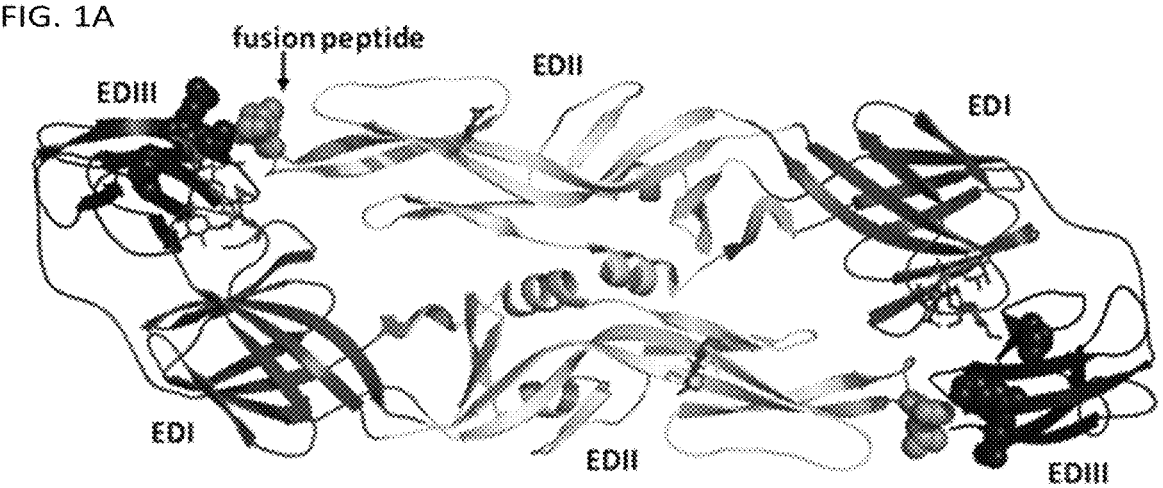
FIGS. 1A-1C: Structural locations of the pVD1-CRR envelope (E) protein cross-reactive epitope knock out substitutions. The locations of the DENV-1 E substitutions introduced to construct pVD1-CRR are mapped on the crystal structure of the homologous DENV-2 E protein dimer (Modis et al., *Proc Natl Acad Sci USA* 100:6986-6991, 2003).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Dec. 19, 2019, 67.4 KB, which is incorporated by reference herein. In the accompanying Sequence Listing:

SEQ ID NO: 1 is the amino acid sequence of a mutant DENV-1 E protein with reduced cross-reactivity. This sequence comprises 80% DENV-1 E protein sequence at the N-terminus and 20% Japanese encephalitis virus (JEV) sequence at the C-terminus.

SEQ ID NO: 2 is the amino acid sequence of a mutant DENV-2 E protein with reduced cross-reactivity.

SEQ ID NO: 3 is the amino acid sequence of a mutant DENV-3 E protein with reduced cross-reactivity. This sequence comprises 80% DENV-3 E protein sequence at the N-terminus and 20% Japanese encephalitis virus (JEV) sequence at the C-terminus.

SEQ ID NO: 4 is the amino acid sequence of a mutant DENV-4 E protein with reduced cross-reactivity. This sequence comprises 80% DENV-4 E protein sequence at the N-terminus and 20% Japanese encephalitis virus (JEV) sequence at the C-terminus.

SEQ ID NO: 5 is the amino acid sequence of the DENV-1 prM/E protein encoded by the pVD1iRDDKQ TMD construct.

SEQ ID NO: 6 is the amino acid sequence of the DENV-2 prM/E protein encoded by the pVD2iRDERR TMD construct.

SEQ ID NO: 7 is the amino acid sequence of the DENV-3 prM/E protein encoded by the pVD3iDDDKD TMD construct.

SEQ ID NO: 8 is the amino acid sequence of the DENV-4 prM/E protein encoded by the pVD4iEDDQQ TMD construct.

SEQ ID NO: 9 is the nucleotide sequence of the pVD1iRDDKQ TMD construct.

SEQ ID NO: 10 is the nucleotide sequence of the pVD2iRDERR TMD construct.

SEQ ID NO: 11 is the nucleotide sequence of the pVD3iDDDKD TMD construct.

SEQ ID NO: 12 is the nucleotide sequence of the pVD4iEDDQQ TMD construct.

SEQ ID NOs: 13-19 are the nucleotide sequences of mutagenic primers.

DETAILED DESCRIPTION

I. Abbreviations

ADE antibody-dependent enhancement
CRR cross-reactivity reduced
DENV dengue virus
DF dengue fever
DHF dengue hemorrhagic fever
DPC days post challenge
DSS dengue shock syndrome
E envelope protein
ELISA enzyme-linked immunosorbent assay
ES-ELISA epitope-specific ELISA
FFU focus-forming unit
FRµNT focus-reduction micro neutralization assay
HRP horseradish peroxidase
IHC immunohistochemistry
i.m. intramuscular
i.p. intraperitoneal
JEV Japanese encephalitis virus
M membrane protein
MAb monoclonal antibody
MHIAF murine hyper-immune ascitic fluid
OD optical density
prM premembrane protein
TLAV tetravalent live attenuated virus
TMD transmembrane domain
VLP virus-like particle
VRP viral replicon particle
WNV West Nile virus
WT wild type II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218, 371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Administer: As used herein, administering a composition (e.g. an immunogenic composition) to a subject means to give, apply or bring the composition into contact with the subject. Administration can be accomplished by any of a number of routes, such as, for example, topical, oral, subcutaneous, intramuscular, intraperitoneal, intravenous, intrathecal and intramuscular.

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Antibody: An immunoglobulin molecule produced by B lymphoid cells with a specific amino acid sequence. Antibodies are evoked in humans or other animals by a specific antigen (immunogen). Antibodies are characterized by reacting specifically with the antigen in some demonstrable way, antibody and antigen each being defined in terms of the other. "Eliciting an antibody response" refers to the ability of an antigen or other molecule to induce the production of antibodies.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens.

Cross-reactivity reduced dengue virus E-glycoprotein: A dengue virus E-glycoprotein containing amino acid substitutions that result in the removal of immunodominant epitopes associated with immune enhancement.

Dengue virus (DENV): An RNA virus of the family Flaviviridae, genus Flavivirus. The dengue virus genome encodes the three structural proteins (C, prM and E) that form the virus particle and seven non-structural proteins (NS1, NS2a, NS2b, NS3, NS4a, NS4b, NS5) that are only found in infected host cells, but are required for replication of the virus. There are four serotypes of dengue virus, referred to as DENV-1, DENV-2, DENV-3 and DENV-4. All four serotypes can cause the full spectrum of dengue disease. Infection with one serotype can produce lifelong immunity to that serotype. However, severe complications can occur upon subsequent infection by a different serotype. Dengue virus is primarily transmitted by *Aedes* mosquitoes, particularly *A. aegypti*. Symptoms of dengue virus infection include fever, headache, muscle and joint pain and a skin rash similar to measles. In a small percentage of cases, the infection develops into a life-threatening dengue hemorrhagic fever, typically resulting in bleeding, low platelet levels and blood plasma leakage, or into dengue shock syndrome characterized by dangerously low blood pressure.

Envelope (E) glycoprotein: A flavivirus structural protein that mediates binding of flavivirus virions to cellular receptors on host cells. The flavivirus E protein is required for membrane fusion, and is the primary antigen inducing protective immunity to flavivirus infection. Flavivirus E protein affects host range, tissue tropism and viral virulence. The flavivirus E protein contains three structural and functional domains, DI-DIII. In mature virus particles the E protein forms head to tail homodimers lying flat and forming a dense lattice on the viral surface.

Immune response: A response of a cell of the immune system, such as a B-cell, T-cell, macrophage or polymorphonucleocyte, to a stimulus such as an antigenic polypeptide or vaccine. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, antibody production and the like.

Immune stimulatory composition: A term used herein to mean a composition useful for stimulating or eliciting a specific immune response (or immunogenic response) in a subject. The immune stimulatory composition can be a protein antigen or a nucleic acid molecule (such as vector) used to express a protein antigen. In some embodiments, the immunogenic response is protective or provides protective immunity, in that it enables the subject to better resist infection with or disease progression from the flavivirus against which the immune stimulatory composition is directed.

In some embodiments, an "effective amount" or "immune-stimulatory amount" of an immune stimulatory composition is an amount which, when administered to a subject, is sufficient to engender a detectable immune response. Such a response may comprise, for instance, generation of an antibody specific to one or more of the epitopes provided in the immune stimulatory composition. Alternatively, the response may comprise a T-helper or CTL-based response to one or more of the epitopes provided in the immune stimulatory composition. All three of these responses may originate from naïve or memory cells. In other embodiments, a "protective effective amount" of an immune stimulatory composition is an amount which, when administered to a subject, is sufficient to confer protective immunity upon the subject.

Immunize: To render a subject protected from an infectious disease, such as by vaccination.

Isolated: An "isolated" or "purified" biological component (such as a nucleic acid, peptide, protein, protein complex, or virus-like particle) has been substantially separated, produced apart from, or purified away from other biological components in the cell of the organism in which the component naturally occurs, that is, other chromosomal and extrachromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total biological component content of the preparation.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compositions, such as one or more flavivirus vaccines, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

A conservative substitution in a polypeptide is substitution of one amino acid residue in a protein sequence for a different amino acid residue having similar biochemical properties. Typically, conservative substitutions have little to no impact on the activity of a resulting polypeptide. For example, a flavivirus protein including one or more conservative substitutions (for example no more than 2, 5, 10, 20, 30, 40, or 50 substitutions) retains the structure and function of the wild-type protein. A polypeptide can be produced to contain one or more conservative substitutions by manipulating the nucleotide sequence that encodes that polypeptide using, for example, standard procedures such as site-directed mutagenesis or PCR. In one example, such variants can be readily selected by testing antibody cross-reactivity or its ability to induce an immune response. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Premembrane (prM) protein: A flavivirus structural protein. The prM protein is an approximately 25 kDa protein that is the intracellular precursor for the membrane (M) protein. prM is believed to stabilize the E protein during transport of the immature virion to the cell surface. When the virus exits the infected cell, the prM protein is cleaved to the mature M protein, which is part of the viral envelope (Reviewed in Lindenbach and Rice, In: *Fields Virology*, Knipe and Howley, eds., Lippincott, Williams, and Wilkins, 991-1041, 2001).

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of one or more signs or symptoms of a disease.

Recombinant: A recombinant nucleic acid, protein or virus is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques. The term recombinant includes nucleic acids, proteins and viruses that have been altered solely by addition, substitution, or deletion of a portion of a natural nucleic acid molecule, protein or virus.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Subject: Living multi-cellular vertebrate organisms, a category that includes both human and non-human mammals (such as mice, rats, rabbits, sheep, horses, cows, and non-human primates).

Therapeutically effective amount: A quantity of a specified agent (such as an immunogenic composition) sufficient to achieve a desired effect in a subject being treated with that agent. For example, this may be the amount of a virus vaccine useful for eliciting an immune response in a subject and/or for preventing infection by the virus. In the context of the present disclosure, a therapeutically effective amount of a dengue virus vaccine, for example, is an amount sufficient to increase resistance to, prevent, ameliorate, and/or treat infection caused by a dengue virus in a subject without causing a substantial cytotoxic effect in the subject. The effective amount of a dengue virus immune stimulating composition useful for increasing resistance to, preventing, ameliorating, and/or treating infection in a subject will be dependent on, for example, the subject being treated, the manner of administration of the therapeutic composition and other factors.

Vaccine: A preparation of immunogenic material capable of stimulating an immune response, administered for the prevention, amelioration, or treatment of infectious or other types of disease. The immunogenic material may include attenuated or killed microorganisms (such as bacteria or viruses), or antigenic proteins (including VLPs), peptides or DNA derived from them. An attenuated vaccine is a virulent organism that has been modified to produce a less virulent form, but nevertheless retains the ability to elicit antibodies and cell-mediated immunity against the virulent form. A killed vaccine is a previously virulent microorganism that has been killed with chemicals or heat, but elicits antibodies against the virulent microorganism. Vaccines may elicit both prophylactic (preventative) and therapeutic responses. Methods of administration vary according to the vaccine, but may include inoculation, ingestion, inhalation or other forms of administration. Vaccines may be administered with an adjuvant to boost the immune response.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. An insertional vector is capable of inserting itself into a host nucleic acid. A vector can also include one or more selectable marker genes and other genetic elements. An expression vector is a vector that contains the necessary regulatory sequences to allow transcription and translation of inserted gene or genes.

Virus-like particle (VLP): Virus particles made up of one of more viral structural proteins, but lacking the viral genome. Because VLPs lack a viral genome, they are non-infectious. In some embodiments, the VLPs are flavivirus VLPs, such as dengue VLPs. In particular examples, flavivirus VLPs include two flavivirus structural proteins—prM and E.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

Dengue viruses (DENV) are the most important mosquito transmitted viral pathogens infecting humans. Nearly half of the world's population lives in DENV endemic regions and millions of infections and many thousands of deaths occur annually. DENV infection produces a spectrum of disease, most commonly causing a self-limiting flu-like illness known as dengue fever, yet with increased frequency manifesting as life-threatening dengue hemorrhagic fever (DHF). Dengue immune responses are both protective and pathogenic as immunity to one of the four dengue serotypes can enhance subsequent infection with another serotype to produce DHF. Decades of effort to develop safe and efficacious dengue vaccines remain unsuccessful, primarily due to imbalanced immunity and concern that such imbalances could leave vaccinees not only unprotected but with increased susceptibility to enhanced disease.

Described herein is the development of a DENV serotype 1 (DENV-1) DNA vaccine with the immunodominant cross-reactive epitopes associated with immune enhancement removed. Comparison of the wild-type with this cross-reactivity reduced (CRR) vaccine demonstrated that both vaccines are equally protective against lethal homologous virus challenge. Under conditions simulating natural exposure during the inter-vaccine boost period prior to acquiring balanced protective immunity, wild-type vaccinated mice enhanced a normally sub-lethal heterologous DENV-2 infection resulting in DHF-like disease and 95% mortality. However, CRR vaccinated mice did not produce immunodominant cross-reactive enhancing antibodies, they exhibited redirected serotype-specific and protective immunity, and significantly reduced morbidity and mortality not differing from naïve mice in response to sub-lethal challenge. Thus, these data demonstrate that in an in vivo DENV disease model, non-protective vaccine-induced immunity can prime vaccinees for enhanced DHF-like disease and that CRR DNA immunization significantly reduces this vaccine safety concern. The sculpting of immune memory by the modified vaccine and resulting redirection of immunity hold great promise for developing novel vaccine prime-boost strategies against multi-strain pathogens such as DENV where vaccines remain elusive.

IV. Overview of Several Embodiments

Disclosed herein are dengue virus E-glycoprotein polypeptides containing mutations that eliminate immunodominant cross-reactive epitopes associated with immune enhancement. In some cases, the dengue virus E-glycoproteins further include mutations that introduce a strong CD4 T cell epitope. The disclosed E-glycoprotein polypeptides, or nucleic acid molecules encoding the polypeptides, can be used, for example, in monovalent or tetravalent vaccines against dengue virus. In some embodiments, the dengue virus E-glycoprotein is not a DENV-2 E-glycoprotein.

Provided herein are cross-reactivity reduced dengue virus E-glycoprotein polypeptides having amino acid substitutions at residues corresponding to positions 106, 107, 310 and 311, and either position 364 or position 389 of dengue serotype 1 (DENV-1) E-glycoprotein (SEQ ID NO: 1). The provided E-glycoprotein polypeptides optionally further include mutations corresponding to positions 468, 478, 482 and 487 of DENV-1 E-glycoprotein (SEQ ID NO: 1). The mutations at positions 468, 478, 482 and 487 of SEQ ID NO: 1 occur in the C-terminal region of the protein which is derived from JEV.

In some embodiments, provided herein is an isolated cross-reactivity reduced dengue virus E-glycoprotein polypeptide, wherein the polypeptide is selected from (1) a dengue serotype 1 virus (DENV-1) E-glycoprotein polypeptide comprising an arginine at position 106, an aspartic acid at position 107, an aspartic acid at position 310, a lysine at position 311, a glutamine at position 364, an isoleucine at position 468, a threonine at position 478, a valine at position 482 and a leucine at position 487, numbered with reference to SEQ ID NO: 1; (2) a dengue serotype 2 virus (DENV-2) E-glycoprotein polypeptide comprising an arginine at position 106, an aspartic acid at position 107, an glutamic acid at position 310, an arginine at position 311, an arginine at position 364, an isoleucine at position 468, a threonine at position 478, a valine at position 482 and a leucine at position 487, numbered with reference to SEQ ID NO: 2; (3) a dengue serotype 3 virus (DENV-3) E-glycoprotein polypeptide comprising an aspartic acid at position 106, an aspartic acid at position 107, an aspartic acid at position 308, a lysine at position 309, an aspartic acid at position 362, an isoleucine at position 466, a threonine at position 476, a valine at position 480 and a leucine at position 485, numbered with reference to SEQ ID NO: 3; and (4) a dengue serotype 4 virus (DENV-4) E-glycoprotein polypeptide comprising a glutamic acid at position 106, an aspartic acid at position 107, an aspartic acid at position 310, a glutamine at position 311, a glutamine at position 389, an isoleucine at position 468, a threonine at position 478, a valine at position 482 and a leucine at position 487, numbered with reference to SEQ ID NO: 4.

The mutations at positions 468, 478, 482 and 487 of SEQ ID NO: 1; positions 466, 476, 480 and 485 of SEQ ID NO: 3; and positions 468, 478, 482 and 487 of SEQ ID NO: 4 occur in the C-terminal region of each protein, which is derived from JEV (see Example 1).

In particular embodiments, the amino acid sequence of the polypeptide is at least 95%, at least 96%, at least 97%, at least 98% or at least 99% identical to SEQ ID NO: 1, wherein the polypeptide comprises an arginine at position 106, an aspartic acid at position 107, an aspartic acid at position 310, a lysine at position 311, a glutamine at position 364, an isoleucine at position 468, a threonine at position 478, a valine at position 482 and a leucine at position 487 of SEQ ID NO: 1. In some examples, the amino acid sequence of the polypeptide comprises SEQ ID NO: 1.

In other particular embodiments, the amino acid sequence of the polypeptide is at least 95%, at least 96%, at least 97%, at least 98% or at least 99% identical to SEQ ID NO: 2, wherein the polypeptide comprises an arginine at position 106, an aspartic acid at position 107, an glutamic acid at position 310, an arginine at position 311, an arginine at position 364, an isoleucine at position 468, a threonine at position 478, a valine at position 482 and a leucine at position 487 of SEQ ID NO: 2. In some examples, the amino acid sequence of the polypeptide comprises SEQ ID NO: 2.

In other particular embodiments, the amino acid sequence of the polypeptide is at least 95%, at least 96%, at least 97%, at least 98% or at least 99% identical to SEQ ID NO: 3, wherein the polypeptide comprises an aspartic acid at position 106, an aspartic acid at position 107, an aspartic acid at position 308, a lysine at position 309, an aspartic acid at position 362, an isoleucine at position 466, a threonine at position 476, a valine at position 480 and a leucine at position 485 of SEQ ID NO: 3. In some examples, the amino acid sequence of the polypeptide comprises SEQ ID NO: 3.

In yet other particular embodiments, the amino acid sequence of the polypeptide is at least 95%, at least 96%, at least 97%, at least 98% or at least 99% identical to SEQ ID NO: 4, wherein the polypeptide comprises a glutamic acid at position 106, an aspartic acid at position 107, an aspartic acid at position 310, a glutamine at position 311, a glutamine at position 389, an isoleucine at position 468, a threonine at position 478, a valine at position 482 and a leucine at position 487 of SEQ ID NO: 4. In some examples, the amino acid sequence of comprises SEQ ID NO: 4.

Also provided are isolated dengue virus-like particles (VLPs) comprising the cross-reactivity reduced dengue virus E-glycoprotein disclosed herein. In some embodiments, the VLP further includes a dengue virus prM protein. The VLP can optionally further include a dengue virus C protein.

Further provided are recombinant nucleic acid molecules encoding a cross-reactivity reduced dengue virus E-glycoprotein disclosed herein, or encoding a VLP containing a cross-reactivity reduced dengue virus E-glycoprotein. In some embodiments, the recombinant nucleic acid molecule comprises a nucleotide sequence at least 80%, at least 85%, at least 90%, at least 95%, at least 96%, at least 97%, at least 98% or at least 99% identical to SEQ ID NO: 9, SEQ ID NO: 10, SEQ ID NO: 11 or SEQ ID NO: 12. In particular examples, the recombinant nucleic acid molecule comprises the nucleotide sequence of SEQ ID NO: 9, SEQ ID NO: 10, SEQ ID NO: 11 or SEQ ID NO: 12.

Also provided are vectors comprising the recombinant nucleic acid molecules disclosed herein, and isolated cells comprising such vectors.

Compositions, such as immune stimulating compositions, are further provided by the present disclosure. In some embodiments, the compositions include a cross-reactivity reduced dengue virus E-glycoprotein polypeptide, a VLP comprising a cross-reactivity reduced dengue virus E-glycoprotein polypeptide, a recombinant nucleic acid molecule encoding a cross-reactivity reduced dengue virus E-glycoprotein polypeptide, or a vector encoding a cross-reactivity reduced dengue virus E-glycoprotein polypeptide or encoding a VLP comprising the cross-reactivity reduced polypeptide, and a pharmaceutically acceptable carrier. In some embodiments, the composition further includes an adjuvant.

Further provided is a tetravalent dengue virus vaccine. In some embodiments, the tetravalent dengue virus vaccine comprises a plurality of recombinant nucleic acid molecules, each encoding a cross-reactivity reduced dengue virus E-glycoprotein polypeptide from a different dengue virus serotype. In some examples, the tetravalent dengue virus vaccine comprises a recombinant nucleic acid molecule encoding the DENV-1 polypeptide of SEQ ID NO: 1, a recombinant nucleic acid molecule encoding the DENV-2 polypeptide of SEQ ID NO: 2, a recombinant nucleic acid molecule encoding the DENV-3 polypeptide of SEQ ID NO: 3, and a recombinant nucleic acid molecule encoding the DENV-4 polypeptide of SEQ ID NO: 4.

The present disclosure also provides methods of eliciting an immune response in a subject against dengue virus. In some embodiments, the method includes administering to the subject a therapeutically effective amount of a polypeptide, VLP, nucleic acid molecule, vector, composition or vaccine as disclosed herein. In some embodiments, the subject is a mammal, such as a human.

Also provided herein are compositions comprising a DENV-1 E-glycoprotein polypeptide, a DENV-2 E-glycoprotein polypeptide, a DENV-3 E-glycoprotein polypeptide and a DENV-4 E-glycoprotein polypeptide; or a recombinant nucleic acid molecule encoding the DENV-1 E-glycoprotein polypeptide, a recombinant nucleic acid molecule encoding the DENV-2 E-glycoprotein polypeptide, a recombinant nucleic acid molecule encoding the DENV-3 E-glycoprotein polypeptide and a recombinant nucleic acid molecule encoding the DENV-4 E-glycoprotein polypeptide, wherein:

(1) the DENV-1 E-glycoprotein polypeptide comprises an arginine at position 106, an aspartic acid at position 107, an aspartic acid at position 310, a lysine at position 311, a glutamine at position 364, an isoleucine at position 468, a threonine at position 478, a valine at position 482 and a leucine at position 487, numbered with reference to SEQ ID NO: 1;

(2) the DENV-2 E-glycoprotein polypeptide comprises an arginine at position 106, an aspartic acid at position 107, an glutamic acid at position 310, an arginine at position 311, an arginine at position 364, an isoleucine at position 468, a threonine at position 478, a valine at position 482 and a leucine at position 487, numbered with reference to SEQ ID NO: 2;

(3) the DENV-3 E-glycoprotein polypeptide comprises an aspartic acid at position 106, an aspartic acid at position 107, an aspartic acid at position 308, a lysine at position 309, an aspartic acid at position 362, an isoleucine at position 466, a threonine at position 476, a valine at position 480 and a leucine at position 485, numbered with reference to SEQ ID NO: 3; and/or (4) the DENV-4 E-glycoprotein polypeptide comprises a glutamic acid at position 106, an aspartic acid at position 107, an aspartic acid at position 310, a glutamine at position 311, a glutamine at position 389, an isoleucine at position 468, a threonine at position 478, a valine at position 482 and a leucine at position 487, numbered with reference to SEQ ID NO: 4.

In some embodiments, provided herein is a composition in which (1) the amino acid sequence of the DENV-1 polypeptide is at least 95%, at least 96%, at least 97%, at least 98% or at least 99% identical to SEQ ID NO: 1, and wherein the polypeptide comprises an arginine at position 106, an aspartic acid at position 107, an aspartic acid at position 310, a lysine at position 311, a glutamine at position 364, an isoleucine at position 468, a threonine at position 478, a valine at position 482 and a leucine at position 487 of SEQ ID NO: 1; (2) the amino acid sequence of the DENV-2 polypeptide is at least 95%, at least 96%, at least 97%, at least 98% or at least 99% identical to SEQ ID NO: 2, and wherein the polypeptide comprises an arginine at position 106, an aspartic acid at position 107, an glutamic acid at position 310, an arginine at position 311, an arginine at position 364, an isoleucine at position 468, a threonine at position 478, a valine at position 482 and a leucine at position 487 of SEQ ID NO: 2; (3) the amino acid sequence of the DENV-3 polypeptide is at least 95%, at least 96%, at least 97%, at least 98% or at least 99% identical to SEQ ID NO: 3, and wherein the polypeptide comprises an aspartic acid at position 106, an aspartic acid at position 107, an aspartic acid at position 308, a lysine at position 309, an aspartic acid at position 362, an isoleucine at position 466, a threonine at position 476, a valine at position 480 and a leucine at position 485 of SEQ ID NO: 3; and/or (4) the amino acid sequence of the DENV-4 polypeptide is at least 95%, at least 96%, at least 97%, at least 98% or at least 99% identical to SEQ ID NO: 4, and wherein the polypeptide comprises a glutamic acid at position 106, an aspartic acid at position 107, an aspartic acid at position 310, a glutamine at position 311, a glutamine at position 389, an isoleucine at position 468, a threonine at position 478, a valine at position 482 and a leucine at position 487 of SEQ ID NO: 4.

In particular examples, the DENV-1 polypeptide comprises the amino acid sequence of SEQ ID NO: 1, the DENV-2 polypeptide comprises the amino acid sequence of SEQ ID NO: 2, the DENV-3 polypeptide comprises the amino acid sequence of SEQ ID NO: 3 and/or the DENV-4 polypeptide comprises the amino acid sequence of SEQ ID NO: 4.

Further provided is a method of eliciting an immune response in a subject against dengue virus by administering to the subject a therapeutically effective amount of a composition comprising a DENV-1 E-glycoprotein polypeptide, a DENV-2 E-glycoprotein polypeptide, a DENV-3 E-glycoprotein polypeptide and a DENV-4 E-glycoprotein polypeptide; or a recombinant nucleic acid molecule encoding the DENV-1 E-glycoprotein polypeptide, a recombinant nucleic acid molecule encoding the DENV-2 E-glycoprotein polypeptide, a recombinant nucleic acid molecule encoding the DENV-3 E-glycoprotein polypeptide and a recombinant nucleic acid molecule encoding the DENV-4 E-glycoprotein polypeptide. In some examples, the method includes administering a DNA vaccine (such as a vaccine comprising recombinant nucleic acid molecules encoding cross-reactivity reduced dengue virus E-glycoproteins from each of DENV-1, DENV-2, DENV-3 and DENV-4), followed by administering a protein booster vaccine (such as a vaccine including recombinant, inactivated virus, or live attenuated virus).

V. Cross-Reactivity Reduced Dengue Virus E-Glycoprotein Polypeptides

Provided by the present disclosure are cross-reactivity reduced dengue virus E-glycoprotein polypeptides in which immunodominant epitopes associated with immune enhancement have been removed by select amino acid substitutions. In particular, for each serotype of dengue virus, amino acid substitutions were made at residues corresponding to positions 106, 107, 310, 311 and 364 of DENV-1 (SEQ ID NO: 1), with the exception that the DENV-4 E-glycoprotein includes a mutation at position 389 instead of position 364. The cross-reactivity reduced E-glycoproteins provided herein were based on extensive mutagenesis studies to select the best mutation site as measured by the highest reduction on complex cross-reactive monoclonal antibody binding. These studies revealed that for DENV-4, mutation at residue 389 reduced antibody binding to a much greater degree than mutation at position 364 (which is located structurally very close to residue 389). Thus, mutation at 389 was selected for this serotype. In addition, because the E-glycoprotein of DENV-3 is two amino acids shorter than the E protein from the remaining serotypes, the mutations in the DENV-3 E-glycoprotein occur at positions 106, 107, 308, 309 and 362 (SEQ ID NO: 3).

In some instances, the amino acid substituted for each dengue serotype at each position varies. The specific residues at each position were selected to enhance or maintain antigen secretion.

In some embodiments, the dengue virus E-glycoprotein polypeptides further contain a potent CD4 T cell epitope identified in the transmembrane domain of the E-glycoprotein of West Nile virus. To insert the CD4 T cell epitope, mutations were made at residues 468 (valine to isoleucine), 478 (alanine to threonine), 482 (threonine to valine) and 487 (valine to leucine) for DENV-1, DENV-2 and DENV-4 E protein (SEQ ID NOs: 1, 2 and 4), which corresponded to 466 (valine to isoleucine), 476 (alanine to threonine), 480 (threonine to valine) and 485 (valine to leucine) for DENV-3 E protein.

Provided herein are dengue virus E-glycoprotein polypeptides comprising the following mutations:

| DENV-1 SEQ ID NO: 1 | DENV-2 SEQ ID NO: 2 | DENV-3 SEQ ID NO: 3 | DENV-4 SEQ ID NO: 4 |
|---|---|---|---|
| G106R | G106R | G106D | G106E |
| L107D | L107D | L107D | L107D |
| K310D | K310E | K308D | K310D |
| E311K | E311R | E309K | E311Q |
| P364Q | P364R | P362D | L389Q |
| V468I | V468I | V466I | V468I |
| A478T | A478T | A476T | A478T |
| T482V | T482V | T480V | T482V |
| V487L | V487L | V485L | V487L |

In some embodiments of the present disclosure, the dengue virus E-glycoprotein is at least 80%, at least 85%, at least 90%, at least 95%, at least 96%, at least 97%, at least 98% or at least 99% identical to SEQ ID NO: 1, wherein the polypeptide comprises an arginine at position 106, an aspartic acid at position 107, an aspartic acid at position 310, a lysine at position 311, a glutamine at position 364, an isoleucine at position 468, a threonine at position 478, a valine at position 482 and a leucine at position 487 of SEQ ID NO: 1; or is at least 80%, at least 85%, at least 90%, at least 95%, at least 96%, at least 97%, at least 98% or at least 99% identical to SEQ ID NO: 2, wherein the polypeptide comprises an arginine at position 106, an aspartic acid at position 107, an glutamic acid at position 310, an arginine at position 311, an arginine at position 364, an isoleucine at position 468, a threonine at position 478, a valine at position 482 and a leucine at position 487 of SEQ ID NO: 2; or is at least 80%, at least 85%, at least 90%, at least 95%, at least 96%, at least 97%, at least 98% or at least 99% identical to SEQ ID NO: 3, wherein the polypeptide comprises an aspartic acid at position 106, an aspartic acid at position 107, an aspartic acid at position 308, a lysine at position 309, an aspartic acid at position 362, an isoleucine at position 466, a threonine at position 476, a valine at position 480 and a leucine at position 485 of SEQ ID NO: 3; or is at least 80%, at least 85%, at least 90%, at least 95%, at least 96%, at least 97%, at least 98% or at least 99% identical to SEQ ID NO: 4, and wherein the polypeptide comprises a glutamic acid at position 106, an aspartic acid at position 107, an aspartic acid at position 310, a glutamine at position 311, a glutamine at position 389, an isoleucine at position 468, a threonine at position 478, a valine at position 482 and a leucine at position 487 of SEQ ID NO: 4.

In specific non-limiting examples, the amino acid sequence of the cross-reactivity reduced dengue virus E-glycoprotein comprises SEQ ID NO: 1, SEQ ID NO: 2, SEQ ID NO: 3 or SEQ ID NO: 4.

VI. Immunostimulatory Compositions and Administration Thereof

The immunostimulatory compositions provided herein can include, for example, a cross-reactivity reduced dengue virus E-glycoprotein polypeptide, a recombinant nucleic acid molecule encoding a cross-reactivity reduced dengue virus E-glycoprotein polypeptide, a VLP comprising a cross-reactivity reduced dengue virus E-glycoprotein polypeptide, or a recombinant nucleic acid molecule (such as a vector) encoding a VLP. In some cases, the immunostimulatory compositions are monovalent vaccines for dengue virus (i.e. contain E-glycoprotein from a single serotype of dengue virus). In other instances, the immunostimulatory compositions are tetravalent vaccines for dengue virus (i.e. contain E-glycoprotein from all four dengue virus serotypes).

The cross-reactivity reduced dengue virus E-glycoprotein polypeptides and VLPs (including nucleic acid molecules encoding the cross-reactivity reduced dengue virus polypeptides and VLPs) disclosed herein can be used as dengue virus vaccines to elicit an immune response, such as a protective immune response, against dengue virus.

The provided immunostimulatory dengue virus polypeptides, constructs or vectors encoding such polypeptides, are combined with a pharmaceutically acceptable carrier or vehicle for administration as an immune stimulatory composition to human or animal subjects. In a particular embodiment, the immune stimulatory composition administered to a subject directs the synthesis of a dengue virus E-glycoprotein as described herein, and a cell within the body of the subject, after incorporating the nucleic acid within it, secretes VLPs comprising the E-glycoprotein. It is believed that such VLPs then serve as an in vivo immune stimulatory composition, stimulating the immune system of the subject to generate protective immunological responses. In some embodiments, more than one immune stimulatory dengue virus polypeptide, construct or vector may be combined to form a single preparation.

The immunogenic formulations may be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of a sterile liquid carrier, for example, water for injections, immediately prior to use. Extemporaneous injection solutions and suspensions may be prepared from sterile powders, granules and tablets commonly used by one of ordinary skill in the art.

In certain embodiments, unit dosage formulations are those containing a dose or unit, or an appropriate fraction thereof, of the administered ingredient. It should be understood that in addition to the ingredients particularly mentioned above, formulations encompassed herein may include other agents commonly used by one of ordinary skill in the art.

The compositions provided herein, including those for use as immune stimulatory compositions, may be administered through different routes, such as oral, including buccal and sublingual, rectal, parenteral, aerosol, nasal, intramuscular, subcutaneous, intradermal, and topical. They may be administered in different forms, including but not limited to solutions, emulsions and suspensions, microspheres, particles, microparticles, nanoparticles, and liposomes.

The volume of administration will vary depending on the route of administration. By way of example, intramuscular injections may range from about 0.1 ml to about 1.0 ml. Those of ordinary skill in the art will know appropriate volumes for different routes of administration.

Immune stimulatory compounds (for example, vaccines) can be administered by directly injecting nucleic acid molecules encoding peptide antigens (broadly described in Janeway & Travers, *Immunobiology: The Immune System In Health and Disease*, page 13.25, Garland Publishing, Inc., New York, 1997; and McDonnell & Askari, *N. Engl. J. Med.* 334:42-45, 1996). Vectors that include nucleic acid molecules described herein, or that include a nucleic acid sequence encoding a dengue virus E-glycoprotein polypeptide may be utilized in such DNA vaccination methods.

Thus, the term "immune stimulatory composition" as used herein also includes nucleic acid vaccines in which a nucleic acid molecule encoding a cross-reactivity reduced dengue virus E-glycoprotein polypeptide is administered to a subject in a pharmaceutical composition. For genetic immunization, suitable delivery methods known to those skilled in the art include direct injection of plasmid DNA into muscles (Wolff et al., *Hum. Mol. Genet.* 1:363, 1992), delivery of DNA complexed with specific protein carriers (Wu et al., *J. Biol. Chem.* 264:16985, 1989), co-precipitation of DNA with calcium phosphate (Benvenisty and Reshef, *Proc. Natl. Acad. Sci.* 83:9551, 1986), encapsulation of DNA in liposomes (Kaneda et al., *Science* 243:375, 1989), particle bombardment (Tang et al., *Nature* 356:152, 1992; Eisenbraun et al., *DNA Cell Biol.* 12:791, 1993), and in vivo infection using cloned retroviral vectors (Seeger et al., *Proc. Natl. Acad. Sci.* 81:5849, 1984). Similarly, nucleic acid vaccine preparations can be administered via viral carrier.

The amount of immunostimulatory compound in each dose of an immune stimulatory composition is selected as an amount that induces an immunostimulatory or immunoprotective response without significant, adverse side effects. Such amount will vary depending upon which specific immunogen is employed and how it is presented. Initial injections may range from about 1 μg to about 1 mg, with some embodiments having a range of about 10 μg to about 800 and still other embodiments a range of from about 25 μg to about 500 μg. Following an initial administration of the immune stimulatory composition, subjects may receive one or several booster administrations, adequately spaced. Booster administrations may range from about 1 μg to about 1 mg, with other embodiments having a range of about 10 μg to about 750 μg, and still others a range of about 50 μg to about 500 μg. Periodic boosters at intervals of 1-5 years, for instance three years, may be desirable to maintain the desired levels of protective immunity.

In some embodiments, a subject receives a DNA prime vaccination, for example, a nucleic acid molecule (such as a vector) encoding a dengue virus E-glycoprotein polypeptide described herein, and subsequently receives a protein boost vaccination (such as recombinant, inactivated virus, or live attenuated virus). DNA prime-protein boost strategies for dengue virus are discussed further in section IX below.

Dengue virus polypeptides or VLPs (or nucleic acid molecules encoding dengue virus polypeptides or VLPs), or compositions thereof, are administered in any suitable manner, such as with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Particular methods for administering nucleic acid molecules are well known in the art. In some examples, the nucleic acid encoding the dengue virus polypeptide or VLP is administered by injection (such as intramuscular or intradermal injection) or by gene gun.

Administration can be accomplished by single or multiple doses. The dose administered to a subject in the context of the present disclosure should be sufficient to induce a beneficial therapeutic response in a subject over time, or to inhibit or prevent flavivirus infection. The dose required will vary from subject to subject depending on the species, age, weight and general condition of the subject, the severity of the infection being treated, the particular composition being used and its mode of administration. An appropriate dose can be determined by one of ordinary skill in the art using only routine experimentation.

The pharmaceutical or immune stimulatory compositions or methods of treatment may be administered in combination with other therapeutic treatments. For example, the compositions provided herein can be administered with an adjuvant, such as Freund incomplete adjuvant or Freund's complete adjuvant.

Optionally, one or more cytokines, such as IL-2, IL-6, IL-12, RANTES, GM-CSF, TNF-α, or IFN-γ, one or more growth factors, such as GM-CSF or G-CSF; one or more molecules such as OX-40L or 41 BBL, or combinations of these molecules, can be used as biological adjuvants (see, for example, Salgaller et al., 1998, *J. Surg. Oncol.* 68(2): 122-38; Lotze et al., 2000, *Cancer J. Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90). These molecules can be administered systemically (or locally) to the host.

VII. Immune Enhancement Following Heterologous DENV Exposure

The most significant risk factor for severe dengue disease is secondary infection with a heterologous serotype (Murphy and Whitehead, *Annu Rev Immunol* 29:587-619, 2011). Two distinct yet not mutually exclusive mechanisms for immune enhancement upon heterologous exposure explain the pathogenic manifestations characterizing DHF/DSS. The leading hypothesis is that DHF occurs via antibody-dependent enhancement (ADE) of infection, a phenomenon originally described for flaviviruses but later found to occur with diverse pathogens (Hawkes, *Aust J Exp Biol Med Sci* 42:465-482, 1964; Halstead, *Rev Infect Dis* 11 Suppl 4:S830-839, 1989; Morens, *Clin Infect Dis* 19:500-512, 1994; Thomas et al., *Expert Rev Vaccines* 5:409-412, 2006). Preexisting cross-reactive antibodies from a previous infection (or maternal antibodies in infants) recognize and bind to heterologous virus in a secondary infection, yet are unable to neutralize this virus, either because they are non-neutralizing, or for a lack of sufficient avidity or occupancy (Pierson et al., *Cell Host Microbe* 4:229-238, 2008). However, these non-neutralizing antibody-virus complexes increase the infection of monocytes via their Fc receptors, dramatically increasing viral replication and load, thereby causing DHF.

Moreover, recent studies additionally implicate an important role for altered intracellular signaling enhancing ADE effects by suppressing innate antiviral protein responses (Thomas et al., *Expert Rev Vaccines* 5:409-412, 2006; Mahalingam and Lidbury, *Proc Natl Acad Sci USA* 99:13819-13824, 2002). Weakly- and non-neutralizing cross-reactive antibodies induced from immunodominant B-cell epitopes are known to make up the majority of the humoral immune response to DENV infection (Lai et al., *J Virol.* 82(13):6631-6643, 2008; Crill et al., *PLoS ONE* 4:e4991, 2009). Although there are now numerous reports of in vitro ADE of DENV infection, ADE has not been demonstrated to occur in humans or to cause DHF, yet recent studies provide strong support for an in vivo role for ADE in human DHF. The majority of the rare cases of primary DHF infections occur in infants born to DENV immune mothers and in one study the age at which infants acquired DHF correlated with predicted age of maximal in vitro enhancement (Kliks et al., *Am J Trop Med Hyg* 38:411-419, 1988). A prospective study conducted in Vietnam indicated that the in vitro enhancing capability of maternally derived infant antibody in pre-exposure sera correlated with subsequent DENV disease severity (Chau et al., *J Infect Dis* 198:516-524, 2008). In a recently developed type I/type II IFN receptor knock-out mouse model (AG129) of DENV disease (Williams et al., *Ann N Y Acad Sci* 1171 Suppl 1:E12-23, 2009), sub-neutralizing levels of homologous or heterologous DENV immune mouse sera (Zellweger et al., *Cell Host Microbe* 7(2):128-139, 2010; Balsitis et al., *PLoS Pathog* 6:e1000790, 2010) or cross-reactive human MAbs (Beltramello et al., *Cell Host Microbe* 8:271-283, 2010) enhanced viral replication in vivo producing a DHF-type disease.

The second, related mechanism of immune enhanced DENV pathology, also a generalized phenomenon, posits that there is a highly skewed cellular response to heterologous DENV infection driven by low affinity, cross-reactive memory CD4+ and CD8+ T cells (Brehm et al., *Nat Immunol* 3:627-634, 2002; Welsh and Selin, *Nat Rev Immunol* 2:417-426, 2002; Welsh et al., *Annu Rev Immunol* 22:711-743, 2004). During primary DENV infection cross-reactive and serotype-specific T cell clones are selected for increasing affinity to the infecting DENV serotype. Upon heterologous infection these pre-existing memory T cells with reduced affinity for the secondarily infecting serotype dominate the immune response relative to higher affinity T cells specific for the currently infecting virus (Rothman, *J Clin Invest* 113:946-951, 2004). The domination of lower affinity clones in secondary response appears to be due to both the preferential expansion of cross-reactive T cells originated from the primary infection and from apoptosis of high-affinity secondarily stimulated T cells induced by the high antigenic loads associated with secondary infection (Combadiere et al., *J Exp Med* 187:349-355, 1998; Mongkolsapaya et al., *Nat Med* 9:921-927, 2003). Both processes result in T cell populations inefficient at viral clearance.

Moreover, additional evidence suggests that such low affinity anamnestically stimulated T cells contribute to DENV immunopathology by their continued secretion of pro-inflammatory cytokines and vasoactive mediators causing the increased vascular permeability and hemorrhagic manifestations characterizing DHF/DSS (Welsh and Selin, *Nat Rev Immunol* 2:417-426, 2002; Mangada and Rothman, *J Immunol* 175:2676-2683, 2005; Mongkolsapaya et al., *J Immunol* 176:3821-3829, 2006). Cross-reactive T cell epitopes have been identified across the DENV proteome, however, immunodominant CD8+ T cell epitopes in non-structural protein NS3 appear to be those most strongly associated with DHF (Mathew and Rothman, *Immunol Rev* 225:300-313, 2008; Friberg et al., *Immunol Cell Biol* 89(1): 122-129, 2010; Duangchinda et al., *Proc Natl Acad Sci USA* 107(39):16922-16927, 2010).

The common theme throughout DENV immune enhancement is the concept of 'original antigenic sin' originally describing a phenomenon observed in response to influenza, it has since been found to be a generalized phenomenon (Francis, *Ann Intern Med* 39:203-221, 1953; Welsh and Fujinami, *Nat Rev Microbiol* 5:555-563, 2007). Original antigenic sin describes the shift in the immunodominance hierarchy that occurs when prior exposure to cross-reactive antigens alters and inhibits subsequent immune response to related antigens, either in new infections or through vaccination (Brehm et al., *Nat Immunol* 3:627-634, 2002). Both humoral and cellular responses can be plagued by such misdirected or inappropriate heterotypic immunity (Welsh and Fujinami, *Nat Rev Microbiol* 5:555-563, 2007). The phenomenon is most severe when the cross-reactive antigenic responses are immunodominant as is the case with both cellular and humoral DENV immunity. Thus, for DENV not only does original antigenic sin appear to play an important role in the more severe DENV pathologies but it also creates a vaccine safety issue as a lack of protective tetravalent vaccine induced immunity could prime vaccinees for DHF upon subsequent infection (Murphy and Whitehead, *Annu Rev Immunol* 29:587-619, 2011). Such caution is valid as a similar situation occurred when children immunized with inactivated respiratory syncytial virus vaccine suffered increased mortality when naturally exposed to RSV and the increased morbidity and mortality appeared to be due to both ADE and T cell induced cytokine immunopathology (Thomas et al., *Expert Rev Vaccines* 5:409-412, 2006; Kim et al., *Am J Epidemiol* 89:422-434, 1969).

Concerns for dengue vaccination priming individuals for severe disease via immune enhancement have necessitated the postulates that dengue vaccines must produce balanced, tetravalent, and protective immunity, optimally derived from a single dose providing long-lasting protection (Miller, *Curr Opin Mol Ther* 12:31-38, 2010; Murphy and Whitehead, *Annu Rev Immunol* 29:587-619, 2011). Because of the past experience of robust, long-term immunity derived from live yellow fever 17D vaccine and others, the majority of public health efforts have focused on the development of live-attenuated dengue vaccines (Durbin and Whitehead, *Curr*

*Top Microbiol Immunol* 338:129-143, 2009). Despite advancements over the past three decades, dengue vaccine development continues to face significant road blocks challenging the necessity of these historical postulates. Inducing a balanced, tetravalent, and protective immunity has been the biggest hurdle and remains largely unresolved in the time spans considered necessary, typically ≤3 months, the duration of the low transmission season in many endemic countries (Sun et al., *Hum Vaccin* 5:33-40, 2009; Morrison et al., *J Infect Dis* 201:370-377, 2010). Tetravalent live-replicating vaccines are susceptible to both replication and immune interference between different vaccine serotypes (Guy et al., *Am J Trop Med Hyg* 80:302-311, 2009). This phenomenon is both a biological and a stochastic process since the target cell number in the injection site is significantly lower than the total infectious virions in tetravalent DENV vaccine formulations. Resulting imbalances in serotype-specific immunity exacerbate concerns of vaccine-induced immune enhancement, regardless of its mechanistic basis, and this concern has not been addressed by existing dengue vaccine candidates in clinical trials (Miller, *Curr Opin Mol Ther* 12:31-38, 2010; Whitehead et al., *Nat Rev Microbiol* 5:518-528, 2007; Hatch et al., *IDrugs* 11:42-45, 2008).

The inventors have developed a vaccine platform specifically addressing these obstacles to DENV vaccine development. The DNA vaccine platform consists of an expression plasmid containing only the envelope (E, the primary protective antigen) and premembrane (prM) structural protein genes. Upon uptake by host cells the structural genes are transcribed and translated and the proteins self-assemble into virus-like particles (VLPs) which are antigenically indistinguishable from virus (Chang et al., *Ann N Y Acad Sci* 951:272-285, 2011; Chang et al., *Virology* 306:170-180, 2003). The wild-type (WT) flavivirus DNA vaccines are demonstrably safe, immunogenic, and protective against Japanese encephalitis, West Nile, and dengue viruses in both non-human animals (Chang et al., *Virology* 306:170-180, 2003; Mohageg et al., *Opt Express* 15:4869-4875, 2007; Davis et al., *J Virol* 75:4040-4047, 2001; Chang et al., *Vaccine* 25:2325-2330, 2007) and in humans (Martin et al., *J Infect Dis* 196:1732-1740, 2007). DNA vaccines have a number of advantages over other vaccine platforms. They can stimulate strong CD4+ T cell responses as do inactivated and subunit vaccines and yet also strongly stimulate CD8+ T cell responses similar to live attenuated vaccines (Martin et al., *J Infect Dis* 196:1732-1740, 2007; Laylor et al., *Clin Exp Immunol* 117:106-112, 2009). Because VLPs lack infectious RNA and are non-replicating, tetravalent dengue DNA vaccines do not suffer from the replication interference obstacles impeding the live-attenuated vaccine approaches (Laylor et al., *Clin Exp Immunol* 117:106-112, 2009; Petersen and Roehrig, *J Infect Dis* 196:1721-1723, 2007). Most importantly, unlike live viruses or the inactivated vaccines made from them, DNA vaccines can be readily manipulated and engineered to prime specific epitopes and redirect immune response away from immunodominant, pathogenic B cell and T cell epitopes. This sculpted immune memory priming can redirect subsequent vaccine boosts or natural exposure toward protective, DENV-specific epitopes increasing both vaccine safety and efficacy.

The present disclosure tackles the previously unaddressed concern of vaccine-induced predisposition to severe dengue disease via immune enhancement. Described is the introduction of substitutions into two distinct E protein antigenic regions of a DENV-1 DNA vaccine (pVD1) ablating cross-reactive, immunodominant, weakly or non-neutralizing B cell epitopes associated with immune enhancement (Crill et al., *PLoS ONE* 4:e4991, 2009), thereby reducing the potential for this cross-reactivity reduced vaccine (pVD1-CRR) to potentiate DHF via ADE. These CRR dengue vaccines are also less susceptible to heterologous immune enhancement via cross-reactive T cell induced "cytokine storm" mechanisms. Because they contain only the prM and E proteins, they lack entirely the well-characterized, immunodominant, DHF-associated CD 8+ T cell epitopes located in the NS3 protein. The results disclosed herein demonstrate that by priming the immune system with CRR dengue DNA vaccines, the immune landscape can be sculpted to increase protective DENV-specific neutralizing antibody responses and avoid anamnestic responses to cross-reactive enhancing epitopes that are inherent to other DENV vaccine approaches. In addition to DENV-1, corresponding mutations were made in the E-glycoproteins of DENV-2, DENV-3 and DENV-4; the sequences of these proteins are also provided herein.

VIII. Redirecting the Immune Response to DENV Vaccination

The present disclosure describes construction of wild-type (WT) and cross-reactivity reduced (CRR) DENV-1 DNA vaccine candidates and demonstrates that both WT and CRR vaccines stimulate similar levels of neutralizing antibodies. Moreover, immunized mice were equally protected from homologous DENV-1 virus challenge. The CRR vaccine candidate was specifically engineered to reduce the potential for vaccine-induced susceptibility to severe dengue disease, a theoretical safety concern that has hampered dengue vaccine development for decades (Murphy and Whitehead, *Annu Rev Immunol* 29:587-619, 2011). These results confirm, in an in vivo dengue disease model, that this vaccine safety issue is real and indicate that the disclosed CRR vaccine approach can resolve this long-standing, previously intractable roadblock to dengue vaccine development. It is demonstrated that by disrupting immunodominant, pathogenic epitopes, the immunodominance hierarchy can be redirected away from pathogenic toward normally subdominant, protective epitopes. Under conditions simulating natural exposure during the inter-vaccination boost period prior to achieving balanced protective immunity, WT vaccinated mice enhanced a heterologous, self-limiting, normally sub-lethal DENV-2 infection into a DHF-like disease pathology resulting in 95% mortality. CRR vaccinated mice however, lacked vaccine-induced immunodominant enhancing antibodies, exhibited increased dominance of protective, neutralizing immunoglobulins, and had significantly reduced morbidity and mortality that did not differ from naïve mice.

The finding of vaccine-induced severe dengue disease and mortality via ADE is consistent with and supported by two recent studies of ADE-induced dengue disease in AG129 mice using passive transfer of DENV immune sera (Zellweger et al., *Cell Host Microbe* 7(2):128-139, 2010; Balsitis et al., *PLoS Pathog* 6:e1000790, 2010). Using the same DENV-2 S221 virus as in the present study, these studies found that administering $10^4$, $10^5$, or $10^6$ pfu of DENV-2 S221 was sub-lethal to naïve AG129 mice receiving passively transferred normal mouse serum 24 hours prior to challenge. However, mice receiving heterologous DENV-1, -3, or -4 immune sera 24 hours prior to challenge died 4-5 DPC from severe dengue disease resembling DHF. The disease pathology observed in these studies was similar to that seen in human DHF and included vascular leak related pathology of the visceral organs, thrombocytopenia, elevated levels of pro-inflammatory cytokines, increased viremia, hepatitis, and increased virus replication in liver sinusoidal endothelial cells. Confirmation that this enhanced DHF-like disease and mortality resulted from ADE was supported by passive transfer of well-characterized enhancing $EDII_{FP}$ MAbs, and by rescue from enhanced mortality by passive transfer of an engineered $EDII_{FP}$ MAb unable to bind FcγR, thereby demonstrating that the enhanced disease pathology required FcγR interaction (Balsitis et al., *PLoS Pathog* 6:e1000790, 2010). In the present study, it was discovered that when exposed to normally sub-lethal doses of DENV-2 S221, pVD1-WT vaccinated mice suffered 95% mortality from ADE-induced DHF-like disease and that the enhanced disease pathology and mortality could be significantly reduced by immunization with a modified pVD1-CRR vaccine that did not stimulate immunodominant cross-reactive antibodies.

In humans, severe dengue disease is associated with 10-100 fold increases in viral loads compared to DF patients (Murphy and Whitehead, *Annu Rev Immunol* 29:587-619, 2011). A 100-fold greater increase in DENV-2 viremia of pVD1-WT vaccinated mice compared to pVD1-CRR vaccinated mice was observed. This 100-fold increase was similar to that observed in experimental models of ADE in Rhesus monkeys (Goncalvez et al., *Proc Natl Acad Sci USA* 104:9422-9427, 2007), 5-35 times higher than in passively transferred AG129 mice (Zellweger et al., *Cell Host Microbe* 7(2):128-139, 2010; Balsitis et al., *PLoS Pathog* 6:e1000790, 2010), and 10-fold greater than the increase in DHF patients relative to DF patients in a Thai study (Vaughn et al., *J Infect Dis* 181:2-9, 2000).

The present study also revealed a rapid induction of diverse DENV-2 neutralizing antibody populations by pVD1-CRR vaccinated mice in response to heterologous DENV-2 infection. It was hypothesized that the rapid rise in DENV-2 neutralizing antibody titers was due to an increased memory response to complex cross-reactive neutralizing antibodies recognizing epitopes not altered in the CRR vaccine, such as MAb 1B7, and to increased primary induction of DENV-2 serotype-specific potently neutralizing antibodies such as 9A3D-8 and 3H5. One explanation is that WT vaccinated mice would not have the immunological energy available to invest in such sub-dominate neutralizing antibody responses because of their immunodominant production of $EDII_{FP}$ and $EDIII_{CR}$ antibodies (original antigenic sin) whereas CRR vaccinated mice should have increased induction of such neutralizing antibody populations specifically because they lacked $EDII_{FP}$ and $EDIII_{CR}$ antibody priming. There was a very large increase in 1B7-like antibodies for CRR-vaccinated mice relative to WT vaccinated mice, supporting the importance of this class of neutralizing antibody. However, the majority of the large increase in DENV-2 neutralization by CRR vaccinated mice appears to be due to DENV-2 serotype-specific potently neutralizing antibody.

The concern of inappropriate vaccine-induced immunodominant antibody responses in dengue vaccinology and the approach described herein of genetically modifying these pathogenic epitopes to redirect the immunodominance hierarchy has parallels with other variable strain pathogens such as HIV and influenza. Both HIV and influenza vaccinology suffer from the plague of original antigenic sin and strain-specific immunodominance. For all of these viruses, producing efficacious vaccines requires altering the native, wild-type immune responses. In both HIV and influenza there has been much recent interest in this area of modifying immunogens to redirect immune responses, typically referred to as immune dampening and immune refocusing (Tobin et al., *Vaccine* 26:6189-6199, 2008). Some generalizations from this body of work are consistent with and support the CRR DENV DNA vaccination results. The dampening of immunodominant epitopes resulted in decreased induction of antibodies recognizing the targeted epitopes while increasing the amount of antibody stimulated from natively sub-dominant epitopes. Moreover, in spite of such major alterations in immunodominance hierarchies, antigenically modified immunogens induced similar total overall antibody titers as did WT immunogens. Together, these results imply that via a variety of approaches it is possible to successfully redirect vaccine-induced immune responses to sculpt original antigenic sin and improve safety and/or efficacy without altering overall vaccine immunogenicity.

IX. DNA Prime-Protein Boost Vaccine Strategies

There is substantial interest in utilizing heterologous vaccine prime-boost strategies to improve and broaden immunogenicity, especially in the context of DNA vaccination (Dale et al., *Methods Mol Med* 127:171-197, 2006; Guenaga et al., *PLoS ONE* 6:e16074, 2011; Ding et al., *PLoS ONE* 6:e16563, 2011; Chen et al., *J Virol* 81:11634-11639, 2007; Simmons et al., *Virology* 396:280-288, 2010). In this context, 'heterologous' typically refers to the use of different vaccine formats to present the same viral immunogen between prime and boost, most commonly DNA prime and protein (recombinant, inactivated virus, or live attenuated virus) boost. Much of this interest has also been directed toward HIV (Walker and Burton, *Curr Opin Immunol* 22:358-366, 2010) and influenza (Ding et al., *PLoS ONE* 6:e16563, 2011; Wei et al., *Science* 329:1060-1064, 2010) where the vaccine goal is to increase the breadth of neutralization and hence protection from these highly variable multi-strain pathogens. Because of the similarities to DENV and the difficulties of rapidly inducing balanced tetravalent immunity with current DENV live attenuated vaccines (Murphy and Whitehead, *Annu Rev Immunol* 29:587-619, 2011), DNA prime-protein boost strategies are particularly appealing to DENV vaccinology. Chen et al. compared monovalent DENV-1 prM/E DNA vaccination with that of a Venezuelan equine encephalitis viral replicon particle (VRP) delivering DENV-1 prM/E proteins in non-human primates. They found that DNA prime followed by VRP boost produced higher DENV-1 total IgG and neutralizing antibody titers than either DNA-DNA or VRP-VRP prime-boost strategies. Moreover, only the DNA-VRP prime-boost prevented viremia following DENV-1 challenge (Chen et al., *J Virol* 81:11634-11639, 2007). Simmons et al. examined tetravalent DNA, inactivated virus, and live attenuated DENV prime-boost schemes in non-human primates (Simmons et al., *Virology* 396:280-288, 2010). They found that tetravalent inactivated virus prime and tetravalent live attenuated virus (TLAV) boost produced the highest ELISA and neutralizing antibody titers and prevented detectable viremia following challenge while still inducing strong anamnestic increases in neutralizing antibody.

It was found that DENV-1 CRR DNA vaccination redirected subsequent immunity in response to DENV-2 challenge and increased the induction of a broad repertoire of neutralizing antibodies to produce a rapid, large magnitude DENV-2 neutralizing response with increased cross-neutralization to other DENV serotypes. These findings suggest that CRR DNA vaccines hold great potential for novel DENV vaccine strategies that take advantage of the benefits of both DNA and live attenuated virus vaccines. One such strategy is to prime hosts with a low-dose tetravalent CRR DNA vaccine to induce a balanced memory response with limited neutralizing antibody to each serotype. This priming should allow for efficient TLAV boost 1-2 months later to rapidly produce long-lasting, balanced, and protective tetravalent immunity with reduced virus enhancing capabilities. This vaccine strategy takes advantage of the strong T cell priming properties of DNA vaccines, the potent induction of long-lasting high-titer antibody responses of LAVs, and the improved safety and protective efficacy profile of the CRR modifications disclosed herein.

The following examples are provided to illustrate certain particular features and/or embodiments. These examples should not be construed to limit the disclosure to the particular features or embodiments described.

EXAMPLES

Example 1: Materials and Methods

This example describes the materials and experimental procedures used for the studies described in Example 2.

Vaccine Construction, Characterization, and Preparation

The construction of pVD1-WT and pVD1-CRR vaccine plasmids was the same as for DENV-2 DNA vaccine plasmids and has been previously described in detail (Crill et al., *PLoS ONE* 4:e4991, 2009; Chang et al., *Virology* 306:170-180, 2003). Briefly, pVD1-WT was constructed using DENV-1 strain (56)BC94/95 for cDNA cloning of premembrane (prM) and 80% DENV-1 envelope (E) with the C terminal 20% of the E protein replaced with the homologous region of Japanese encephalitis virus (JEV). 80% DENV-1 E corresponds to the ectodomain and the C terminal 20% corresponds to the helical stems (E-H1, E-H2) and transmembrane domain (TMD) anchor helices (E-T1, E-T2) (Zhang et al., *Nat Struct Biol* 10:907-912, 2003). In addition the pVD1-WT vaccine utilized in this study, and as the template for constructing pVD1-CRR, contained a potent CD4+ T cell TMD epitope identified in West Nile virus (WNV). The inclusion of this epitope into the DENV-2 DNA vaccine (pVD2) and into pVD2-CRR boosts the neutralizing antibody responses of vaccinated mice about 2-fold. Introduction of the WNV TMD CD4+ epitope into pVD1 required introducing four amino acid substitutions (V474I, A484T, T488V, and V493L) into the C terminal 20% JEV sequence of pVD1.

pVD1-CRR was constructed using pVD1-WT as the DNA template and the primers listed in Table 1, and with Stratagene Quick Change® multi-site-directed mutagenesis kit (Stratagene, La Jolla, Calif.) following the manufacturer's recommended protocols. Structural gene regions and regulatory elements of all plasmids were sequenced entirely upon identification of the correct mutation. Automated DNA sequencing was performed using a Beckman Coulter CEQ™ 8000 genetic analysis system (Beckman Coulter, Fullerton, Calif.) and analyzed using Beckman Coulter CEQ™ 8000 (Beckman Coulter) and Lasergene® software (DNASTAR, Madison, Wis.). Vaccine DNA for immunization was prepared using Qiagen endo-free maxi-prep kits.

Mice—Protective Efficacy

Six-week old type I/type II IFN receptor-knock-out mice (AG129) were used. AG129 mice (DVBD, n=26) were immunized with 100 μg of pVD1-WT or pVD1-CRR vaccine (50 μg in each thigh i.m.) at 0, 4, and 8 weeks. Immunized and naïve age-matched mice (n=8) were challenged at 12 weeks intraperitoneally (i.p.) with $1.1 \times 10^5$ FFU of DENV-1 Mochizuki strain. Based upon results from previous dose-titration experiments, four animals from each vaccine treatment and two naïve mice were a priori selected for sacrifice 3 and 8 days post challenge (DPC). Sick animals reaching predetermined morbidity endpoints were anesthetized, total blood was collected via cardiac puncture, euthanized and carcasses were frozen at −80° C. for subsequent analysis of brains.

Mice—Vaccine Safety

AG129 mice (DVBD, n=26) were immunized with 100 μg of either pVD1-WT or pVD1-CRR vaccine (50 μg in each thigh, i.m.) at 0 weeks. Immunized and age-matched naïve mice (n=10) were challenged at 12 weeks (i.p.) with $4.2 \times 10^5$ FFU of DENV-2 S221 (Zellweger et al., *Cell Host Microbe* 7(2):128-139, 2010). Four mice from each vaccine treatment and two naïve mice were a priori selected for sacrifice 3 DPC. Sick animals reaching pre-determined morbidity endpoints were anesthetized, total blood was collected via cardiac puncture, euthanized, and necropsy was performed with livers collected and stored in 10% formalin for histology.

Histology

Liver tissue sections were prepared, stained, and analyzed. IHC utilized Ventana Medical Systems ultraView Universal Alkaline Phosphatase Red Detection Kit following the manufacturer's recommended protocols and a Benchmark Ultra automated system. Pretreatment was with protease II for 6 minutes, rabbit anti DENV-2 NS1 serum was used at a 1:20 dilution, and anti-rabbit secondary antibody was applied for 12 minutes.

Characterization of pVD1-Cross-Reactivity Reduced (CRR) Plasmid Vaccine Induced Virus-Like Particle (VLP) Antigen Antigen-capture ELISA (Ag-ELISA) was used to characterize VLP antigen following previously described protocols (Crill et al., *PLoS ONE* 4:e4991, 2009). Briefly, VLP antigen was collected from mutagenized and WT pVD1 transformed COS-1 cells. Secreted antigen was captured in the inner 60 wells of Immulon II HB flat-bottom 96-well plates (Dynatech Industries, Inc., Chantilly, Va.) with polyclonal rabbit anti-DENV-1 WT VLP sera, incubated overnight at 4° C., and wells were blocked with 300 μl of StartBlock blocking buffer (Pierce, Rockford, Ill.) according to the manufacturer's recommended protocol. Antigen was diluted 2-fold in PBS, incubated for 2 hours at 37° C. and detected with murine hyper-immune ascitic fluid (MHIAF) specific for DENV-2 diluted in 5% milk/PBS. MHIAF was detected using horseradish peroxidase conjugated goat anti-mouse IgG (Jackson ImmunoResearch, Westgrove, Pa.) in 5% milk/PBS and incubated for 1 hour at 37° C. Bound conjugate was detected with 3,3'5,5'-tetramethylbenzidine substrate (TMB; Neogen Corp., Lexington, Ky.), the reaction was stopped with 2N $H_2SO_4$ and measured at A450 using a Synergy HT Multi-Detection Microplate Reader (Bio-Tek Instruments, Inc., Winooski, Va.). WT and mutant antigens were screened against the MAb panel using the same ELISA protocol as above with the exception that 2-fold dilutions of the specific MAb replaced the anti-DENV-2 MHIAF and antigens were used at a single standardized concentration producing an optical density (OD) of 1.0. Standardized concentrations of WT and mutant VLP antigens were analyzed in Ag-ELISA to determine MAb end point reactivities.

Monoclonal Antibodies

MAbs 4G2, 6B6C-1, 4A1B-9, 1B7, D3-5C9-1, 1A1D-9, 9D12, 9A3D-8, 3H5, and D2-1F1-3 were obtained from hybridomas in the collection of the Arbovirus Diseases Branch, DVBD, CDC. Many of these MAbs originated from the work of John Roehrig (Roehrig et al., *Virology* 246:317-328, 1998), 4G2, 5H3, 1B7, D3-5C9-1, 9D12, 3H5, and D2-1F1-3 hybridomas were originally obtained by the CDC from the Walter Reed Army Institute (Henchal et al., *Am J Trop Med Hyg* 34:162-169, 1985). MAbs 23-1, 23-2, and 5-2 were provided by Dr. L.-K. Chen of Tzu Chi University, Hualien, Taiwan. MAbs 10-D35A, 20-783-745014, and MDVP-55A are commercially available and were purchased from Fitzgerald Industries International, GenWay Biotech Inc., and Immunology Consultants Laboratory Inc., respectively.

Epitope-Specific IgG ELISA (ES-ELISA)

We used DENV-1 and DENV-2 ES-ELISA to determine total DENV-1 or DENV-2 IgG end-point titers and to determine DENV-1 or DENV-2 $EDII_{FP}$, $EDIII_{CR}$, $EDII_{FP}EDIII_{CR}$, and non-$EDII_{FP}EDIII_{CR}$ epitope-specific IgG percentages. The DENV-2 ES-ELISA has been previously described (Crill et al., *PLoS ONE* 4:e4991, 2009) and the DENV-1 ES-ELISA was similarly used with a few modifications. Briefly, rabbit anti pVD1 or pVD2 sera was coated onto plates overnight at 4° C. Standardized concentrations of WT and CRR antigens were captured, AG129 mouse serum was diluted four-fold down the plate, and detected with goat anti-mouse IgG (Jackson ImmunoResearch). Vaccinated mouse sera were diluted 1:100-1:400 and serially titrated. The DENV-1 epitope-specific knock-out antigens utilized are described in Table 2. OD values were modeled as non-linear functions of the login sera dilutions using a non-linear sigmoidal dose-response (variable slope) regression in Graph Pad Prism version 4.0 and endpoint titrations were determined as the titer where the OD value equaled two-times the OD value of the test serum reacted against normal COS-1 antigen.

$EDII_{FP}$, $EDIII_{CR}$, $EDII_{FP}EDIII_{CR}$, and non-$EDII_{FP}EDIII_{CR}$ epitope-specific IgG percentages were calculated as previously described (Crill et al., *PLoS ONE* 4:e4991, 2009) with minor modifications. The DENV-1 epitope-specific IgG percentages for all vaccinated mice were calculated by dividing the IgG endpoint titer obtained with each knock-out antigen ($EDII_{FP}$, $EDIII_{CR}$, or $EDII_{FP}EDIII_{CR}$) by the endpoint titer obtained with pVD1-WT antigen on the same sera, subtracting this value from 1.0, and multiplying by 100. Specifically, $EDII_{FP}$ epitope-specific percentages were calculated as 100×[1.0−(DENV-1 $EDII_{FP}$ antigen endpoint/DENV-1 WT antigen endpoint)]. $EDIII_{CR}$ epitope-specific percentages were calculated as 100×[1.0−(DENV-1 $EDIII_{CR}$ antigen endpoint/DENV-1 WT antigen endpoint)]. $EDII_{FP}EDIII_{CR}$ IgG was calculated as 100×[1.0−(DENV-1 $EDII_{FP}EDIII_{CR}$ antigen endpoint/DENV-1 WT antigen endpoint)].

Non-$EDII_{FP}EDIII_{CR}$ IgG proportions were calculated as 100*(endpoint $EDII_{FP}EDIII_{CR}$/endpoint WT) for WT vaccinated mice and because pVD1-CRR vaccinated mouse sera contain antibodies that do not recognize some WT antigen epitopes (WT antigen acts as the knock-out antigen) but recognize the modified epitopes of the CRR antigens, the pVD1-CRR antigen ($EDII_{FP}EDIII_{CR}$) replaced pVD1-WT antigen to determine 100% E reactivity for pVD1-CRR vaccinated mice and similarly, the non-$EDII_{FP}EDIII_{CR}$ IgG proportion for pVD1-CRR immunized mice was calculated as 100*(DENV-1 WT antigen endpoint/DENV-1 $EDII_{FP}EDIII_{CR}$ antigen endpoint). DENV-2 epitope specific IgG populations were similarly determined but used the previously described DENV-2 $EDII_{FP}$, $EDIII_{CR}$, and $EDII_{FP}EDIII_{CR}$ knock out antigens to determine endpoints (Crill et al., *PLoS ONE* 4:e4991, 2009) for both pVD1-WT and pVD1-CRR vaccinated sera. In cases where the endpoint titer determined with a mutant antigen was the same or greater than the endpoint titer obtained with the cognate antigen, it was interpreted as undetectable levels of antibody recognizing the epitope of interest and the percent of IgG was arbitrarily set at 0.05%.

Epitope-Blocking ELISA

Epitope blocking ELISA was utilized to determine the vaccinated mouse response to well-characterized murine MAb epitopes. This ELISA was set up similar to ES-ELISA in that plates were coated overnight at 4° C. with rabbit anti-DENV-2 serum, blocked with StartBlock (Pierce), dried and WT DENV-2 VLP antigen was captured 1 hour at 37° C. After washing, pVD1-WT or pVD1-CRR vaccinated, DENV-2 challenged mouse serum (3 DPC, pooled for each vaccine treatment) was diluted 1:40 in wash buffer and incubated 1 hour at 37° C. Following pooled serum incubation and wash, 0.5 μg of horseradish peroxidase (HRP)-conjugated MAb was added to each well and incubated for 1 hour at 37° C. to compete with the already bound antibody from vaccinated mouse serum for WT DENV-2 VLP antigen. Bound conjugate was detected with TMB substrate and plates incubated for 10 minutes prior to being stopped with $H_2SO_4$ and ODs were determined as OD=OD of $A_{450}$-OD of $A_{630}$. Percent blocking was determined by comparison to replicate wells with 0.5 μg HRP labeled MAb competing against pre-adsorbed normal mouse serum. Percent blocking was determined using the following calculation, 100−100*[(OD of vaccinated serum on DENV-2 Ag-OD of vaccinated serum on normal Ag)/OD of normal serum on DENV-2 Ag-OD of normal serum on normal Ag)].

Antibody-Dependent Enhancement

Heat inactivated pVD1-WT and pVD1-CRR vaccinated mouse sera (12 weeks post vaccination) were pooled into 4 groups for each vaccine treatment, diluted, and titrated. Virus (DENV-2 16681) was added to each dilution and incubated for 1 hour at 37° C. K562 cells (MOI=0.5) were added to the antibody-virus complexes and incubated 2 hours. After infection, cells were centrifuged, supernatants removed, resuspended in RPMI media (10% FBS) and plated. DENV infection alone was used as virus control.

Focus Reduction Micro-Neutralization Assay (FRμNT)

FRμNT assay was utilized as previously described (Crill et al., *PLoS ONE* 4:e4991, 2009) with few modifications. Vaccinated mouse sera were diluted 1:10, heat inactivated, titrated 2-fold to the volume of 40 μL, and 320 virus focus-forming units (FFU)/40 μL (DENV-1 56BC94/95, DENV-2 16681, DENV-3 116RC1396, or DENV-4 130) was added to each dilution. FRμNT titers were calculated for each virus relative to a back titration. Exact 50% of FRμNT titers were modeled using Graph Pad Prism version 4 sigmoidal dose response (variable slope) non-linear regression. Values are the average of two independent replicates.

Viremia and Brain Virus Titers

Viremia was determined in a similar antigen-focus assay as described for FRμNT except that no virus was added. Cells were incubated, overlaid, acetone fixed, immunostained and counted as described for FRμNT. Virus brain titers were determined from previously frozen mouse carcasses. Brain tissue was aspirated with a 3 mL syringe and 18 gauge needle, weighed, and resuspended in 200 μL BA-1 media. 50 μL was used in the FRμNT as described. FFU/g of tissue was back calculated from the aspirated brain mass.

Cytokine Assays

Serum samples from terminally ill mice were frozen at −70° C., thawed on ice, and virus was heat inactivated. Serum samples were used in detection of cytokines in a mouse inflammatory cytometric bead array (BD Biosciences, San Jose, Calif.) as per manufactures protocol. Fluorescence was detected on BD FACSCalibur and analyzed with FCAP array software (BD Biosciences, San Jose, Calif.).

Example 2: Redirecting the Immune Response to DENV Vaccination

This example describes the development and characterization of a cross-reactivity reduced (CRR) DENV-1 DNA vaccine.

Vaccine Construction

Figure 1B:
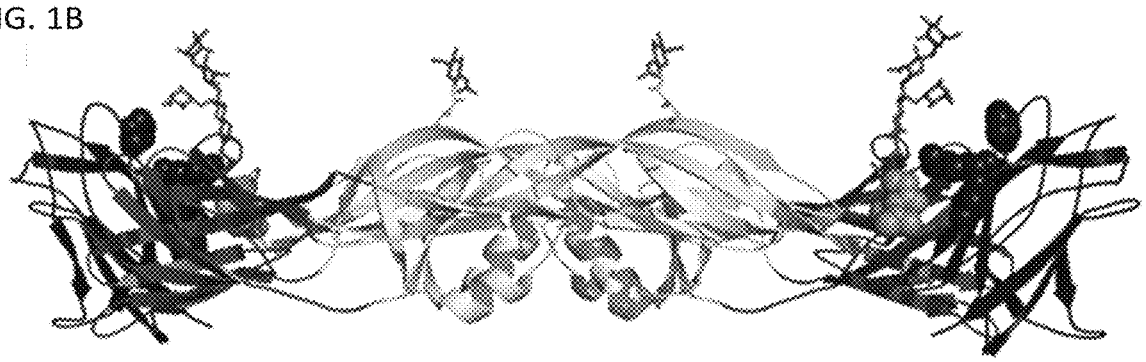
Figure 1C:
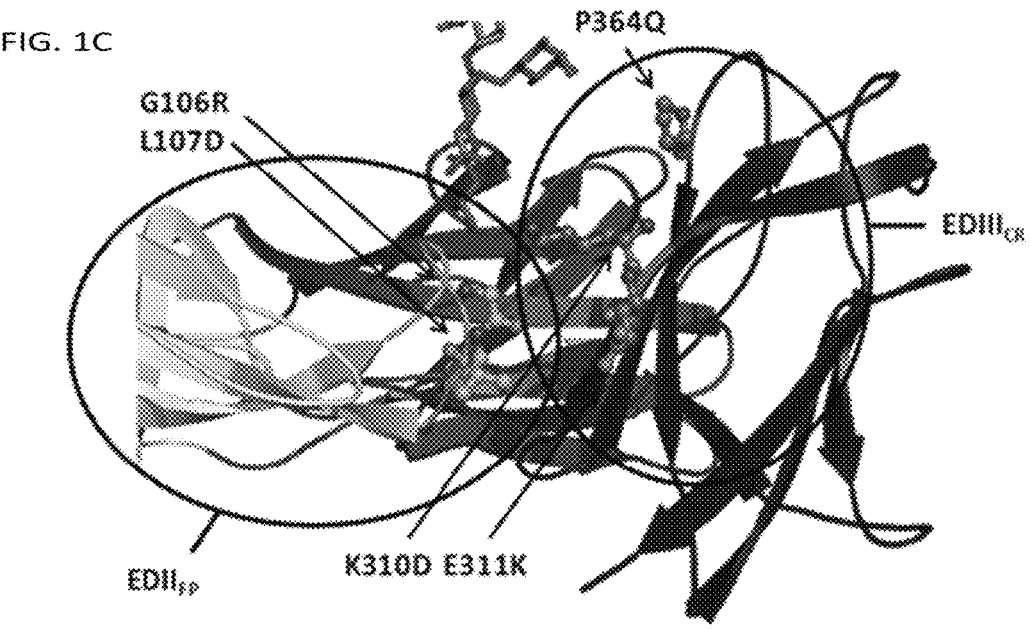

Based upon previously published and unpublished results with dengue viruses (DENV) and other flaviviruses (Crill et al., *PLoS ONE* 4:e4991, 2009), specific substitutions were introduced into the envelope protein of a DENV-1 premembrane/envelope protein (prM/E) expression vector plasmid (Chang et al., *Virology* 306:170-180, 2003) and a DENV-1 DNA vaccine candidate with reduced ability to induce the cross-reactive antibodies associated with antibody-dependent enhancement (ADE) was generated. The DENV-1 wild-type DNA vaccine (pVD1-WT) utilized as the template for the cross-reactivity reduced vaccine (pVD1-CRR) in this study was based upon extensive studies with DENV-2 vaccines (Chang et al., *Virology* 306:170-180, 2003). Substitutions were introduced into two important antigenic regions of the DENV E protein, the highly conserved fusion peptide of structural domain II ($EDII_{FP}$) and the receptor-binding immunoglobulin-like domain III (EDIII; FIG. 1).

$EDII_{FP}$ contains multiple overlapping immunodominant B cell epitopes inducing broadly cross-reactive, weakly or non-neutralizing antibodies associated with antibody enhanced severe DENV disease in both mice and humans (Lai et al., *J Virol.* 82(13):6631-6643, 2008; Crill et al., *PLoS ONE* 4:e4991, 2009; Zellweger et al., *Cell Host Microbe* 7(2):128-139, 2010; Balsitis et al., *PLoS Pathog* 6:e1000790, 2010; Beltramello et al., *Cell Host Microbe* 8:271-283, 2010; Crill and Chang, *J Virol* 78:13975-13986, 2004; Stiasny et al., *J Virol* 80:9557-9568, 2006). EDIII contains two well-characterized overlapping antigenic regions, one stimulating DENV complex cross-reactive antibodies varying in their neutralizing capabilities (Roehrig et al., *Virology* 246:317-328, 1998; Sukupolvi-Petty et al., *J Virol* 81:12816-12826, 2007; Gromowski et al., *J Virol* 82:8828-8837, 2008) and the other stimulating DENV serotype-specific, potently neutralizing antibodies associated with DENV serotype-specific immunity (Crill et al., *PLoS ONE* 4:e4991, 2009; Beltramello et al., *Cell Host Microbe* 8:271-283, 2010; Sukupolvi-Petty et al., *J Virol* 81:12816-12826, 2007; Gromowski and Barrett, *Virology* 366:349-360, 2007).

Multiple substitutions at $EDII_{FP}$ residues G106 and L107, and at K310, E311, and P364 in the cross-reactive antigenic region of EDIII ($EDIII_{CR}$; FIG. 1), were examined. Final individual substitutions at these five residues were selected based upon their influence on in vitro virus-like particle (VLP) secretion and their effect on the reactivities of a panel of well-characterized monoclonal antibodies (MAbs, Table 2). $EDII_{FP}$ substitutions tended to increase VLP secretion and knocked out the reactivity of flavivirus group and sub-group cross-reactive MAbs. $EDIII_{CR}$ substitutions were specifically selected not to interfere with the binding of potently neutralizing EDIII serotype-specific MAbs. These substitutions tended to reduce VLP secretion relative to WT and ablated the reactivity predominately of DENV sub-complex cross-reactive MAbs. The final pVD1-CRR plasmid, containing substitutions at all five of the sites across both $EDII_{FP}$ and $EDIII_{CR}$ antigenic regions (FIG. 1), knocked-out or reduced the reactivity to below detectable levels of 11 cross-reactive monoclonal antibodies in the panel (Table 2). The cross-reactive MAbs whose reactivities were not significantly reduced were 1B7, a sub-group cross-reactive MAb that neutralizes all 4 DENV serotypes (Table 3), and 10-D35A and D3-5C9-1, weakly (for DENV-2) and non-neutralizing DENV complex cross-reactive MAbs respectively.

pVD1-WT and pVD1-CRR Vaccines Both Induce High Titer Total Immunoglobulin and Neutralizing Antibody, Protecting Mice from Lethal DENV-1 Challenge To test for vaccine protective efficacy, WT and CRR DENV-1 DNA vaccines were compared by immunizing AG129 mice and subsequently challenging with a lethal dose of homologous DENV-1 (Mochizuki strain). AG129 Type I/Type II IFN receptor knock-out mice have impaired neutralizing antibody responses (Schijns et al., *J Immunol* 153:2029-2037, 1994) and as expected our DNA vaccines were not as immunogenic in these mice as in immunocompetent mouse strains. Therefore, the standard immunization schedule was altered from a single 100 µg boost 4 weeks following primary vaccination (100 µg) to two 100 µg boosts at 4 and 8 weeks. This schedule produced immune responses approaching the magnitude of those previously observed in other mouse strains with the two dose schedule (Chang et al., *Virology* 306:170-180, 2003). Mice were challenged at 12 weeks. Prior to challenge, mouse sera was collected and vaccine-induced immune responses were measured.

Figure 2C:
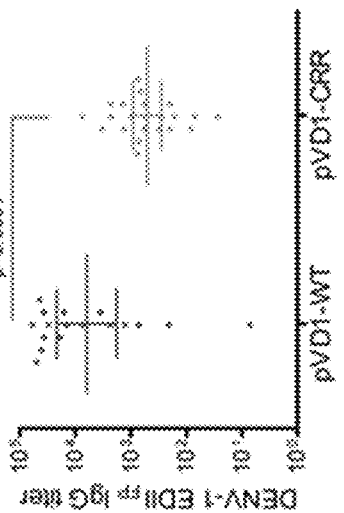
FIGS. 2A-2F: Protective Efficacy—Both pVD1-WT and pVD1-CRR vaccines protect AG129 mice against lethal DENV-1 challenge.
Figure 2B:
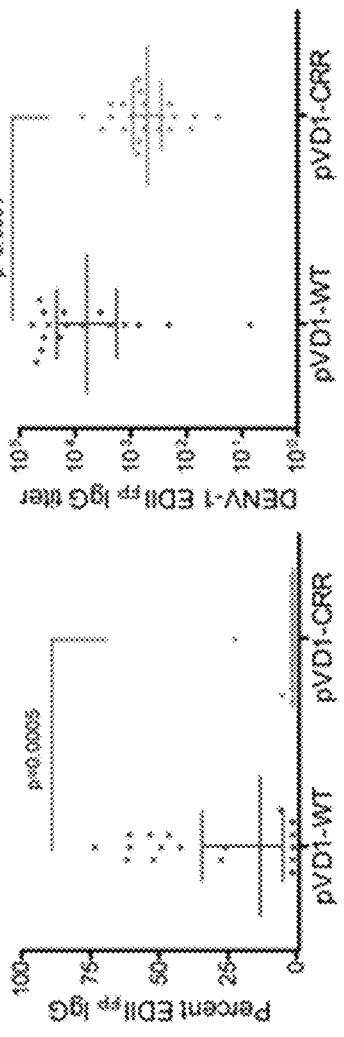
Figure 2A:
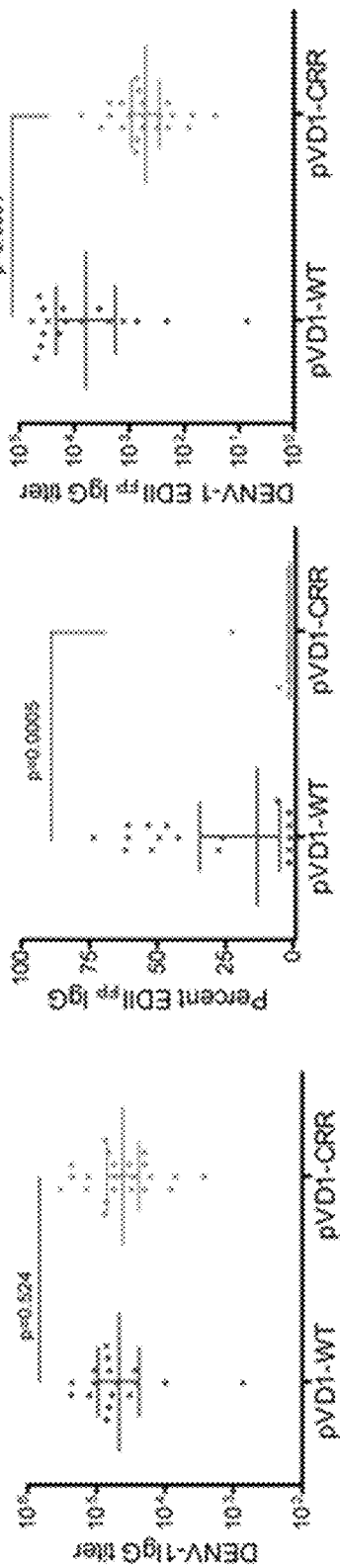
Figure 2F:
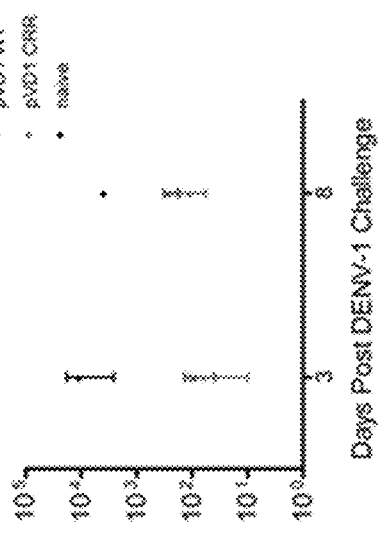
Figure 2E:
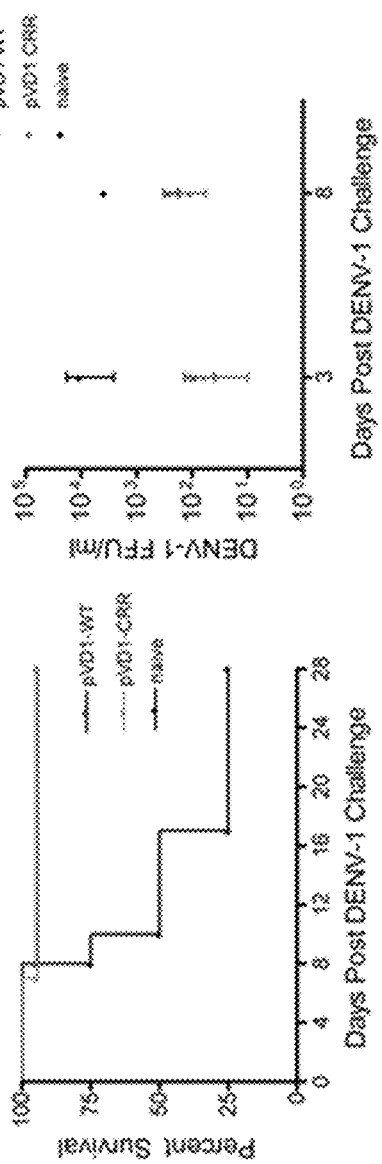
Figure 2D:
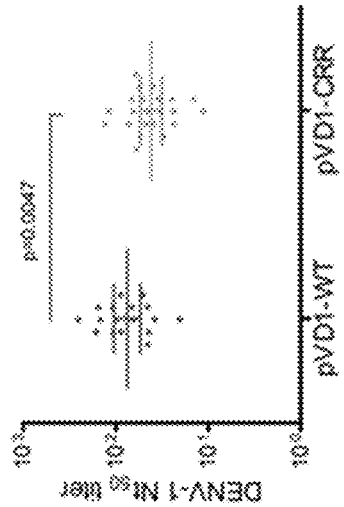

ES-ELISA (Crill et al., *PLoS ONE* 4:e4991, 2009) was used to determine total DENV-1 IgG and DENV-1 $EDII_{FP}$ IgG. Total DENV-1 IgG end-point titers were similar between the two vaccines and averaged $7.7 \times 10^4 \pm 1.5 \times 10^4$ and $7.5 \times 10^4 \pm 1.8 \times 10^4$ for pVD1-WT and pVD1-CRR immunized mice respectively (p=0.524; FIG. 2A). However, pVD1-CRR immunized mice had significantly lower proportions of $EDII_{FP}$ IgG than did pVD1-WT immunized mice, averaging 2.1±0.96% and 33±6.4% of the total IgG response respectively (p=0.0005, FIG. 2B). Only two pVD1-CRR immunized mice had measurable $EDII_{FP}$ IgG (4.8% and 22%) with the remaining mice being below detectable levels (conservatively set to 1.0% for statistical analyses and $EDII_{FP}$ IgG titer calculations). The proportion of $EDII_{FP}$ IgG for WT immunized mice was large and variable, ranging from 0.8% to 73%, similar to that observed in DENV infected humans (Stiasny et al., 2006; Crill et al., 2009; Beltramello et al., 2010). Calculated $EDII_{FP}$ IgG end-point titers averaged $2.0 \times 10^4 \pm 4.6 \times 10^3$ and $1.1 \times 10^3 \pm 3.4 \times 10^2$ for WT and CRR immunized mice respectively (p=0.0001, FIG. 2C). 50% neutralization ($Nt_{50}$) titers, measured by FRµNT, averaged 91.1 and 48.8 for pVD1-WT and pVD1-CRR vaccinated mice respectively (p=0.0047; FIG. 2D). The lower $Nt_{50}$ titer for pVD1-CRR immunized mice was likely due to reduced induction of $EDIII_{CR}$ antibodies recognizing epitopes similar to those of neutralizing MAbs 1A1D-2 and 9D12 that lost all measurable reactivity for the pVD1-CRR tissue culture derived VLPs (Table 1). These results indicate that targeted substitution within $EDII_{FP}$ reduces the immunodominance of this region.

Age-matched naïve (18 week old, n=8), pVD1-WT and pVD1-CRR (n=26 each) vaccinated animals were challenged with $1.1 \times 10^5$ focus forming units (FFU) of the mouse-brain adapted DENV-1 Mochizuki strain. This dose was greater than 100 $LD_{50}$ for 6-8 week old mice. All immunized mice except a single animal from each vaccine treatment were protected and survived challenge (94% survival) which was highly significant in comparison to naïve mice (25% survival, p=0.0003; FIG. 2E). Time to death of naïve mice ranged from 8-17 days post challenge (DPC) and averaged 11.7 DPC; the single vaccinated animals died 7 and 8 DPC for WT and CRR vaccine treatments respectively. Surviving mice showed no signs of sickness. Although DENV-1 Mochizuki is a mouse-brain adapted virus, limited neurological symptoms such as paralysis in terminally sick mice was observed, and most exhibited hunched and ruffled posture, lethargy, and a lack of interest in food and water leading to weight loss prior to being euthanized. Four mice from each vaccine treatment and two naïve mice were scheduled a priori to be euthanized at 3 DPC, a time point prior to any outward sign of disease, and 8 DPC, a few days after the initial signs of morbidity and mortality. Vaccinated mice exhibited 100-fold and 10-fold lower viremia 3 and 8 DPC respectively, compared to naïve controls; yet there was no difference in mean viremic titers between WT or CRR vaccinated mice at either time point (FIG. 2F). A two-way ANOVA found vaccine treatment to be highly significant ($P<0.0001$) and to account for 68% of the variation. Bonferroni posttests indicated that viremia of each vaccinated group was significantly lower than for naïve mice 3 DPC ($p<0.001$) whereas only pVD1-CRR immunized mouse viremia was significantly lower than naïve mice 8 DPC ($p<0.01$).

Because DENV-1 Mochizuki strain is a mouse-brain adapted virus, virus titers of mouse brain homogenates were also determined. Brains from both naïve and vaccinated mice were all negative 3 DPC (<50 FFU/g brain tissue). By 8 DPC, virus titers of naïve mouse brain tissue was 100-1000 times greater than for vaccinated mice, however limited sampling and high variance precluded rigorous statistical conclusions. The single 8 DPC naïve mouse brain virus titer was $2.3\times10^4$ FFU/g, median virus titers of WT and CRR vaccinated mice (n=4 each) were 50 and 325 FFU/g of brain tissue respectively with three of four WT and two of four CRR vaccinated brain tissue titers below the limits of assay detection (<50 FFU/g tissue). A one sample t-test of all 8 vaccinated mouse brain titers compared to the single $2.3\times10^4$ titer for the naïve mouse strongly rejected the null hypothesis ($p=0.0042$), suggesting that there was less virulence in vaccinated compared to naïve mouse brains.

Consistent with an anamnestic response to DENV-1 challenge, both WT and CRR immunized surviving mice exhibited similar order of magnitude increases in $Nt_{50}$ titer 28 DPC (GMT=690, 95% CI 504-944 and =362, 95% CI 218-601 for WT and CRR respectively). Together, these data suggest that pVD1-WT and pVD1-CRR vaccines are similarly immunogenic and able to induce protective immunity against lethal homologous DENV-1 challenge in the AG129 DENV vaccine model.

Cross-Reactivity Reduced Vaccine Redirects Immunity from Immunodominant Pathological Responses Toward Protective Responses to Improve Vaccine Safety and Efficacy To test for the possibility of an improved safety profile of the CRR DENV-1 DNA vaccine, AG129 mice were immunized with 100 μg WT or CRR vaccine, and after waiting 84 days for potential transient cross-protection to dissipate, mice were challenged with a sub-lethal dose of DENV-2. This scenario mimics the vaccine safety concern of enhanced disease that could occur following DENV exposure with incomplete tetravalent vaccine seroconversion, e.g., prior to final boosting with some prolonged vaccine schedules (Sun et al., *Hum Vaccin* 5:33-40, 2009; Morrison et al., *J Infect Dis* 201:370-377, 2010). Immunized mice were challenged with DENV-2 S221, a mouse adapted isolate of Taiwanese strain PL046 (Shresta et al., *J Virol* 80:10208-10217, 2006). This virus is capable of producing lethal hemorrhagic disease in AG129 mice, similar to that observed in human DHF, via ADE when sub-protective levels of DENV immune sera are passively transferred to mice and subsequently challenged with non-lethal doses of DENV-2 S221 (Zellweger et al., *Cell Host Microbe* 7(2): 128-139, 2010; Balsitis et al., *PLoS Pathog* 6:e1000790, 2010). Based on previous work with CRR DENV-2 DNA vaccines, it was hypothesized that pVD1-WT mice would be susceptible to antibody-enhanced DENV disease due to high levels of vaccine-induced cross-reactive antibodies and that upon subsequent heterologous challenge, antibodies recognizing these immunodominant epitopes would be stimulated anamnestically. Conversely, pVD1-CRR vaccinated mice would lack such immunodominant cross-reactive antibody priming and secondary responses, be less susceptible to antibody enhanced viral replication, and have increased immunological capability to rapidly respond with appropriate DENV-2 immunity. pVD1-CRR vaccinated mice should therefore be less susceptible to antibody enhanced DENV-2 disease.

Figures 3A, 3B, 3C, 3D, 3E, 3F:
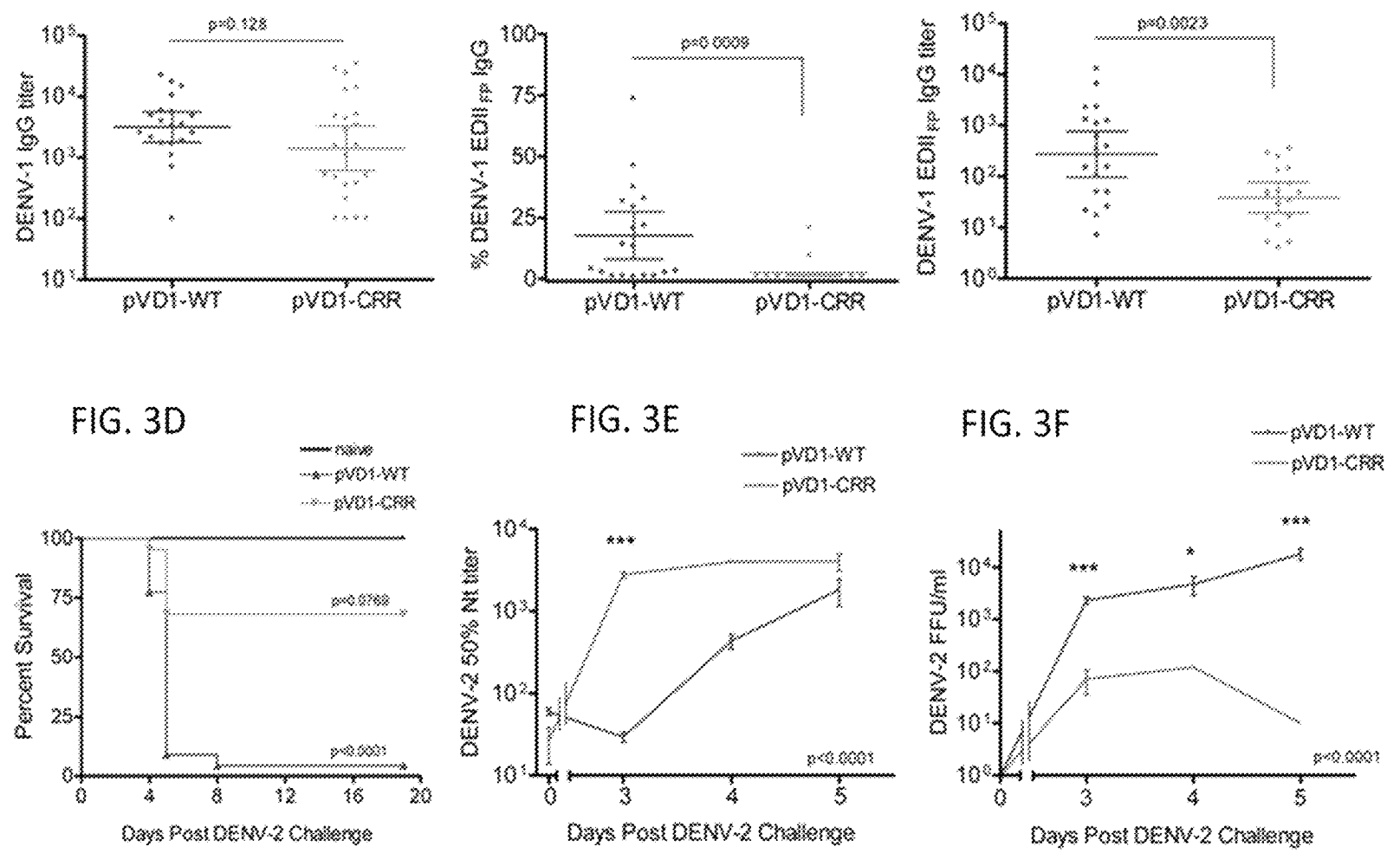

DENV-1 CRR Vaccinated Mice have Reduced Levels of Immunodominant $EDII_{FP}$ IgG and Reduced Dengue Disease Mortality Compared to DENV-1 WT Vaccinated Mice Following DENV-2 Challenge To assess if pVD1-WT and -CRR vaccines induce different antibody repertoires in vaccinated mice, 12 week post-vaccination sera was collected and utilized in ES-ELISA (Crill et al., *PLoS ONE* 4:e4991, 2009) to determine vaccine induced DENV-1 IgG titers and the proportions and titers of IgG recognizing $EDII_{FP}$ epitopes (FIG. 1). There was no difference in total DENV-1 IgG GMT between pVD1-WT (3168, 95% CI 1792-5600; n=20) and pVD1-CRR immunized mice (1429, 95% CI 621-3289, n=23; p=0.128, two-tailed Mann-Whitney U test; FIG. 3A). The percent of total DENV-1 IgG recognizing $EDII_{FP}$ epitopes averaged 17.7±4.6% and 2.56±1.2% for pVD1-WT and pVD1-CRR immunized mice respectively (p=0.0009). Again, only two CRR immunized mice had detectable levels of $EDII_{FP}$ IgG (9.4% and 21%) with all remaining mice having no measurable $EDII_{FP}$ IgG (=1.0% for statistical analyses; FIG. 3B). The calculated DENV-1 IgG GMT recognizing $EDII_{FP}$ epitopes was significantly lower for CRR (38.6, 95% CI 19.4-76.9) than for WT immunized mice (272, 95% CI 97.2-760, p=0.0023, one-tailed Mann-Whitney U test; FIG. 3C). These results again indicate that pVD1-WT and pVD1-CRR vaccines are similarly immunogenic overall, but that the pVD1-CRR vaccine induces less IgG recognizing immunodominant $EDII_{FP}$ epitopes.

Age-matched naïve (n=10), pVD1-WT, and pVD1-CRR (n=26 each) immunized mice were challenged (i.p.) with a sub-lethal dose ($4.2\times10^5$ FFU) of DENV-2 S221 12 weeks following immunization for vaccine treatment groups. All naïve mice survived DENV-2 challenge, though they did exhibit signs of morbidity including decreased activity, coat ruffling, and weight loss. pVD1-WT vaccinated mice suffered from severely enhanced DENV-2 pathology, including hemorrhagic manifestations producing 95% mortality ($p<0.0001$ compared to naïve). Conversely, pVD1-CRR vaccinated mice exhibited reduced DENV-2 disease enhancement and 68% survival which did not differ from naïve mouse survival (100%, p=0.0769) and yet was much greater than WT vaccinated mouse survival (4.5%, $p<0.0001$, the Bonferroni multiple comparison adjusted $\alpha=0.017$; FIG. 3D). Sick mice began exhibiting external signs of morbidity late on day 3 and reached terminal endpoints 4.5-5.5 DPC for both groups with one WT vaccinated mouse surviving to 8 DPC.

To characterize which humoral immune determinates might be responsible for the reduced disease severity and mortality of CRR vaccinated mice, sera from 3, 4, and 5 DPC was examined. Four animals in each vaccine treatment were selected a priori for sacrifice 3 DPC, a time point when mice exhibited no outward signs of morbidity. Four and 5 DPC sera were obtained from terminally sick mice via cardiac puncture just prior to euthanasia. Thus, sample sizes were limited on some of these days for pVD1-CRR vaccinated mice since there was limited mortality relative to pVD1-WT vaccinated mice. Serum specimens were collected and DENV-2 $Nt_{50}$, viremia, and ES-ELISA titers were determined. DENV-2 neutralization was strongly correlated with survival; pVD1-CRR immunized mice exhibited a rapid, large magnitude rise in DENV-2 neutralization whereas in pVD1-WT immunized mice, neutralization was lower and increased more slowly ($p<0.0001$ in a 2-way ANOVA, FIG. 3E). 3 DPC $Nt_{50}$ titers of pVD1-CRR vaccinated mice were nearly 100 times greater than those of pVD1-WT vaccinated mice (CRR=2783.6, WT=29.5; Bonferroni posttest $p<0.001$). This was a greater than 100-fold increase in DENV-2 neutralization compared to pre-challenge for CRR vaccinated mice whereas it was a two-fold decrease over the same time period for WT vaccinated mice. $Nt_{50}$ titers of CRR vaccinated mice remained high 4 and 5 DPC whereas those of WT vaccinated mice slowly increased and remained 2-fold lower than CRR vaccinated mice by 5 DPC. Viremia was negatively correlated with DENV-2 neutralization and positively correlated with mortality (FIG. 3F). 3 DPC mean viremia of WT vaccinated mice was 33 times higher (2325 FFU/ml) than that of CRR vaccinated mice (70 FFU/ml; Bonferroni posttest $p<0.001$) with two of four CRR immunized mouse sera below the limits of assay detection (10 FFU/ml). WT viremia continued to increase 4-5 DPC and by 5 DPC was at least 1800 times higher than for CRR immunized mice where all individuals had dropped to below detectable levels (ave=$1.8\times10^4$ and $<10$ FFU/ml for WT and CRR immunized mice respectively; $p<0.001$ with Bonferroni posttest in 2-way ANOVA). These findings imply that even though some CRR vaccinated mice were terminally ill 5 DPC, they had cleared their viremia, whereas WT vaccinated mice still exhibited increasing viremia during this time of maximal mortality. Thus, the rapid, large magnitude increase in DENV-2 neutralization of pVD1-CRR vaccinated mice was consistent with an anamnestic response or potentially redirected immunity, whereas the slow rise in DENV-2 neutralization of WT vaccinated mice was more characteristic of a primary immune response.

pVD1-WT vaccinated AG129 mice suffering from lethally enhanced DENV-2 disease exhibited pathology consistent with ADE disease described in passive transfer studies with this mouse model (Balsitis et al., *PLoS Pathog* 6:e1000790, 2010; Zellweger et al., *Cell Host Microbe* 7:128-139, 2010). 3 DPC neither vaccinated nor naïve mice exhibited visible pathological symptoms upon necropsy. All terminally ill mice however had pale, blood-depleted livers, increased intestinal capillary blood flow, and enlarged gaseous stomachs, symptomatic of fluid accumulation caused by vascular leakage. Only WT vaccinated mice exhibited the most severe gastrointestinal hemorrhage (FIG. 4A). Although gross pathology upon necropsy of vaccinated mice was not observed until 4 DPC, hematoxylin and eosin staining of liver tissue revealed hepatitis pathology 3 DPC with increasing severity 4 and 5 DPC. Consistent with the reduced gross morbidity and mortality of pVD1-CRR compared to pVD1-WT vaccinated mice, CRR vaccinated mice reaching terminal endpoints exhibited mild lymphoplasmacytic portal, multifocal suppurative, and necrotizing hepatitis, including vacuolar vein congestion. However, pVD1-WT vaccinated mice exhibited moderate to severe lymphoplasmacytic, necrotizing, and multifocal portal hepatitis and in some individuals extensive vascular thrombosis and advanced vacuolar degeneration (FIG. 4B).

Severe DENV pathology via ADE posits that there should be increased infection of FcγR bearing monocytic cells in humans (Morens, *Clin Infect Dis* 19:500-512, 1994) and in AG129 mice, previous studies found that antibody-enhanced mortality was associated with increased DENV infection and replication in liver sinusoidal endothelial cells (Balsitis et al., *PLoS Pathog* 6:e1000790, 2010; Zellweger et al., *Cell Host Microbe* 7:128-139, 2010). Immunostaining for DENV-2 NS1 protein, which is expressed during viral replication, was used to assess viral replication in liver tissue. Of note, although no attempt was made to quantify differences between WT and CRR vaccine treatments, mononuclear inflammatory cells in the portal areas and sinusoidal endothelial cells of both WT- and CRR-vaccinated liver tissue were NS1 positive by 3 DPC, suggestive of active viral replication in FcγR bearing cells of the liver, and liver tissue of naïve mice was negative for NS1 by immunostaining (FIG. 4B). Lastly, pre-challenge pVD1-WT vaccinated mouse serum (1 day prior to DENV-2 challenge) significantly enhanced DENV-2 replication in FcγR bearing human K562 cells, and pVD1-CRR immunized mouse sera did not (FIG. 4C).

In summary, the high levels of DENV-1 vaccine induced cross-reactive $EDII_{FP}$ IgG prior to challenge, increased pathology and mortality, higher viremia, and active viral replication in FcγR bearing cells of WT immunized mice are all consistent with previous descriptions of antibody-enhanced DENV disease in AG129 mice (Balsitis et al., *PLoS Pathog* 6:e1000790, 2010; Zellweger et al., *Cell Host Microbe* 7:128-139, 2010).

Cross-Reactivity Reduced DNA Vaccination Sculpts Immune Memory so that Subsequent Response to Virus Infection is Redirected, Reducing Pathological and Increasing Protective Immunity DENV-1 and DENV-2 epitope-specific ELISA was utilized to quantify and differentiate humoral immune responses to DENV-1 vaccination from DENV-2 challenge. Supporting the hypothesis that WT vaccinated mice were slower to mount DENV-2 specific immunity due to DENV-1 primed cross-reactive memory responses, WT vaccinated mice had lower DENV-2 total IgG titers yet larger populations of both DENV-1 and DENV-2 $EDII_{FP}$ IgG than did CRR vaccinated mice following heterologous challenge (FIG. 5). Total DENV-1 IgG titers did not differ between vaccine treatments 3, 4, and 5 DPC with DENV-2 (FIG. 5A); however, DENV-2 IgG titers were higher for pVD1-CRR than for pVD1-WT immunized mice (FIG. 5B). Nevertheless, pVD1-WT vaccinated mice had significantly larger populations of $EDII_{FP}$ IgG for both DENV-1 (FIG. 5C) and DENV-2 (FIG. 5D) than did pVD1-CRR vaccinated mice. Not only did pVD1-WT mice have larger populations of cross-reactive $EDII_{FP}$ IgG following heterologous challenge, there was also a significant increase in DENV-1 $EDII_{FP}$ IgG post challenge when compared to the 12 week pre-challenge data (FIG. 5C). DENV-1 $EDII_{FP}$ IgG GMT of WT immunized mice increased from 17.7±4.6% pre-challenge to 35.5±5.4% of the total IgG response post DENV-2 challenge. However, there was no increase in DENV-1 $EDII_{FP}$ IgG for CRR immunized mice before and after challenge (p=0.364, Mann-Whitney U). Individual pairs of pre- and post-DENV-2 challenge sera from WT immunized mice were also analyzed for DENV-1 EDII$_{FP}$ IgG and this analysis also demonstrated a significant increase post-challenge (p=0.0138) and a significant effect of individual serum pairing (p=0.0267, one-tailed paired t-test). Together, these results demonstrate a strong memory response to cross-reactive E protein epitopes in DENV-2 that were primed by pVD1-WT vaccination and that such an immunodominant anamnestic response was lacking in pVD1-CRR immunized mice.

Figures 5A, 5B, 5C, 5D, 5E, 5F:
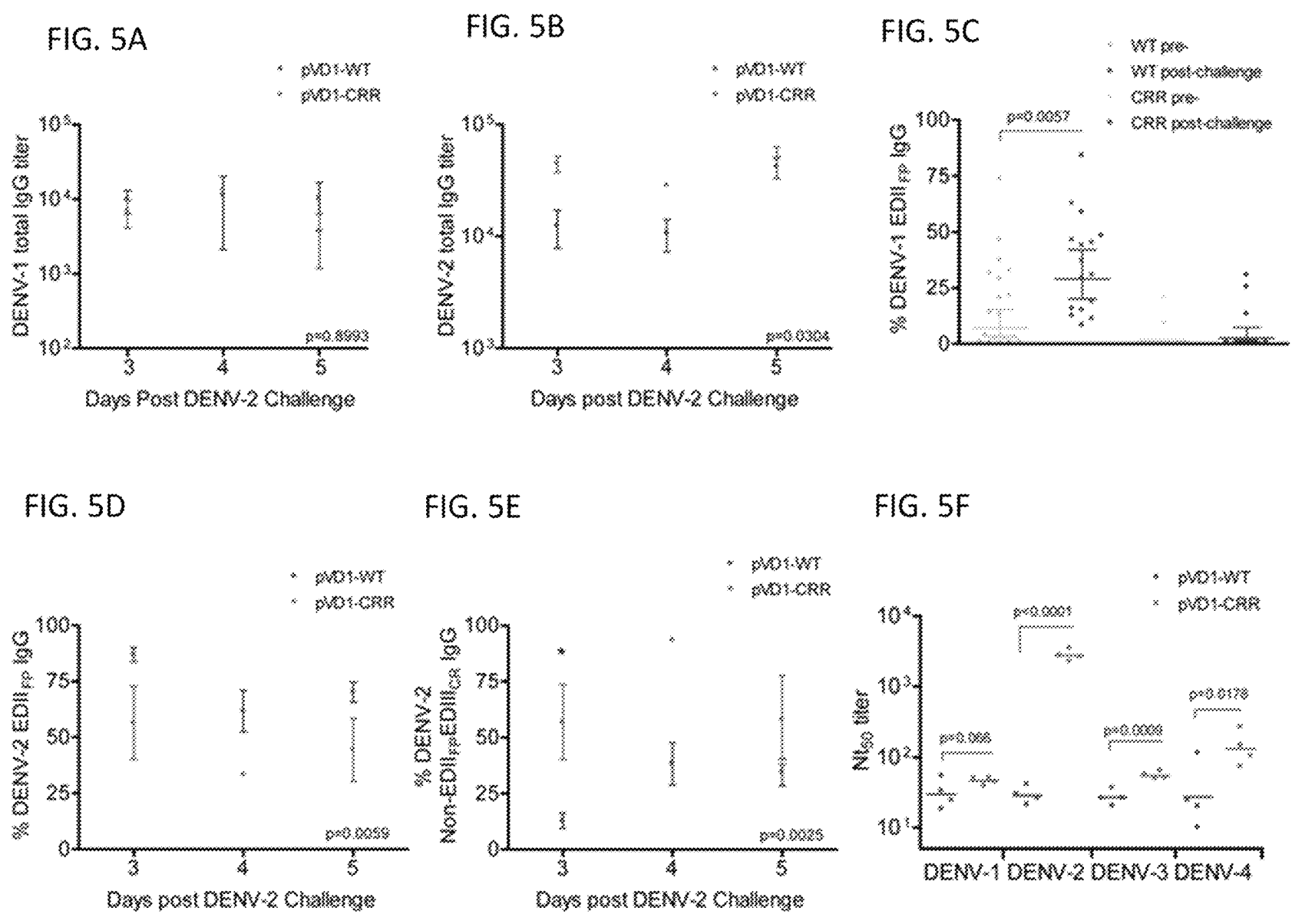

ES-ELISA can also determine the proportion of IgG recognizing E epitopes outside of the manipulated EDII$_{FP}$ and EDIII$_{CR}$ antigenic regions in the pVD1-CRR vaccine (non-EDII$_{FP}$EDIII$_{CR}$ IgG; FIG. 1)(Hughes et al., *Virol Journal* 9:115, 2012). It was hypothesized that pVD1-CRR immunized mice, with their reduced EDII$_{FP}$ response, would exhibit an increased capacity to redirect humoral immune responses to increase the DENV-2 non-EDII$_{FP}$E-DIII$_{CR}$ antibody populations concomitant with their reduced EDII$_{FP}$ response and that WT immunized mice would show the opposite pattern. Supporting this prediction, CRR vaccinated mice had significantly larger populations of DENV-2 non-EDII$_{FP}$EDIII$_{CR}$ IgG 3, 4, and 5 DPC with DENV-2 than did pVD1-WT immunized mice (p=0.0025 in 2-way ANOVA; FIG. 5E). This was the same time period that WT immunized mice exhibited maximum enhanced DENV-2 disease mortality (FIG. 3D) and significant increases in EDII$_{FP}$ IgG (FIGS. 5C and 5D); whereas CRR immunized mice exhibited 100-fold increased DENV-2 neutralization (FIG. 3E). Moreover, a comparison of DENV-1 non-EDII$_{FP}$ EDIII$_{CR}$ IgG for individual WT immunized mice pre- and post-challenge showed a significant decrease (p=0.0435) in this antibody population 3-5 DPC and a significant effect of individual mouse serum pairing on this decrease (p=0.0111, one-tailed paired t-test). A decrease in this DENV-1 antibody population of WT immunized mice is what one would expect if there is a trade-off between immunodominant secondary responses to EDII$_{FP}$ and non-EDII$_{FP}$EDIII$_{CR}$ epitopes. Antibody stimulated from epitopes outside EDII$_{FP}$ and EDIII$_{CR}$ antigenic regions altered in the pVD1-CRR vaccine include neutralizing DENV complex reactive antibodies such as MAb 1B7 primed by either vaccine and boosted by DENV-2 challenge (Table 2) and/or DENV-2 serotype-specific neutralizing antibodies stimulated only by the challenge virus.

Three non-mutually exclusive mechanisms could explain the rapid increase in DENV-2 neutralizing antibody by CRR immunized mice 3 DPC: 1) anamnestically increased complex cross-reactive neutralizing antibody not altered by the substitutions introduced in the pVD1-CRR vaccine (e.g., 1B7-like), 2) primarily increased DENV-2 specific neutralizing antibody, or 3) increased relative neutralizing capability of CRR vaccinated sera by these or other neutralizing antibody populations due to a lack of steric interference by the large populations of EDII$_{FP}$ IgG present in WT vaccinated mice (Ndifon et al., *Proc Natl Acad Sci USA* 106: 8701-8706, 2009). To test if the increased Nt$_{50}$ titers of CRR vaccinated mice were due to increases in DENV complex cross-reactive neutralizing antibodies, the Nt$_{50}$ titers for CRR and WT vaccinated mouse serum 3 DPC against DENV-1, DENV-3, and DENV-4 were determined (FIG. 5F). The mean (n=4 each) Nt$_{50}$ titers for CRR and WT vaccinated mice respectively were 46 and 33 for DENV-1 (p=0.066), 55 and 27 for DENV-3 (p=0.0009), and 147 and 42 for DENV-4 (p=0.0178; one-tailed t-test for all). These 1.5-, 2.0- and 3.5-fold higher DENV-1, -3, and -4 Nt$_{50}$ titers for CRR vaccinated mice did not approach the nearly 100-fold greater DENV-2 Nt$_{50}$ titer of CRR immunized mice 3 DPC (2785 and 29 respectively). These data indicate that CRR vaccinated mice have increased complex cross-reactive neutralizing antibody relative to WT vaccinated mice; but this antibody class either neutralizes DENV-2 more efficiently than other DENV serotypes, or there are also increased proportions of DENV-2 specific neutralizing antibody in CRR vaccinated serum by 3 DPC with DENV-2.

Figure 6:
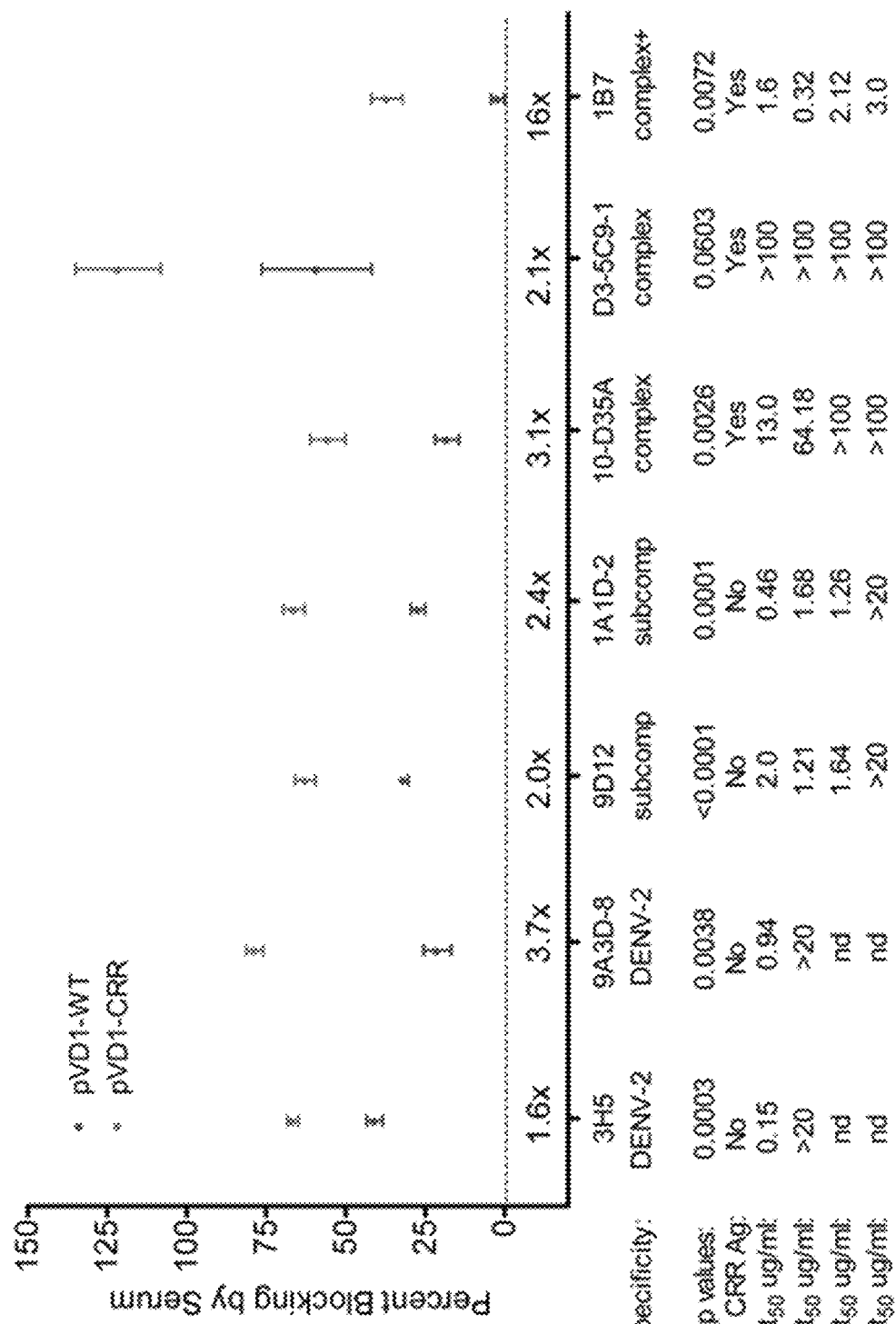
FIG. 6: DENV-1 CRR vaccination redirects immune responses to DENV-2 to increase a diversity of neutralizing antibodies. Percent blocking of labeled monoclonal antibodies (MAbs) by pVD1-WT and pVD1-CRR immunized mice 3 DPC to DENV-2 as determined by blocking ELISA. AG129 mice were immunized (i.m.) with 100 µg of pVD1-WT or pVD1-CRR vaccines and challenged at 12 weeks with a sub-lethal dose of heterologous DENV-2 S221 (4.2× 10$^5$ FFU, i.p.). Three DPC sera of the four mice from each vaccine treatment were pooled and percent blocking was determined independently four times in duplicate. To facilitate comparison between vaccine treatments across the different MAbs, x-fold increases in blocking by pVD1-CRR vaccinated sera relative to pVD1-WT vaccinated sera are depicted above the x axis for each MAb. Below the MAbs, serotype specificity is depicted (DENV-2=DENV-2 type specific, subcomp=DENV subcomplex cross-reactive, complex=DENV complex cross-reactive and complex+=supercomplex cross-reactive). Below specificity, p values from a two-tailed t-test comparing percent blocking for each vaccinated sera are depicted. Below that the presence or absence of the epitope recognized by each MAb on the DENV-1 CRR VLP antigen is depicted (all MAbs recognize epitopes found in the DENV-2 challenge virus). For example, 3H5 and 9A3D-8 as DENV-2 specific antibodies are absent on both pVD1-WT and pVD1-CRR VLP antigens; 9D12 and 1A1D-2 reactivity are ablated by the EDIII$_{CR}$ substitutions in the pVD1-CRR plasmid (Table 2) but present in the WT DENV-1 antigen; and 10-D35A, D3-5C9-1, and 1B7 reactivities were not altered by the substitutions introduced into the pVD1-CRR plasmid and hence are present on both DENV-1 WT and CRR immunization antigens. FRµNT$_{50}$ titers for each MAb against DENV-2, -1, -3, and -4 in µg/mL are also shown.

To further characterize the epitopes recognized by the antibodies responsible for the rapid rise in DENV-2 neutralization observed in CRR vaccinated mice, the ability of 3 DPC sera to block the binding of labeled MAbs was tested in a DENV-2 epitope-blocking ELISA. The blocking by WT and CRR vaccinated mouse sera for MAbs recognizing complex cross-reactive epitopes present in both DENV-1 vaccines and in the DENV-2 challenge virus (1B7, 10-D35A, and D3-5C9-1), MAbs recognizing sub-complex cross-reactive epitopes knocked out in the CRR vaccine but present in the WT vaccine and DENV-2 challenge virus (1A1D-2 and 9D12), and MAbs recognizing DENV-2 serotype-specific epitopes present only in the challenge virus (9A3D-8 and 3H5) was examined. pVD1-CRR vaccinated mouse sera exhibited significantly greater blocking than did WT vaccinated sera for all of these MAbs with the exception of D3-5C9-1 the only non-neutralizing MAb against DENV-2, indicating that CRR immunized mice had higher titers of antibody recognizing the same or similar epitopes as these labeled MAbs (FIG. 6). The greatest relative increase in blocking was for DENV complex, neutralizing MAb 1B7 which exhibited 16-fold greater blocking by CRR than the 2.25% blocking by WT (p=0.0072, two-tailed t-test), indicating greater 1B7-like neutralizing antibody in CRR vaccinated mouse sera than in WT mouse sera, and consistent with increased anamnestic induction of normally sub-dominant 1B7-like antibody in CRR immunized mice. CRR vaccinated mice also had 3.7 and 1.6-fold larger populations of DENV-2 serotype-specific potently neutralizing 3H5 and 9A3D-8 like antibodies than did WT vaccinated mice (p=0.0003 and p=0.0058 respectively), 2.4 and 2.0-fold greater sub-complex cross-reactive neutralizing 1A1D-2 and 9D12 like antibodies (p=0.0001 and p<0.0001 respectively), and 3.1-fold more DENV complex cross-reactive weakly neutralizing 10-D35A like antibodies (p=0.0026). There was a non-significant 2.1-fold increase in complex cross-reactive MAb D3-5C9-1.

Next, the neutralizing capabilities of these seven MAbs were determined since not all had been previously published in the literature (FIG. 6). DENV-2 serotype specific MAbs 3H5 and 9A3D-8 exhibited potent DENV-2 neutralization (NT$_{50}$=0.15 and 0.94 µg/mL respectively). 1A1D-2 also potently neutralized DENV-2 (0.46 µg/mL) although it neutralized DENV-1 and DENV-3 about 3-fold less than DENV-2, similar to the DENV-2 neutralizing capabilities of both 9D12 and 1B7. 10-D35A exhibited weak neutralization of DENV-2 (13.04 µg/mL), and D3-5C9-1 did not neutralize any DENV serotype. Together these results begin to tease apart the individual humoral immune components responsible for the polyclonal response of vaccinated mice to heterologous infection. The 100-fold increase in DENV-2 neutralization appeared to be due to a combination of large increases in cross-reactive neutralizing antibodies, similar to 1B7, but also to relative increases and large populations of potently neutralizing serotype-specific and sub-complex cross-reactive antibodies. Thus, in response to heterologous DENV-2 infection, pVD1-CRR immunized mice exhibited rapid increases in neutralizing antibody populations with diverse patterns of reactivity that not only increased protection from enhanced DENV-2 disease mortality but also exhibited increased neutralization breadth across the DENV complex.

To further define the epitopes recognized by the neutralizing antibodies responsible for the rapid rise in DENV-2 neutralization observed in CRR vaccinated mice, the ability of 3 DPC sera to block the binding of labeled MAbs was tested in a DENV-2 epitope-blocking ELISA. The blocking by WT and CRR vaccinated mouse sera was examined for MAbs recognizing complex cross-reactive epitopes present in both DENV-1 vaccines and in the DENV-2 challenge virus (1B7, 10-D35A, and D3-5C9-1), MAbs recognizing sub-complex cross-reactive epitopes knocked out in the CRR vaccine but present in the WT vaccine and DENV-2 challenge virus (1A1D-2 and 9D12), and MAbs recognizing DENV-2 serotype-specific epitopes present only in the challenge virus (9A3D-8 and 3H5). Three DPC pVD1-CRR vaccinated mouse sera exhibited significantly greater blocking than did WT vaccinated sera for all of these classes of MAbs, implying that CRR vaccinated sera had more antibody recognizing the same or similar epitopes as the labeled MAbs than did WT vaccinated sera (Table 3).

To standardize the percent blocking of these labeled MAbs by vaccinated mouse sera and facilitate comparison between antibodies, the fold difference in average MAb blocking by CRR vaccinated mouse sera compared to that of WT vaccinated mouse sera was determined for each MAb. The greatest increase in blocking by CRR sera compared to WT sera was for DENV complex, neutralizing MAb 1B7 which was 16-fold greater for CRR vaccinated than for WT vaccinated mouse sera (p=0.0006, two-tailed t-test comparing WT and CRR percent blocking values). This result implies that there was much greater 1B7 like neutralizing antibody in CRR vaccinated mouse sera than in WT mouse sera 3 DPC, and is consistent with increased anamnestic induction of 1B7 like antibody in CRR relative to WT vaccinated mice. Following similar logic, CRR vaccinated mice had 3.7 and 1.6-fold larger populations of DENV-2 serotype-specific potently neutralizing 9A3D-8 and 3H5 like antibodies than did WT vaccinated mice, 2.4 and 2.0-fold greater sub-complex cross-reactive neutralizing 1A1D-2 and 9D12 like antibodies, and 3.1 and 2.1-fold more DENV complex cross-reactive weakly and non-neutralizing 10-D35A and D3-5C9-1 like antibodies respectively. Lastly, the neutralizing capabilities of these seven MAbs were determined since not all had been previously published in the literature (Table 3). DENV-2 serotype specific MAbs 3H5 and 9A3D-8 showed the strongest DENV-2 neutralization ($NT_{50}$=0.15 and 0.94 µg/mL respectively). 1A1D-2 also potently neutralized DENV-2 (0.46 µg/mL) although it neutralized DENV-1 and DENV-3 about 3 times less than DENV-2 which was similar to the moderate DENV-2 neutralizing capabilities of both 9D12 and 1B7. D3-5C9-1 or 10-D35A did not neutralize any serotype strongly but 10-D35A did exhibit weak neutralization of DENV-2 (13.04 µg/mL). These results support the pattern of neutralization observed with polyclonal vaccinated mouse serum 3 DPC, suggesting that the 100-fold greater DENV-2 neutralizing capability of CRR vaccinated mouse serum was due mostly to increased populations of potently neutralizing DENV-2 type-specific and some sub-complex cross-reactive antibodies, and less so from increased populations of moderately neutralizing, cross-reactive antibodies like 1B7 and 9D12.

Thus, the greater than 100-fold increase in DENV-2 neutralization by pVD1-CRR vaccinated mice 3 DPC with DENV-2 was due to rapid, large increases in neutralizing antibody populations with diverse patterns of cross-reactivity that not only effectively protected mice from enhanced DENV-2 disease mortality but also exhibited significantly increased neutralization breadth across the DENV complex. This pattern of increased breadth of cross-neutralization by CRR vaccination bodes well for the use of tetravalent dengue CRR vaccines to rapidly induce balanced and protective tetravalent immunity, a dengue vaccine goal that continues to elude vaccine developers.

Taken together, these findings demonstrate that pVD1-WT vaccinated mice exhibited a classic pathological pattern of 'original antigenic sin' with anamnestic immune responses to immunodominant cross-reactive epitopes stimulated by the vaccine that not only interfered with subsequent DENV-2 specific immunity but produced increased immunopathology. Conversely, pVD1-CRR vaccinated mice were not burdened by original antigenic sin and were able to capitalize on it to rapidly mount a large magnitude, redirected, neutralizing immune response, effective at controlling DENV-2 viremia that was lacking in WT vaccinated mice.

TABLE 1

Nucleotide sequences of mutagenic primers

| Primer | Primer Sequence (5'-3')[1] | | SEQ ID NO: |
|---|---|---|---|
| | Nucleotide Substitution | Amino Acid Substitution | |
| D1-G106R | TTCCTTTCCGAAGAGACGACAGCCATTGCCCCAGCC<br>GGG-CGT | Gly-Arg | 13 |
| D1-L107D | TTCCTTTTCCGAAATCCCCACAGCCATTGCCCCAG<br>CTC-GAT | Leu-Asp | 14 |
| D1-G106RL107D | CTTCCTTTTCCGAAATCCCGACAGCCATTGCCCCAGCC<br>GGA-CGG<br>CTC-GAT | Gly-Arg<br>Leu-Asp | 15 |
| D1-K310D | AGCCACTTCGTCCTCTAGCTTGAATGAGCCTGTGC<br>AAA-GAC | Lys-Asp | 16 |
| D1-E311K | TCAGCCACCTTTTTCTCTAGCTTGAATGAGCCTGTGC<br>GAA-AAG | Glu-Lys | 17 |

TABLE 1-continued

Nucleotide sequences of mutagenic primers

| Primer | Primer Sequence (5'-3')[1] Nucleotide Substitution | Amino Acid Substitution | SEQ ID NO: |
|---|---|---|---|
| D1-K310DE311K | GGGTCTCAGCCACCTTGTCCTCTAGCTTGAATGAGCCTGTGC | | 18 |
| | AAA-GAC | Lys-Asp | |
| | GAA-AAG | Glu-Lys | |
| D1-P364Q | GCCTCAATGTTGACCTGTTTTTCTTTGTCAGTGACTATGGG | | 19 |
| | CCA-CAG | Pro-Gln | |

[1] Mutated nucleotides are shown in bold

TABLE 2

(part I). MAb reactivities for DENV-1 VLP mutants[1]

| | | MAb: | | | | | | |
|---|---|---|---|---|---|---|---|---|
| | MHAF | 4G2 | 6B6C-1 | 4A1B-9 | 23-1 | 23-2 | 5H3 | 5-2 |
| | | | | CR[2]: | | | | |
| | poly-clonal | group | group | group | group | group | group | sub grp. |
| | | | | Virus[3]: | | | | |
| | % secrt'n | D1 | D2 | SLEV | MVEV | WNV | JEV | YFV | JEV |
| VLP construct | | | | | | | | | |
| WT DENV-1[4] | 100 | 5.7 | 6.6 | 5.1 | 4.8 | 5.4 | 6.6 | 5.1 | 4.5 |
| G106R | 200 | 100 | <0.1 | 12.5 | 1.5 | 25 | 100 | nd[5] | 100 |
| L107D | 150 | 100 | <0.1 | 50 | 100 | <0.1 | 25 | nd | <0.6 |
| G106RL107D | 130 | 100 | <0.1 | 0.8 | 1.5 | <0.1 | <0.1 | 0.8 | 3.0 |
| K310D | 63 | 100 | <0.1 | 100 | 100 | 100 | 100 | nd | 150 |
| E311K | 50 | 100 | 100 | 100 | 100 | 100 | 100 | nd | 50 |
| P364Q | 50 | 100 | <0.1 | 100 | 100 | 100 | 100 | nd | 50 |
| K310DE311K P364Q | 10 | 100 | 100 | 50 | 12.5 | 100 | 100 | nd | 50 |
| G106RL107D K310DE311K P364Q | 91 | 100 | <0.1 | 3.0 | <0.1 | <0.1 | <0.1 | <0.1 | <0.6 |

(part II). MAb reactivities for DENV-1 VLP mutants[1]

| | MAb: | | | | | | |
|---|---|---|---|---|---|---|---|
| | 1B7 | D3-5C9-1 | 10-D35A | 20-783-74014 | 1A1D-2 | 9D12 | MDVP-55A | D2-1F1-3 |
| | | | | CR[2]: | | | | |
| | sub grp. | comp | comp | comp | sub comp | sub comp | sub comp | type-spec. |
| | | | | Virus[3]: | | | | |
| | D2 | D4 | DENV | DENV | D2 | D1 | DENV | D1 |
| VLP construct | | | | | | | | |
| WT DENV-1[4] | 6.3 | 4.7 | 5.7 | 5.1 | 5.7 | 5.1 | 4.2 | 6.3 |
| G106R | 0.8 | 100 | nd | nd | 25 | 100 | nd | 100 |
| L107D | 50 | 100 | nd | nd | 100 | 100 | nd | 100 |
| G106RL107D | 100 | 100 | nd | nd | 100 | 50 | nd | 100 |
| K310D | 100 | 100 | 100 | <0.1 | 1.5 | <0.8 | <1.3 | 100 |
| E311K | 100 | 100 | 100 | 3.9 | 50 | <0.16 | 5.6 | 100 |
| P364Q | 100 | 100 | 100 | 50 | 100 | 100 | 100 | 100 |
| K310DE311K P364Q | 100 | 100 | 100 | <0.1 | <0.8 | <0.16 | <0.6 | 100 |

TABLE 2-continued

| | | | | | | | | |
|---|---|---|---|---|---|---|---|---|
| G106RL107D K310DE311K P364Q | 100 | 100 | 50 | <0.1 | <0.1 | <0.1 | <0.6 | 100 |

[1] Reactivity levels for MAbs exhibiting varying cross-reactivity (CR) selected from different flaviviruses for wild-type (WT) and mutant VLP.
[2] MHAF is polyclonal murine hyper-immune ascitic fluid, group CR antibodies recognize all viruses of at least the four major pathogenic flavivirus serocomplexes; sub-group CR MAbs recognize all or some members of two or more different flavivirus serocomplexes (e.g., MAb 5-2 recognizes JEV, DENV-1 and DENV-2 respectively); complex (comp) and sub-comp CR MAbs recognize all four DENV complex viruses or a subset thereof respectively, and type-specific MAbs recognize only DENV-1.
[3] Virus the MAb was raised against; D1 = dengue virus serotype 1 (DENV-1), D2 = DENV-2, D3 = DENV-3, D4 = DENV-4, SLEV = St. Louis encephalitis virus, MVEV = Murray Valley encephalitis virus, WNV = West Nile virus, JEV = Japanese encephalitis virus, YFV = yellow fever virus. MAbs 20-783 and MDVP-55A are commercial MAbs raised against 'dengue virus'.
[4] MAb reactivities for wild-type (WT) DENV-1 VLP are presented as inverse $\log_{10}$ Ag-capture ELISA endpoint values and all mutant VLPs as percent of remaining reactivity compared to WT. Emboldened values represent reactivity reductions greater than 90% relative to WT.
[5] nd denotes not determined.

TABLE 3 pVD1-CRR vaccine increases the immunodominance of diverse neutralizing antibody populations following heterologous DENV-2 challenge

| | MAb: | | | | | | |
|---|---|---|---|---|---|---|---|
| | 1B7 | 9A3D-8 | 3H5 | 1A1D-2 | 9D12 | 10-D35A | D3-5C9-1 |
| Cross reactivity | comp+ | type | type | subcomp. | subcomp. | complex | complex |
| Percent blocking by pVD1-CRR vaccinated sera[1] | 37.0 | 78.6 | 66.6 | 66.2 | 62.7 | 55.7 | 121.5 |
| Percent blocking by pVD1-WT vaccinated sera | 2.3 | 21.2 | 40.9 | 27.3 | 31.8 | 18.2 | 59.1 |
| Fold pVD1-CRR increase in antibody population relative to pVD1-WT[2] | 16.4 | 3.71 | 1.63 | 2.43 | 1.97 | 3.06 | 2.06 |
| p-value[3] | 0.0006 | <0.0001 | 0.0001 | <0.0001 | 0.0001 | 0.0014 | 0.0289 |
| $Nt_{50}$ (μg/mL) | | | | | | | |
| DENV-2 | 1.62 | 0.94 | 0.15 | 0.46 | 1.96 | 13.04 | >100 |
| DENV-1 | 0.32 | >20 | >20 | 1.68 | 1.21 | 64.18 | >100 |
| DENV-3 | 2.12 | nd[4] | nd | 1.26 | 1.64 | >100 | >100 |
| DENV-4 | 3.0 | nd | nd | >20 | >20 | >100 | >100 |

This table presents the results from an epitope-blocking ELISA conducted on pVD1-WT and pVD1-CRR vaccinated AG129 mouse sera three days post challenge (DPC) with a sub-lethal dose of DENV-2.

[1] Average percent blocking of labeled MAbs by vaccinated mouse sera from four independent epitope-blocking ELISA assays each conducted on pools of 3 DPC sera from four pVD1-CRR vaccinated mice and four pVD1-WT vaccinated mice.

[2] Fold increase in CRR vaccinated relative to WT vaccinated mouse sera for the blocking of labeled MAbs. Emboldened values are significantly greater percent blocking by CRR vaccinated sera.

[3] p-values from unpaired two-tailed t-test comparing percent blocking of labeled MAbs by pooled CRR vaccinated and WT vaccinated mouse serum.

[4] nd = not determined

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. An isolated cross-reactivity reduced dengue virus E-glycoprotein polypeptide, wherein the polypeptide is a dengue serotype 4 virus (DENV-4) E-glycoprotein polypeptide comprising a glutamic acid at position 106, an aspartic acid at position 107, an aspartic acid at position 310, a glutamine at position 311, a glutamine at position 389, an isoleucine at position 468, a threonine at position 478, a valine at position 482 and a leucine at position 487, numbered with reference to SEQ ID NO: 4.

2. The polypeptide of claim 1, wherein the amino acid sequence of the polypeptide is at least 95% identical to SEQ ID NO: 4, and wherein the polypeptide comprises a glutamic acid at position 106, an aspartic acid at position 107, an aspartic acid at position 310, a glutamine at position 311, a glutamine at position 389, an isoleucine at position 468, a threonine at position 478, a valine at position 482 and a leucine at position 487 of SEQ ID NO: 4.

3. The polypeptide of claim 1, wherein the amino acid sequence of the polypeptide comprises SEQ ID NO: 4.

4. An isolated dengue virus-like particle (VLP) comprising the polypeptide of claim 1.

5. The VLP of claim 4, further comprising a dengue virus prM protein.

6. A recombinant nucleic acid molecule encoding the polypeptide of claim 1.

7. The recombinant nucleic acid molecule of claim 6, comprising a nucleotide sequence at least 95% identical to SEQ ID NO: 12.

8. The recombinant nucleic acid molecule of claim 6, comprising the nucleotide sequence of SEQ ID NO: 12.

9. A vector comprising the recombinant nucleic acid molecule of claim 6.

10. An isolated cell comprising the vector of claim 9.

11. A composition comprising the polypeptide of claim 1, and a pharmaceutically acceptable carrier.

12. The composition of claim 11, further comprising an adjuvant.

13. A composition comprising the vector of claim 9 and a pharmaceutically acceptable carrier.

14. The composition of claim 13, further comprising an adjuvant.

15. A method of eliciting an immune response in a subject against dengue virus, comprising administering to the subject a therapeutically effective amount of the polypeptide of claim 1, thereby eliciting an immune response in the subject against dengue virus.

16. The method of claim 15, wherein the subject is a mammal.

17. The method of claim 16, wherein the subject is human.

18. A method of eliciting an immune response in a subject against dengue virus, comprising administering to the subject a therapeutically effective amount of the vector of claim 9, thereby eliciting an immune response in the subject against dengue virus.

19. The method of claim 18, wherein the subject is a mammal.

20. The method of claim 19, wherein the subject is human.

* * * * *